US011568493B2

(12) United States Patent
Rolih et al.

(10) Patent No.: US 11,568,493 B2
(45) Date of Patent: Jan. 31, 2023

(54) COMPUTING DEVICE WITH IMPROVED USER INTERFACE FOR COLLECTION BASED ON PATIENT SERVICES PROVIDED BY A HEALTH CARE PROVIDER

(71) Applicant: JZANUS I.T. SERVICES, LLC, Franklin Square, NY (US)

(72) Inventors: Hilary P. Rolih, Franklin Square, NY (US); John Sullivan, Franklin Square, NY (US)

(73) Assignee: JZANUS I.T. SERVICES, LLC, Franklin Square, NY (US)

( * ) Notice: Subject to any disclaimer, the term of this patent is extended or adjusted under 35 U.S.C. 154(b) by 59 days.

(21) Appl. No.: 16/511,455

(22) Filed: Jul. 15, 2019

(65) Prior Publication Data

US 2020/0034933 A1 Jan. 30, 2020

Related U.S. Application Data

(60) Provisional application No. 62/703,040, filed on Jul. 25, 2018.

(51) Int. Cl.
*G06Q 40/08* (2012.01)
*G16H 10/60* (2018.01)
*G06Q 10/10* (2012.01)

(52) U.S. Cl.
CPC ............. *G06Q 40/08* (2013.01); *G06Q 10/10* (2013.01); *G16H 10/60* (2018.01)

(58) Field of Classification Search
CPC ......... G06Q 40/08; G06Q 10/10; G16H 10/60
See application file for complete search history.

(56) References Cited

U.S. PATENT DOCUMENTS 6,549,894 B1 * 4/2003 Simpson ................ G06Q 10/10
6,859,806 B1 * 2/2005 Kamarei ................ G06Q 10/10
(Continued)

FOREIGN PATENT DOCUMENTS

JP 2008517405 A * 5/2008 ........... G06Q 40/025
WO WO-2004111766 A2 * 12/2004 ........... G06Q 10/087

OTHER PUBLICATIONS

Bruce Young. "Docketing systems". National Association of Patent Practitioners Ann. Meeting. (Jul. 14, 2015). https://napp.memberclicks.net/assets/2015AMCMaterials/2015amctues4young.pptx (Year: 2015).*
(Continued)

*Primary Examiner* — Ayal I. Sharon
(74) *Attorney, Agent, or Firm* — F. Chau & Associates, LLC

(57) ABSTRACT

A computing device includes a first program configured to display a menu on a screen and display a summary on the screen that can be reached directly from the menu, and a second program. The summary displays patient account information of a plurality of patient accounts for a selected one of a plurality of available clients. The displayed patient account information includes a plurality of displayed entries, where each entry includes a first field indicating an account number of one of the patient accounts, a second field indicating a status associated with the account number, and a third field indicating a due date. The second program causes the third field to display a due date for submitting a claim associated with the account number to insurance, and dynamically updates the third field to display a due date for appealing denial of the claim.

14 Claims, 69 Drawing Sheets

(56) References Cited

U.S. PATENT DOCUMENTS

| | | | | |
|---|---|---|---|---|
| 8,086,474 B1* | 12/2011 | Lasalle | G06Q 40/00 | 705/4 |
| 8,103,527 B1* | 1/2012 | Lasalle | G06Q 40/08 | 705/4 |
| 8,543,932 B2* | 9/2013 | Fields | G06Q 10/067 | 715/762 |
| 8,615,414 B2* | 12/2013 | Voccola | G06Q 40/08 | 705/4 |
| 8,738,402 B2* | 5/2014 | Chapman | G16H 40/67 | 705/2 |
| 9,940,363 B2* | 4/2018 | Lundberg | G06F 16/93 | |
| 9,940,683 B2* | 4/2018 | Huynh | G06Q 40/04 | |
| 10,242,066 B2* | 3/2019 | Lundberg | G06F 16/2455 | |
| 10,664,921 B1* | 5/2020 | Frens | G06F 16/33 | |
| 10,971,264 B1* | 4/2021 | Dudzinski | G16H 40/20 | |
| 2003/0144948 A1* | 7/2003 | Cleary | G06Q 40/025 | 705/38 |
| 2003/0167184 A1* | 9/2003 | Kole | G16H 10/20 | 705/2 |
| 2004/0059661 A1* | 3/2004 | Arndt | G06Q 10/10 | 705/36 R |
| 2004/0249665 A1* | 12/2004 | David | G06Q 40/08 | 705/2 |
| 2005/0010446 A1* | 1/2005 | Lash | G06Q 10/10 | 705/2 |
| 2005/0065816 A1* | 3/2005 | Limberg | G06Q 30/04 | 705/2 |
| 2006/0064313 A1* | 3/2006 | Steinbarth | G06Q 10/1057 | 705/322 |
| 2008/0177577 A1* | 7/2008 | Olaniyan | G06F 19/328 | 705/3 |
| 2011/0145021 A1* | 6/2011 | Denny, Jr. | G06Q 20/102 | 705/4 |
| 2011/0213830 A1* | 9/2011 | Lopez | G06Q 10/06 | 709/203 |
| 2013/0159025 A1* | 6/2013 | Olaniyan | G06Q 50/18 | 705/4 |
| 2013/0317867 A1* | 11/2013 | Cecil | G06Q 40/08 | 705/4 |
| 2014/0006061 A1* | 1/2014 | Watanabe | G06Q 40/08 | 705/4 |
| 2014/0006065 A1* | 1/2014 | Olaniyan | G06F 19/328 | 705/4 |
| 2021/0264533 A1* | 8/2021 | Feit | G06Q 40/08 | |

OTHER PUBLICATIONS

John Pani and John Freeman. "Understanding Patent Examiner Docketing & Workflow to Expedite Prosecution". (Oct. 25, 2016). https://www.brinksgilson.com/files/17109_Docketing_and_Workflow_Webinar_-_FINAL.pdf (Year: 2016).*

Google's English language translation of JP2008517405A. Downloaded on Jan. 14, 2022. https://patents.google.com/patent/JP2008517405A/en?oq=JP-2008517405-A (Year: 2022).*

Jörg H. Hohnloser & Florian Pürner. "PADS (Patient Archiving and Documentation System): A computerized patient record with educational aspects". International Journal of Clinical Monitoring and Computing. vol. 9, Article No. 71 (Jun. 1992). https://link.springer.com/article/10.1007/BF01142184 (Year: 1992).*

* cited by examiner

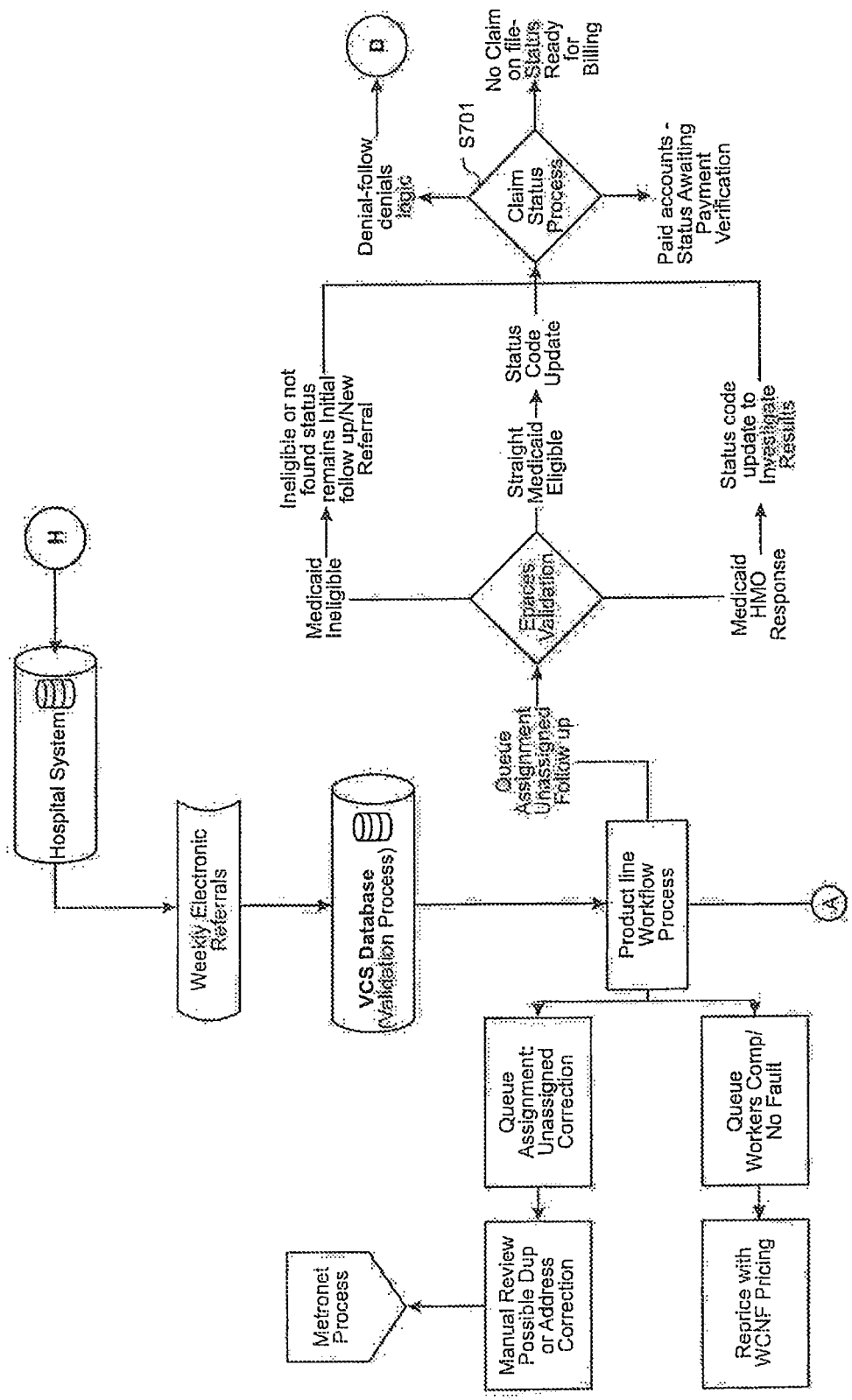
FIG. 7A1

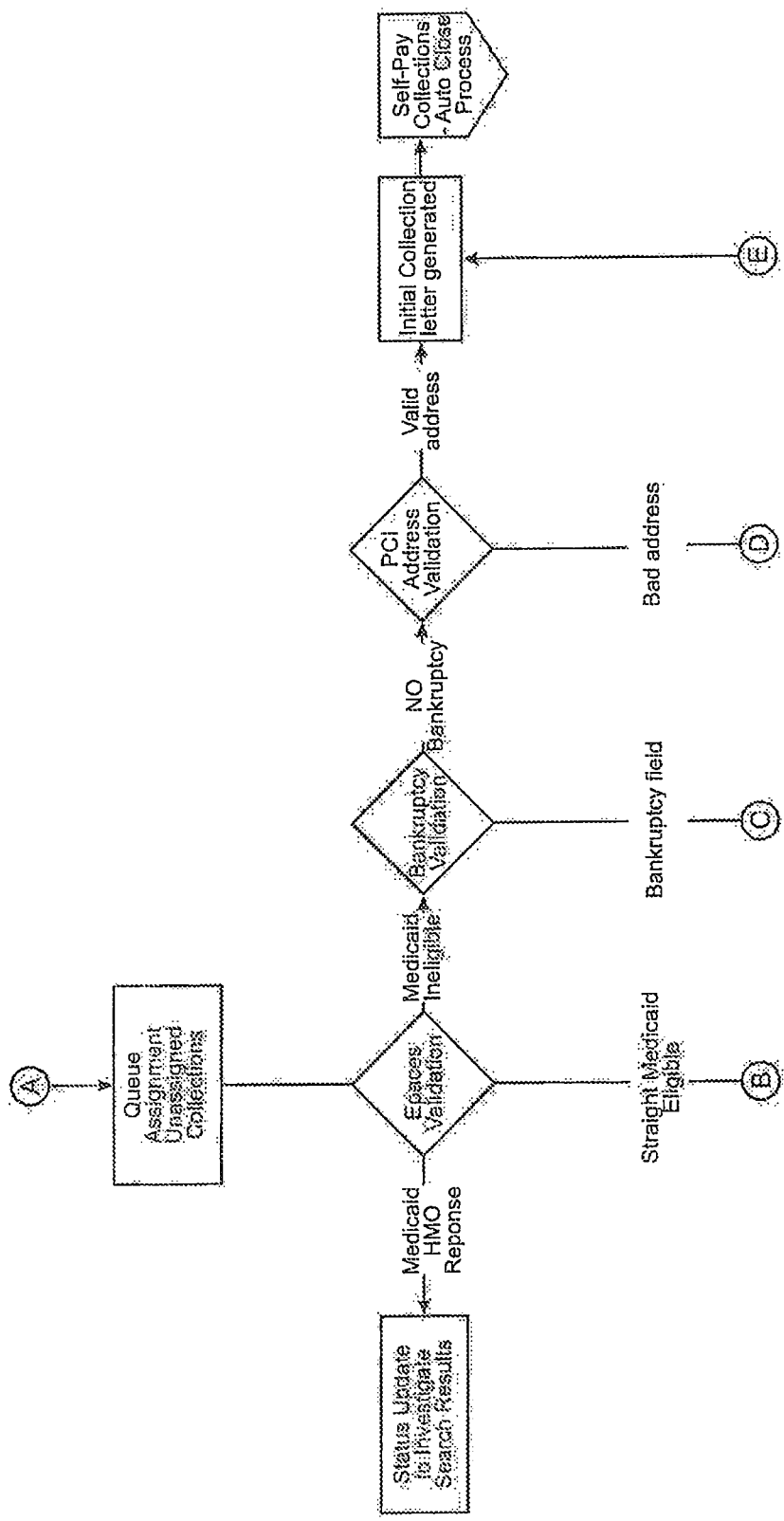
FIG. 7A2

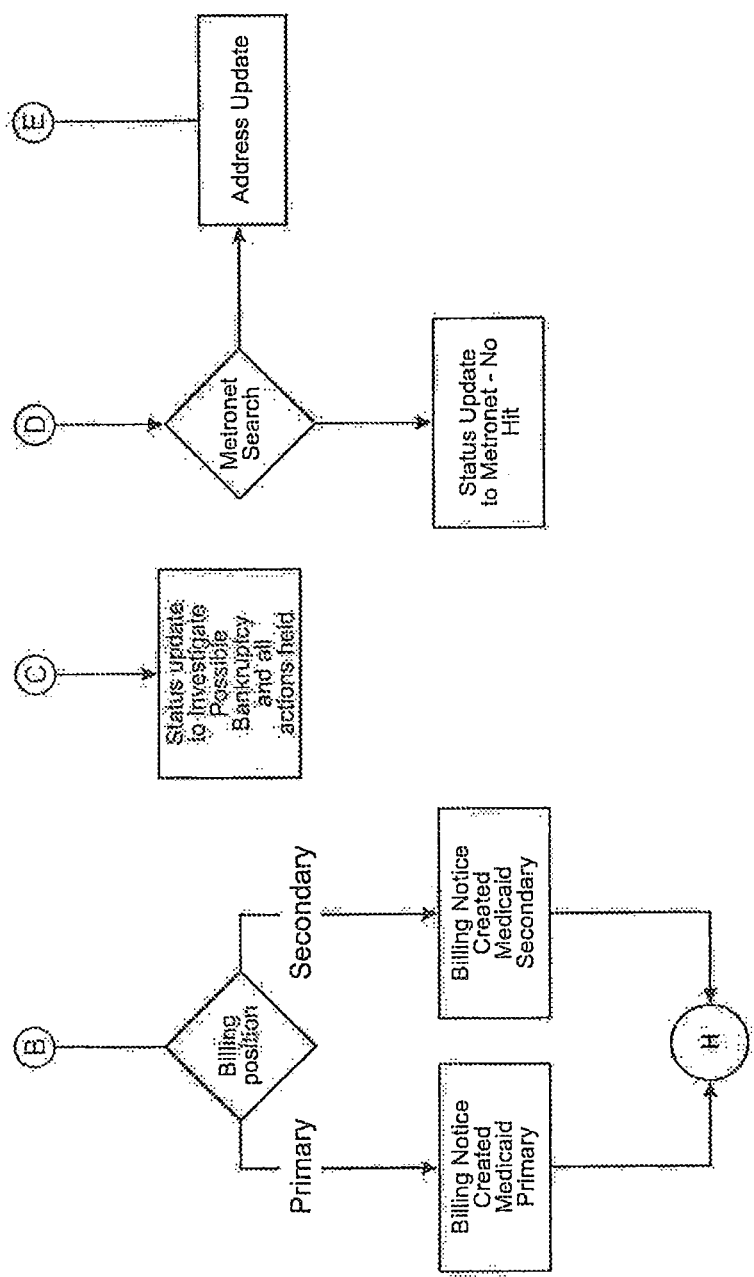
FIG. 7A3

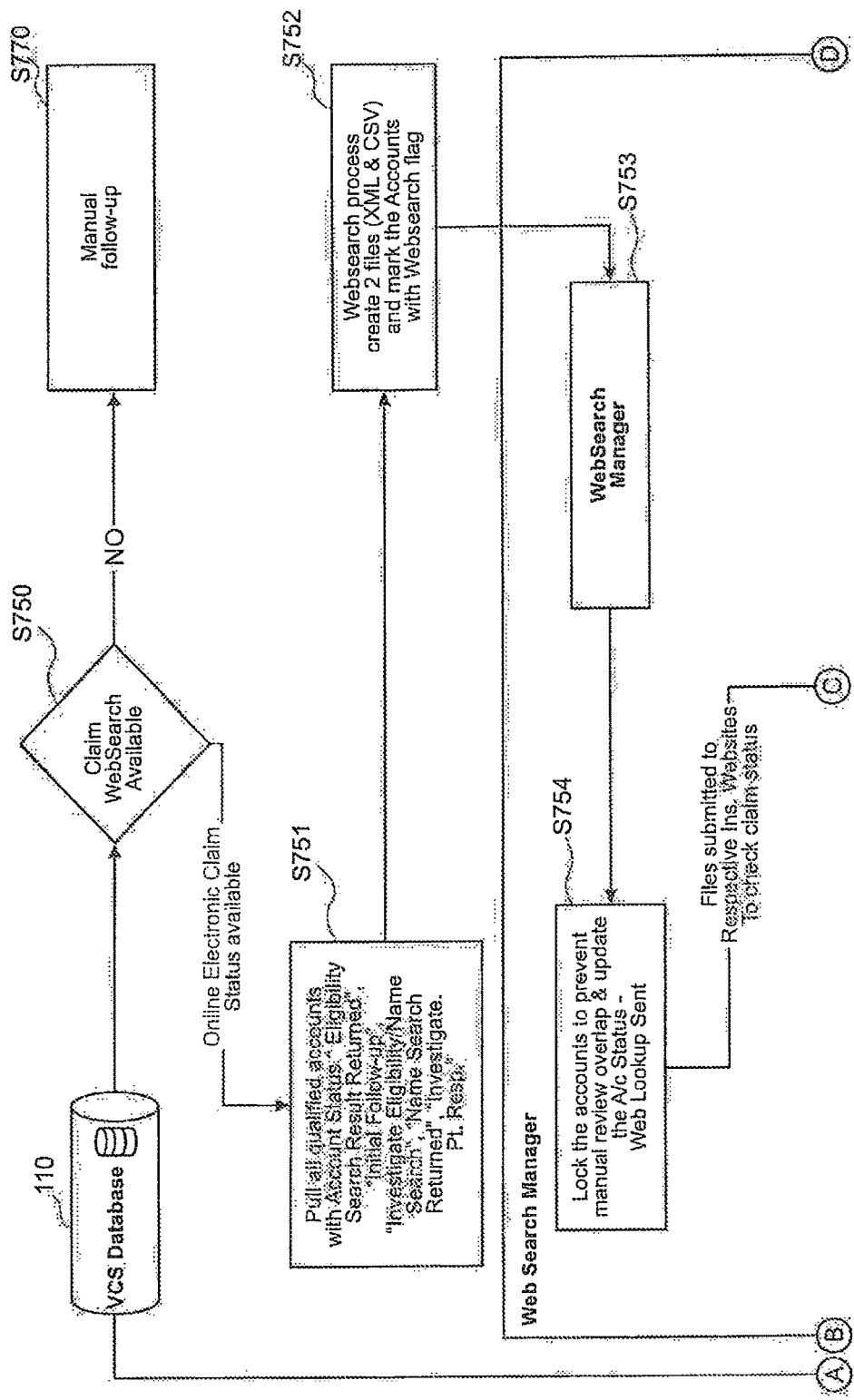
FIG. 7B1

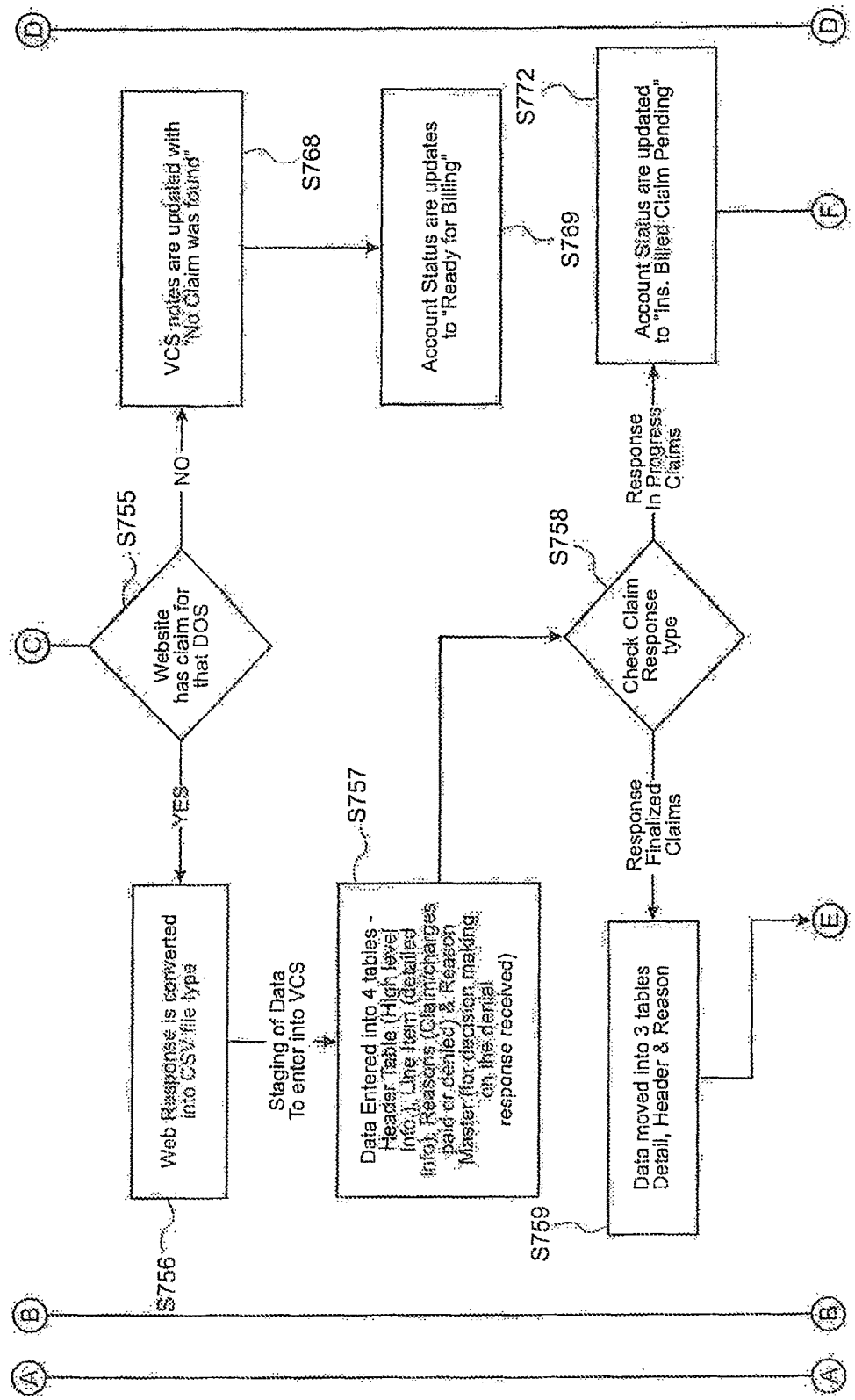
FIG. 7B2

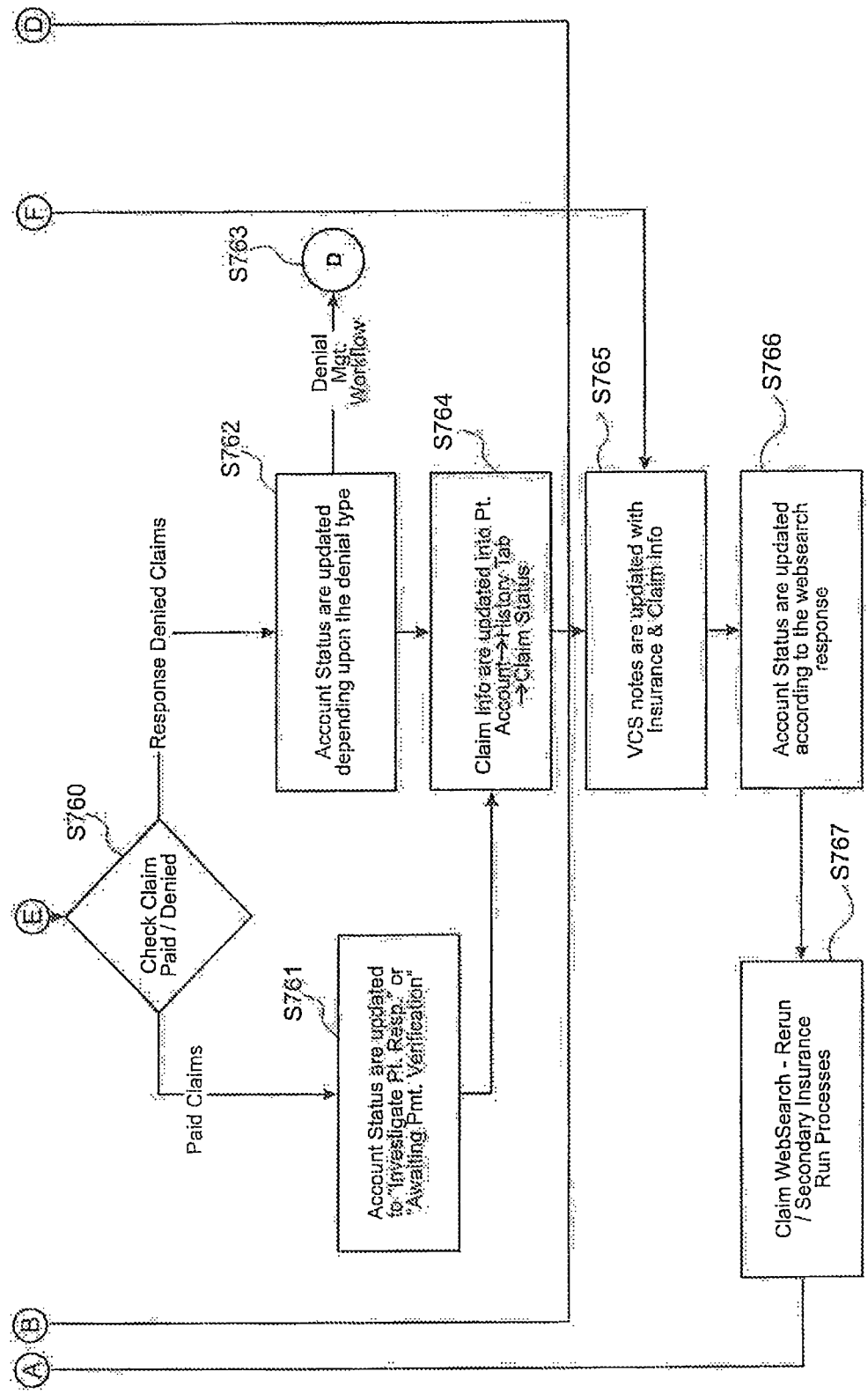
FIG. 7B3

| | | | | |
|---|---|---|---|---|
| Department: | OUTPATIENT DEPARTMENT | | | |
| Visit Type: | <<All>> | | | |
| Client (Expand): | TEST HEALTH SYSTEM / VICTORY MEMORIAL | | | |
| Hospital Name (Expand): | <<All>> / SAMPLE HOSPITAL | | | |
| Product Line: | INSURANCE FOLLOW UP | | | |
| Open/Close: | Open | | | |
| Status (Expand): | <<All>> / KINGSTON IN ACTIVE STATUS - MUST | | | |
| Resolution: | <<All>> | | | |
| Investigator: | <<All>> | | | |
| Queue: | <<All>> | | | |
| Primary Insurance Carrier (Expand): | <<All>> / 135 BENTON DRIVE OPERATING COMPANY | | | |

[Show Summary]   [Run]   [Ca...]

| Client Acct # | Patient Name | Balance | DOS | Hospital |
|---|---|---|---|---|
| 1219988322 | ILYADZHANOVA, TEEKARAM | $384.76 | 02/21/2018 | SAMPLE HOSPITAL |
| 1219988239 | BRYC, ANDALUZ | $569.64 | 02/16/2018 | SAMPLE HOSPITAL |
| 1219988292 | MMITTIS, JABBAR | $582.93 | 02/16/2018 | SAMPLE HOSPITAL |
| 1219988319 | JARITIC, CHARLENE | $780.67 | 02/05/2018 | SAMPLE HOSPITAL |
| 1219988306 | ELAGA, PITIC | $1,915.00 | 02/14/2018 | SAMPLE HOSPITAL |
| 1219988318 | IELMMARI, DAVIS | $497.38 | 02/13/2018 | SAMPLE HOSPITAL |
| 1219988305 | FRINCIS, XHELAJ | $334.40 | 02/12/2018 | SAMPLE HOSPITAL |
| 1219988302 | FIELICINA, ROBERT | $267.74 | 02/09/2018 | SAMPLE HOSPITAL |
| 1219988294 | WIELELIR, GOLDMAN | $372.00 | 02/09/2018 | SAMPLE HOSPITAL |
| 1219988252 | BIELTAN, SANDRA | $320.82 | 02/08/2018 | SAMPLE HOSPITAL |
| 1219988323 | ELIN, BRENDA | $335.20 | 02/08/2018 | SAMPLE HOSPITAL |
| << 1 2 3 4 5 >> | | $534.70 | 02/08/2018 | SAMPLE HOSPITAL |

FIG 20A

| Received Date: | 01/01/2018 | | To: | 04/30/2018 | |
| --- | --- | --- | --- | --- | --- |
| DOS: | MM/DD/YYYY | | To: | MM/DD/YYYY | |
| Status Date: | MM/DD/YYYY | | To: | MM/DD/YYYY | |
| Resolution Date: | MM/DD/YYYY | | To: | MM/DD/YYYY | |
| Worked From Date: | MM/DD/YYYY | | To: | MM/DD/YYYY | |
| CAID Date: | MM/DD/YYYY | | To: | MM/DD/YYYY | |
| Dialer Date: | MM/DD/YYYY | | To: | MM/DD/YYYY | |
| Due Date: | MM/DD/YYYY | | To: | MM/DD/YYYY | |
| Entered Date: | MM/DD/YYYY | | To: | MM/DD/YYYY | |
| TQM Date: | MM/DD/YYYY | | To: | MM/DD/YYYY | |

Financial Class: _____  Plan Code: _____
Clinic Code: _____
Days after DOS: _____  Aged - Received: _____

[ ncel ]  [ Close ]

| Status / Resolution | Status Date | Investigator | Received |
| --- | --- | --- | --- |
| SPLIT PLAN BILLING | 03/13/2018 | JBROW002 | 03/05/2018 |
| REVIEW PRIOR PAYMENT | 03/13/2018 | JBROW002 | 03/02/2018 |
| SPLIT PLAN BILLING | 03/13/2018 | JBROW002 | 03/02/2018 |
| REVIEW PRIOR PAYMENT | 03/08/2018 | | 03/05/2018 |
| NO CLAIM NO FILE | 05/15/2018 | RDOUG001 | 03/04/2018 |
| REBILL NEEDED | 03/08/2018 | | 03/05/2018 |
| REBILL NEEDED | 03/13/2018 | CMARI001 | 03/04/2018 |
| NO CLAIM NO FILE | 05/15/2018 | JBROW002 | 03/03/2018 |
| AWAITING ADDITIONAL INFORMATION TO BILL | 03/16/2018 | DBATC001 | 03/02/2018 |
| INSURANCE BILLED - CLAIM PENDING | 03/06/2018 | CMARI001 | 02/25/2018 |
| NO CLAIM NO FILE | 05/15/2018 | JBROW002 | 03/05/2018 |
| INSURANCE BILLED - CLAIM PENDING | 03/06/2018 | CMARI001 | 02/25/2018 |

| | | | | |
|---|---|---|---|---|
| Dispo Code: | | | | |
| Account Calls: | ▽ | | 0 | |
| Balance $: | ▽ | | $0.00 | |
| Referral $: | ▽ | | $0.00 | |

☐ MH  ▨ E-Claims  ☐ Legal
☐ Web Sent  ☐ Letters on Hold  ☐ Locked
☐ Not Worked  ☐ Returned  ☐ Submitted
☐ Billed  ☐ Denial  ☐ NCOF
☐ P/A:  ⦿ Open  ○ Broken
Phone Type:  ⦿ All  ○ Cell  ○ Home

Report Section

Report Type:  ⦿ PDF  ○ Excel  [ Print ]

Portfolios:  [ Open Portfolio ]  [ Save Portfolio ]

Client System

| Carrier | Total # | Total $ | Due Date | Notes |
|---|---|---|---|---|
| EMPIRE BCBS | 4 | $4,480.76 | Past Due | ... |
| EMPIRE BCBS | 1 | $569.93 | | ... |
| EMPIRE BCBS | 1 | $582.93 | Past Due | ... |
| FIDELIS | 2 | $1,047.37 | Past Due | ... |
| CIGNA | 1 | $1,915.00 | Past Due | ... |
| FIDELIS | 1 | $497.38 | Past Due | ... |
| HIP | 1 | $334.40 | 02/26/2019 | ... |
| BLUE CARD CLAIM | 1 | $267.74 | 02//08/2019 | ... |
| AFTNA | 1 | $372.00 | Past Due | ... |
| HIP | 1 | $320.82 | 02/07/2019 | ... |
| EMPIRE BCBS | 1 | $335.20 | Past Due | ... |
| HIP | 1 | $534.70 | 02/07/2019 | ... |
| Total: | | $339,027.72 | | 482 |

| | | | | | |
|---|---|---|---|---|---|
| Received Date: | 01/01/2018 | | To: | 01/31/2018 | |
| DOS: | MM/DD/YYYY | | To: | MM/DD/YYYY | |
| Status Date: | MM/DD/YYYY | | To: | MM/DD/YYYY | |
| Resolution Date: | MM/DD/YYYY | | To: | MM/DD/YYYY | |
| Worked From Date: | MM/DD/YYYY | | To: | MM/DD/YYYY | |
| CAID Date: | MM/DD/YYYY | | To: | MM/DD/YYYY | |
| Dialer Date: | MM/DD/YYYY | | To: | MM/DD/YYYY | |
| Due Date: | MM/DD/YYYY | | To: | MM/DD/YYYY | |
| Entered Date: | MM/DD/YYYY | | To: | MM/DD/YYYY | |
| TQM Date: | MM/DD/YYYY | | To: | MM/DD/YYYY | |

Financial Class: ____   Plan Code: ____
Clinic Code: ____
Days after DOS: ____   Aged - Received: ____

[ ncel ]   [ Close ]

○ Resolution  ○ Dialer  ⊘ F/C ⊘  P/C ⊘  Denial  ○ Aging  ○ Carrier

FIG. 21B

| | Balance | # Accounts |
|---|---|---|
| | $17,259.46 | 21 |
| | $75.15 | 1 |
| | $32,938.44 | 41 |
| | $10,184.26 | 10 |
| | $1,917.69 | 2 |
| | $6,462.17 | 9 |
| | $3,474.26 | 5 |
| | $7,859.85 | 15 |
| | $14,225.91 | 18 |
| | $2,939.09 | 5 |
| | $4,607.72 | 9 |
| | $3,263.68 | 7 |
| | $14,939.04 | 26 |
| | $40,807.09 | 84 |
| Total: | $164,160.93 | 259 |

FIG. 21C

| | | |
|---|---|---|
| Department: | OUTPATIENT DEPARTMENT | |
| Visit Type: | <<All>> | |
| Client (Expand): | TEST HEALTH SYSTEM | |
| Hospital Name (Expand): | <<All>> SAMPLE HOSPITAL | |
| Product Line: | <<All>> | |
| Open/Close: | Open | |
| Status (Expand): | <<All>> | |
| Resolution: | <<All>> | |
| Investigator: | <<All>> | |
| Queue: | <<All>> | |
| Primary Insurance Carrier (Expand): | <<All>> 135 BENTON DRIVE OPERATING COMP | |

Show Summary    Run    Ca

| Client Acct # | Patient Name | Balance | DOS | Hospital |
|---|---|---|---|---|
| 1219987864 | FIELDAS, TAYLOR | $2,857.00 | 10/27/2017 | SAMPLE HOSPITAL |
| 1219987931 | NITHISING, WILLS | $2,001.94 | 11/09/2017 | SAMPLE HOSPITAL |
| 1219988055 | SHIVKEYITAV, BULLUCK | $1,521.93 | 11/30/2017 | SAMPLE HOSPITAL |
| 1219987952 | COLOBY, PATRICIA | $1,520.00 | 12/16/2017 | SAMPLE HOSPITAL |
| 1219987917 | INDARIDAI, DIAZ | $1,520.00 | 11/11/2017 | SAMPLE HOSPITAL |
| 1219988125 | BRENTON, CLEVELAND | $972.40 | 12/26/2017 | SAMPLE HOSPITAL |
| 1219988223 | IELMMIRIZ, VANDETTA | $754.35 | 03/07/2017 | SAMPLE HOSPITAL |
| 1219987928 | TEICHICA, NUNEZ | $741.00 | 12/23/2017 | SAMPLE HOSPITAL |
| 1219987884 | GIRISH, SANCHEZ | $741.00 | 12/12/2017 | SAMPLE HOSPITAL |
| 1219988248 | GANZIELIZ, COLON | $741.00 | 12/21/2017 | SAMPLE HOSPITAL |
| 1219988228 | BRADFORD, SALIMAH | $631.17 | 12/18/2017 | SAMPLE HOSPITAL |
| 1219988331 | ALONSO, GUTIERREZ | $550.42 | 12/29/2017 | SAMPLE HOSPITAL |
| 1219988088 | MMIRTINIZ, AGUAIRA | $498.79 | 12/05/2017 | SAMPLE HOSPITAL |
| 1219987880 | MMIRTINIZ, AGUAIRA | $325.40 | 11/15/2017 | SAMPLE HOSPITAL |

| | Received Date: | 01/01/2018 | | To: | 01/31/2018 | |
|---|---|---|---|---|---|---|
| | DOS: | MM/DD/YYYY | | To: | MM/DD/YYYY | |
| | Status Date: | MM/DD/YYYY | | To: | MM/DD/YYYY | |
| | Resolution Date: | MM/DD/YYYY | | To: | MM/DD/YYYY | |
| | Worked From Date: | MM/DD/YYYY | | To: | MM/DD/YYYY | |
| | CAID Date: | MM/DD/YYYY | | To: | MM/DD/YYYY | |
| | Dialer Date: | MM/DD/YYYY | | To: | MM/DD/YYYY | |
| | Due Date: | MM/DD/YYYY | | To: | MM/DD/YYYY | |
| | Entered Date: | MM/DD/YYYY | | To: | MM/DD/YYYY | |
| | TQM Date: | MM/DD/YYYY | | To: | MM/DD/YYYY | |

Financial Class: [    ]   Plan Code: [    ]
Clinic Code: [    ]
Days after DOS: [    ]   Aged - Received: [    ]

[ncel]  [Close]

| | Status / Resolution | Status Date | Investigator | Receive |
|---|---|---|---|---|
| | AWAITING ADDITIONAL INFORMATION TO BILL | 02/21/2018 | DBATC001 | 01/03/ |
| | AWAITING ADDITIONAL INFORMATION TO BILL | 03/07/2018 | DBATC001 | 01/21/2 |
| | AWAITING ADDITIONAL INFORMATION TO BILL | 03/16/2018 | RDOUG001 | 02/07/2 |
| | AWAITING ADDITIONAL INFORMATION TO BILL | 03/30/2018 | RDOUG001 | 01/25/2 |
| | AWAITING ADDITIONAL INFORMATION TO BILL | 03/02/2018 | RDOUG001 | 01/17/2 |
| | AWAITING ADDITIONAL INFORMATION TO BILL | 03/16/2018 | DBATC001 | 02/11/2 |
| | AWAITING ADDITIONAL INFORMATION TO BILL | 03/23/2018 | JBROW002 | 02/20/2 |
| | AWAITING ADDITIONAL INFORMATION TO BILL | 03/22/2018 | DBATC001 | 01/20/2 |
| | AWAITING ADDITIONAL INFORMATION TO BILL | 03/30/2018 | DBATC001 | 01/09/2 |
| | AWAITING ADDITIONAL INFORMATION TO BILL | 03/05/2018 | DBATC001 | 02/25/2 |
| | AWAITING ADDITIONAL INFORMATION TO BILL | 03/21/2018 | | 02/22/2 |
| | AWAITING ADDITIONAL INFORMATION TO BILL | 03/21/2018 | | 03/06/2 |
| | AWAITING ADDITIONAL INFORMATION TO BILL | 03/22/2018 | DBATC001 | 02/09/2 |
| | AWAITING ADDITIONAL | 03/23/2018 | DBATC001 | 01/08/2 |

| | Dispo Code: | | | |
|---|---|---|---|---|
| | Account Calls: | ▽ | | 0 |
| | Balance $: | ▽ | | $0.00 |
| | Referral $: | ▽ | | $0.00 |

☐ MH  ▨ E-Claims  ☐ Legal
☐ Web Sent  ☐ Letters on Hold  ☐ Locked
☐ Not Worked  ☐ Returned  ☐ Submitted
☐ Billed  ☐ Denial  ☐ NCOF
☐ P/A:  ◉ Open  ○ Broken
Phone Type:  ◉ All  ○ Cell  ○ Home

Report Section

Report Type:  ◉ PDF  ○ Excel  [Print]

Portfolios:  [Open Portfolio]  [Save Portfolio]

Client System

| d | Carrier | Total # | Total $ | Due Date | Notes |
|---|---|---|---|---|---|
| 018 | VETERANS ADMINISTRATION | 1 | $2,657.00 | | ... |
| 018 | CIGNA PROPERTY AND CASUALTY | 1 | $2,001.94 | | ... |
| 018 | AETNA | 2 | $3,043.86 | | ... |
| 018 | AETNA | 1 | $1,520.00 | Past Due | ... |
| 018 | AETNA | 1 | $1,520.00 | Past Due | ... |
| 018 | AETNA | 2 | $1,944.80 | Past Due | ... |
| 018 | OXFORD HEALTH PLAN | 1 | $754.36 | | ... |
| 018 | LOCAL 1199 | 1 | $741.00 | Past Due | ... |
| 018 | LOCAL 1199 | 1 | $741.00 | | ... |
| 018 | LOCAL 1199 | 1 | $741.00 | | ... |
| 018 | HEALTHFIRST | 1 | $631.17 | | ... |
| 018 | HEALTHFIRST | 1 | $550.43 | | ... |
| 018 | METROPLUS | 3 | $1,987.41 | | ... |
| 018 | METROPLUS | 3 | $1,987.41 | | |
| | Total | | $17,259.46 | | 21 |

FIG. 27B (Rotated screen contents:)

Figure 27B:
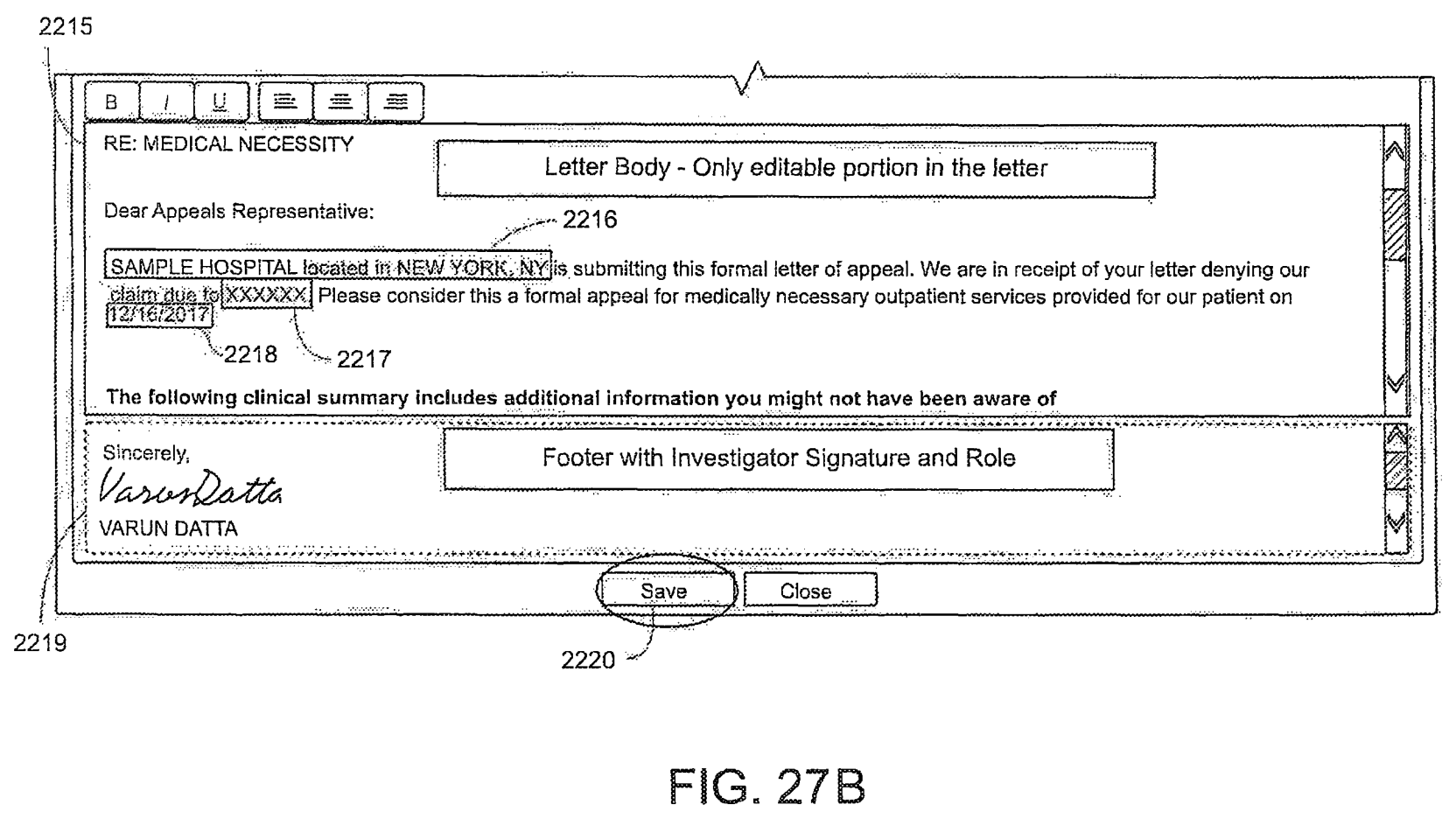

RE: MEDICAL NECESSITY

Letter Body - Only editable portion in the letter — 2216

Dear Appeals Representative:

SAMPLE HOSPITAL located in NEW YORK, NY is submitting this formal letter of appeal. We are in receipt of your letter denying our claim due to [XXXXX] Please consider this a formal appeal for medically necessary outpatient services provided for our patient on 12/16/2017.

2218  2217

The following clinical summary includes additional information you might not have been aware of Sincerely,
*Varun Datta*
VARUN DATTA Footer with Investigator Signature and Role Save   Close

| Form/Letters ◆ | Type ◆ | Dept ◆ | Created on ◆ | Created by ◆ | Status ◆ |
|---|---|---|---|---|---|
| MEDICAL NECESSITY | 1ST LEVEL APPEAL | 0 | 09/20/2018 | VDATT001 | Finalized |

[Complete] [Finalize] [Edit] [Print] [Void] [Close]

FIG. 30B

- [ ] Progress Notes
- [ ] Medications
- [ ] Discharge Summary
- [ ] Testing Results (Laboratory, Blood Work, Radiology, Cardiology tests etc.)
- [ ] Operative Report
- [ ] Physician Discharge Summary
- [ ] Preauthorization showing initial follow up for specific procedure performed on date
- [ ] Physician letter of medical necessity (i.e. outpatient testing, investigation treatments)
- [ ] Documentation does not match DOS appealing
- [ ] Other Sincerely,

*Varun Datta*

VARUN DATTA
Account Representative
516-326-0808 x 3501

2219

Footer with Investigator Signature and Role

2220

Save   Close

COMPUTING DEVICE WITH IMPROVED USER INTERFACE FOR COLLECTION BASED ON PATIENT SERVICES PROVIDED BY A HEALTH CARE PROVIDER

CROSS-REFERENCE TO RELATED APPLICATION

This application claims priority to U.S. Provisional Application No. 62/703,040, filed on Jul. 25, 2018, the disclosure of which is incorporated by reference herein.

BACKGROUND

1. Technical Field

The present disclosure relates generally to a computing device with an improved user interface for collection based on patient services provided by a healthcare provider.

2. Discussion of Related Art

Since information associated with each patient account is so voluminous and thousands of patient accounts are typically maintained, one of the problems facing designers of user interfaces for collection is how to allow a user to navigate quickly and to efficiently access only those patient accounts that are in arrears. Computing devices used for collection tend to need data of patient accounts and functions available for processing those accounts divided into many layers or views due to the sheer size of the data and the number of functions required. This problem is magnified on computing devices with small screens such as tablets. The user interface can be thought of as having many layers, with the user having to first locate the correct top level function and then, within that function, progressively drill down (sometimes through 3 or more layers) to complete the required task. User interfaces for collection typically include several applications, and then the user has to first locate, then start/open the required application, and then may need to navigate to the required function or cause the required data to be displayed.

For example, if a user needs to determine from one of these user interfaces, whether they are in time to submit a claim associated with a patient account to an insurance company or in time to appeal the subsequent denial of that claim, the user needs to access many of these applications and make multiple selections within each application to drill down to the required data, and then manually calculate all the due dates from the retrieved data. For example, a user might have to locate and start an application listing patient accounts, make filtering selections or queries to return a list of the accounts having claims that need to be submitted, select on one of the listed accounts to display a list of the claims that need to be submitted for the selected account, select on one of the listed claims, select a menu to determine the date the patient services were performed for the listed claim, select another menu to determine the insurance of the patient; locate and start an application listing all the insurance companies supported, select one of the listed insurance companies, select a menu asking the user to select whether the claim is based on worker's compensation, select a menu listing corresponding deadlines (e.g., worker's compensation deadlines/non-worker's compensation deadlines), select the listed deadline for submitting a claim to retrieve an amount of days, and then manually calculate the deadline for submitting the claims from all the retrieved information and possibly other data retrieved from a yet another menu.

For example, if a user needs to determine from one of these user interfaces whether they are in time to appeal the subsequent denial of a submitted claim, a user might have to locate and start an application listing patient accounts, make filtering selections or queries to return a list of the accounts having claims that were denied, select on one of the listed accounts to display a list of the claims that need to be appealed for the selected account, select on one of the listed claims, select a menu to retrieve the date the claim was denied for the listed claim, select another menu to determine the insurance of the patient; locate and start an application listing all the insurance companies supported, select one of the listed insurance companies, select a menu asking the user to select whether the claim is based on worker's compensation, select a menu listing corresponding deadlines (e.g., worker's compensation deadlines/non-worker's compensation deadlines), select the listed deadline for appealing a denial to retrieve an amount of days to appeal the denial, and then manually calculate the deadline for appealing the denial from all the retrieved information and possibly other data retrieved from a yet another menu.

The above-described user interfaces for determining the due dates are slow, complex and difficult to learn, particularly to novice users. Thus, those that use these interfaces miss many deadlines for submitting claims and miss many deadlines for appealing denial of submitted claims. Since insurance will not reimburse a healthcare provider when such deadlines are missed, the healthcare provider receives far less compensation for the services it provided. The reduced compensation may cause a healthcare provider to reduce the size of its staff, thereby reducing the quality of healthcare provided to subsequent patients. An effective user interface would ideally enable the user to readily and rapidly determine the claims that need to be submitted and the claims that needed to be appealed, to maximize the compensation the healthcare provider receives in exchange for its services. Designing such a user interface is however a complex human factors problem, especially for computing devices with small screens such as tablets.

Thus, there are several technical problems with regard to conventional user interfaces for collection based on patient services provided by a healthcare provider.

SUMMARY

Embodiments of the present disclosure solve one or more of the foregoing and other problems in the art with systems, non-transitory computer-readable media, and methods for providing an improved user interface for collection based on patient services provided by a healthcare provider.

According to an exemplary embodiment of the invention, a computing device providing a visual collection system is provided. The computing system includes a display device, a memory, and a processor. The memory stores first and second computer programs. The processor is configured to execute the first and second computer programs. The first computer program is configured to display a menu on a display screen of the display device and display a summary on the screen that can be reached directly from the menu. The summary displays patient account information of a plurality of patient accounts for a selected one of a plurality of available clients, wherein the displayed patient account information includes a plurality of displayed entries, where each entry includes a first field indicating an account number of one of the patient accounts, a second field indicating a status associated with the account number, and a third field indicating a due date. The second computer program is configured to initially cause the third field to display a due date for submitting a claim associated with the account number to insurance when the status indicates the claim needs to be submitted. the second computer program is further configured to dynamically update the third field to display a due date for appealing denial of the claim upon determining that the status has changed to indicate that the claim was submitted and denied by the insurance.

According to an exemplary embodiment of the invention, a method for providing patient information is provided. The method includes displaying a menu on a screen of a display device and displaying a summary on the screen that can be reached directly from the menu. The summary displays patient account information of a plurality of patient accounts for a selected one of a plurality of available clients, wherein the displayed patient account information includes a plurality of displayed entries, where each entry includes a first field indicating an account number of one of the patient accounts, a second field indicating a status associated with the account number, and a third field indicating a due date. The displaying of the summary includes causing the third field to display a due date for submitting a claim associated with the account number to insurance when the status indicates the claim needs to be submitted and dynamically updating the third field to display a due date for appealing denial of the claim upon determining that the status has changed to indicate that the claim was submitted and denied by the insurance.

According to an exemplary embodiment of the invention, a computing device for providing a visual collection system is provided. The computing device includes a display device, a memory storing a computer program, and a processor configured to execute the computer program. The computer program is configured to display a first menu on a display screen of the display device for one of a plurality of patient accounts and display selectable options on the screen that can be reached directly from the first menu. Selection of a first one of the selectable options causes display of a second menu on the display screen enabling a user to enter information indicating a claim of the one patient account was denied by insurance. Selection of a second one of the selectable options causes display of a third menu on the display screen that enables the user to enter information indicating the denied claim is being appealed. Selection of the third option causes display of a fourth menu on the display screen including a list to enable selection of one of a plurality of letter types and a fourth selectable option. Selection of the fourth option causes display of a fifth menu on the display screen including a non-editable portion pre-filled with a destination address of the insurance, an editable portion for entering text in support of the appeal, and a fifth selectable option whose selection saves an in-progress copy including the portions.

BRIEF DESCRIPTION OF THE SEVERAL VIEWS OF THE DRAWINGS

Exemplary embodiments of the invention can be understood in more detail from the following descriptions taken in conjunction with the accompanying drawings in which:

FIG. 7A1-3 illustrates a Collections Process that may be executed by the VCS according to an exemplary embodiment of the present invention;

FIG. 7B1-3 illustrates a Web Claim Search Process that may be executed by the VCS according to an exemplary embodiment of the present invention;

FIGS. 20A-C illustrates a graphical user interface according to an exemplary embodiment of the invention that may be used to access information on patient accounts;

FIGS. 21A-C illustrates a graphical user interface according to an exemplary embodiment of the invention that may be used to access information on patient accounts;

FIGS. 22A-C illustrates a graphical user interface according to an exemplary embodiment of the invention that may be used to access information on patient accounts;

FIGS. 23A-B illustrates a graphical user interface according to an exemplary embodiment of the invention that may be used to manage appeal of denied claims;

FIGS. 24A-B illustrates a graphical user interface according to an exemplary embodiment of the invention that may be used to manage appeal of denied claims;

FIGS. 25A-B illustrates a graphical user interface according to an exemplary embodiment of the invention that may be used to manage appeal of denied claims;

FIG. 26 illustrates a graphical user interface according to an exemplary embodiment of the invention that may be used to manage appeal of denied claims;

FIGS. 27A-B illustrates a graphical user interface according to an exemplary embodiment of the invention that may be used to manage appeal of denied claims;

FIGS. 28A-B illustrates a graphical user interface according to an exemplary embodiment of the invention that may be used to manage appeal of denied claims;

FIGS. 29A-B illustrates a graphical user interface according to an exemplary embodiment of the invention that may be used to manage appeal of denied claims;

FIGS. 30A-B illustrates a graphical user interface according to an exemplary embodiment of the invention that may be used to manage appeal of denied claims;

FIG. 31A-B illustrates a graphical user interface according to an exemplary embodiment of the invention that may be used to manage appeal of denied claims;

FIG. 32 illustrates a graphical user interface according to an exemplary embodiment of the invention that may be used to manage appeal of denied claims.

DETAILED DESCRIPTION

Figure 1A:
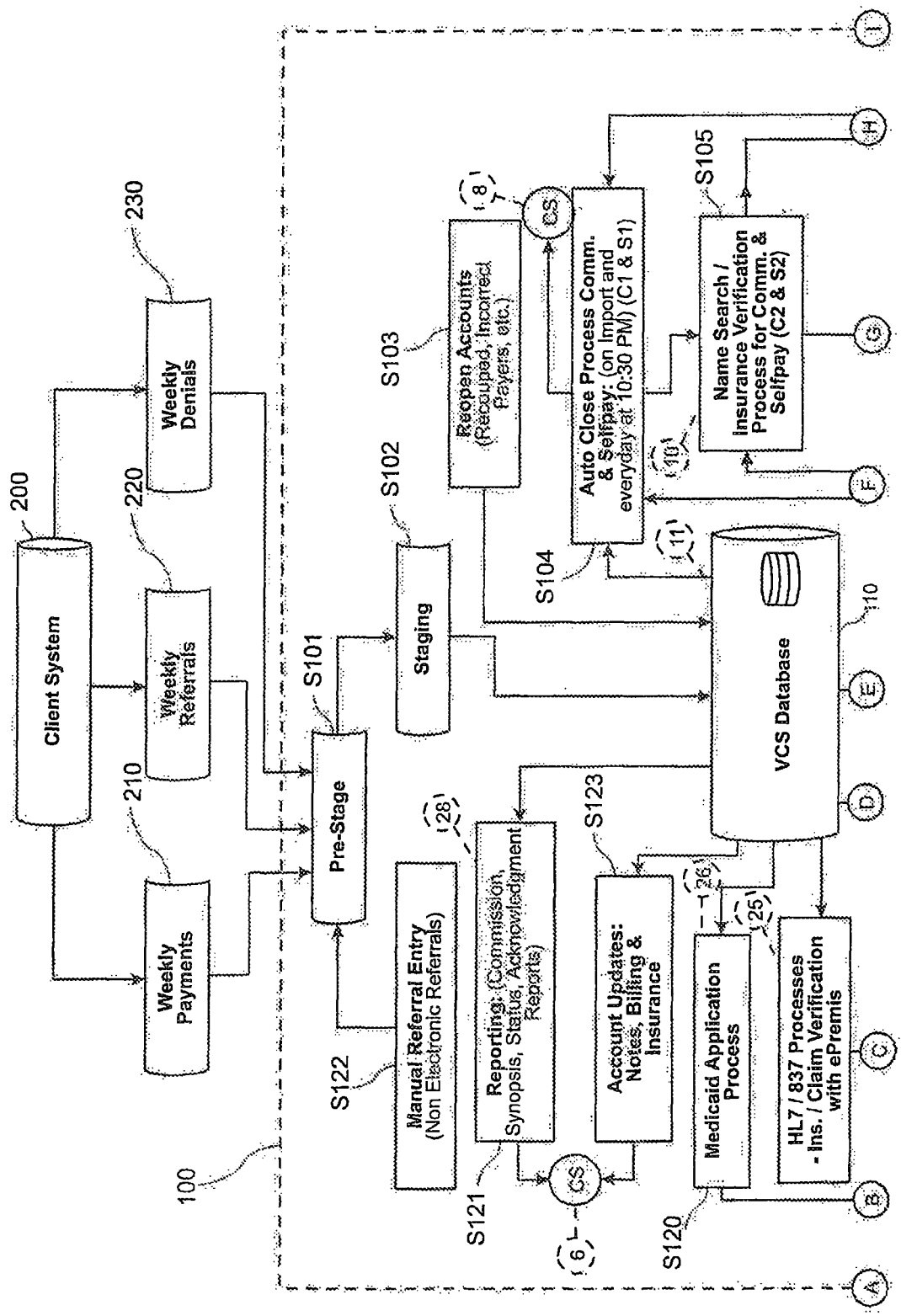
FIG. 1A-B illustrates a workflow for a Visual Collections System (VCS) according to an exemplary embodiment of the present invention.

One or more embodiments of the present disclosure include an improved user interface for collection based on patient services provided by a healthcare provider. The user interface allows users to more quickly and efficiently access patient data in patient accounts. In particular, one or more embodiments of the user interface enables users to quickly access the patient accounts having claims that need to be submitted to insurance and the denied claims that need to be appealed. Further, one or more embodiments of the user interface enables user to quickly determine the due dates for submitting these claims and the due dates for appealing the denied claims to ensure that these claims are submitted in a timely fashion, thereby recapturing revenue that would otherwise be lost due to failure to submit a claim or appeal a denied claim. For example, one or more embodiments of the present disclosure include a user interface that presents information on a patient account along with a dynamic due date that initially displays a due date for submitting a claim associated with the patient account when a status associated with the claim indicates the claim needs to be submitted to insurance, but then updates to display a due date for appealing denial of the claim upon determining that the status has changed to indicate that the claim was submitted but denied by the insurance. Further, this dynamic field can update to indicate the deadline for submitting the claim or appealing the denied claims has past. Thus, an investigator can use a single menu and a single field within that menu, without opening additionally menus, and with minimal selections within the single menu to efficiently determine whether it is necessary to begin performing first work required for submitting a claim, determine whether it is too late to begin this first work so another claim or appeal can be worked on, determine whether the claim was submitted and denied, determine whether it is necessary to begin performing second work required for appealing the denied claim, and to determine whether it is too late to begin this second work so another claim or appeal can be worked on.

The inventive concept will now be described in more detail with reference to the accompanying drawings, where exemplary embodiments of the present disclosure have been illustrated. Throughout the drawings, same or like reference numerals are used to represent the same or like components.

Figure 1B:
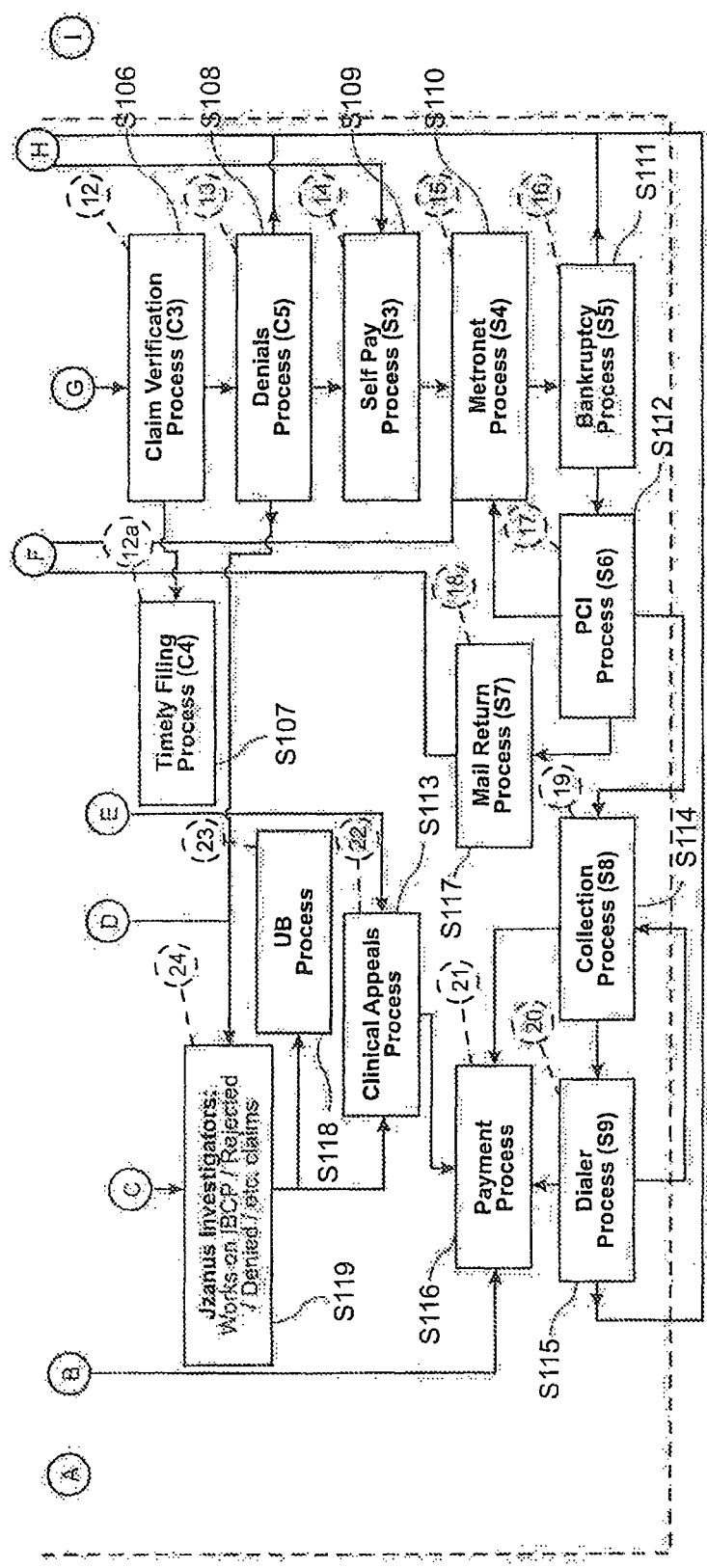

FIG. 1A-B illustrates a workflow (e.g., All Process Workflow) of the Visual Collections System according to exemplary embodiment of the invention. The Visual Collections System 100 receives data from a Client System 200 (e.g., a computer system of a hospital) to process. For example, the data is received in an electronic file having formats such as CSV, HL7, 835, 837, DAT, GNR, and RPT. The received data includes Weekly Payments 210, Weekly Referrals 220, and Weekly Denials 230.

The Weekly Payments 210 is an electronic file (e.g., a payment file) that is received weekly. In an embodiment, the payment file includes the Patient Account number (e.g., a unique number that distinguishes the account of one patient from the accounts of other patients), Visit information, Amount Paid, a claim number (e.g., each service provided may have its own claim number), a check date, a claim process date, and a denial reason if the claim was denied. The Weekly Referrals 220 is an electronic file (e.g., electronic referral file) that is received weekly. The electronic referral file has patient account information including Patient Demographic information, Guarantor's Demographic information, Patient Insurance Information, Attending Physician Notes, Diagnosis Information, Charges, etc. The Weekly Denials 230 is an electronic file received weekly, which has information about a claim of a patient that was denied by an insurance company. The Denial Codes and Insurance companies are mapped with some automated actions, which the system initiates once it determines which insurance company the denial code maps to.

Figure 2A:
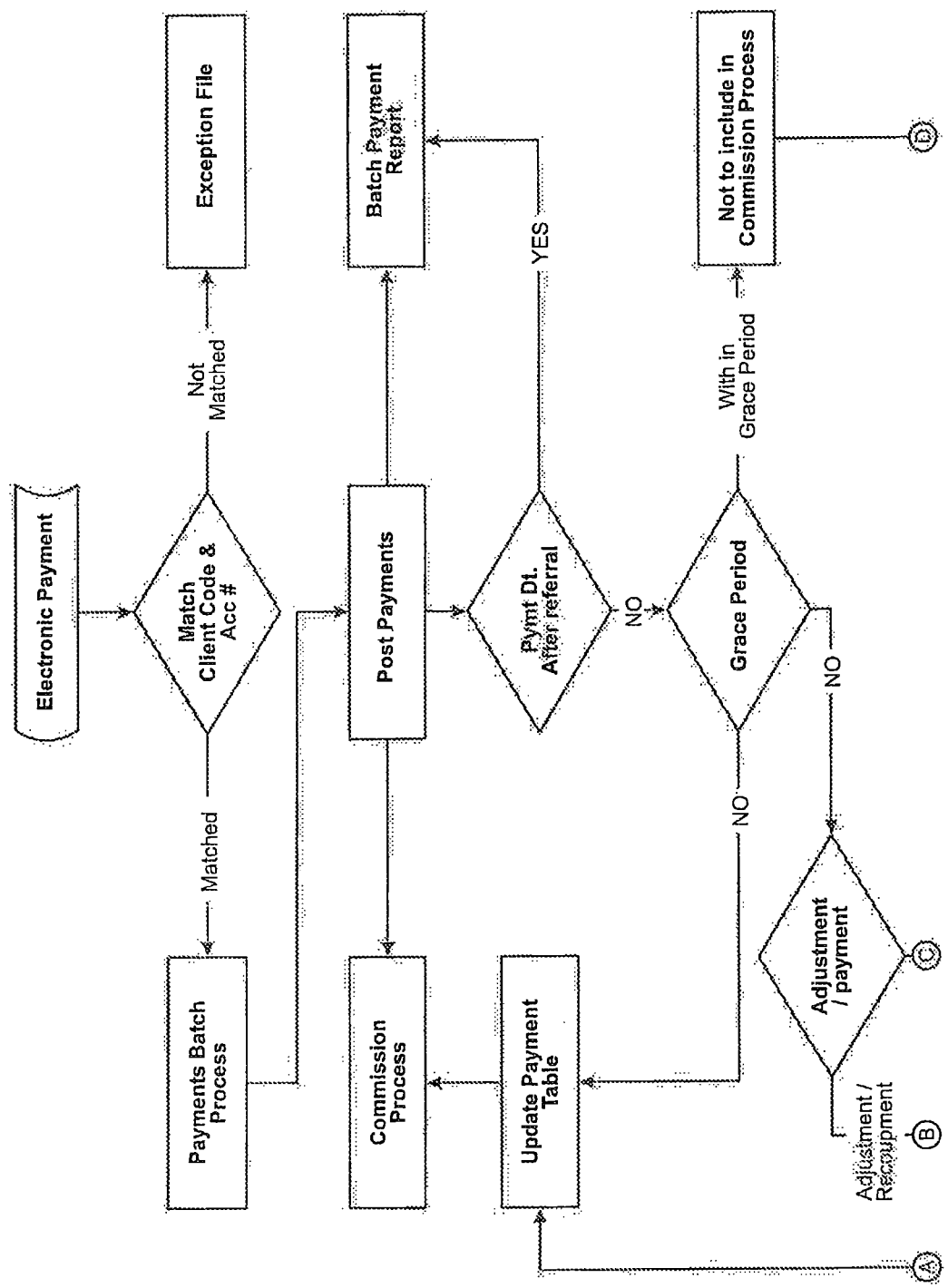
FIG. 2A-B illustrates a payment process that may be executed by the VCS according to an exemplary embodiment of the present invention.
Figure 2B:
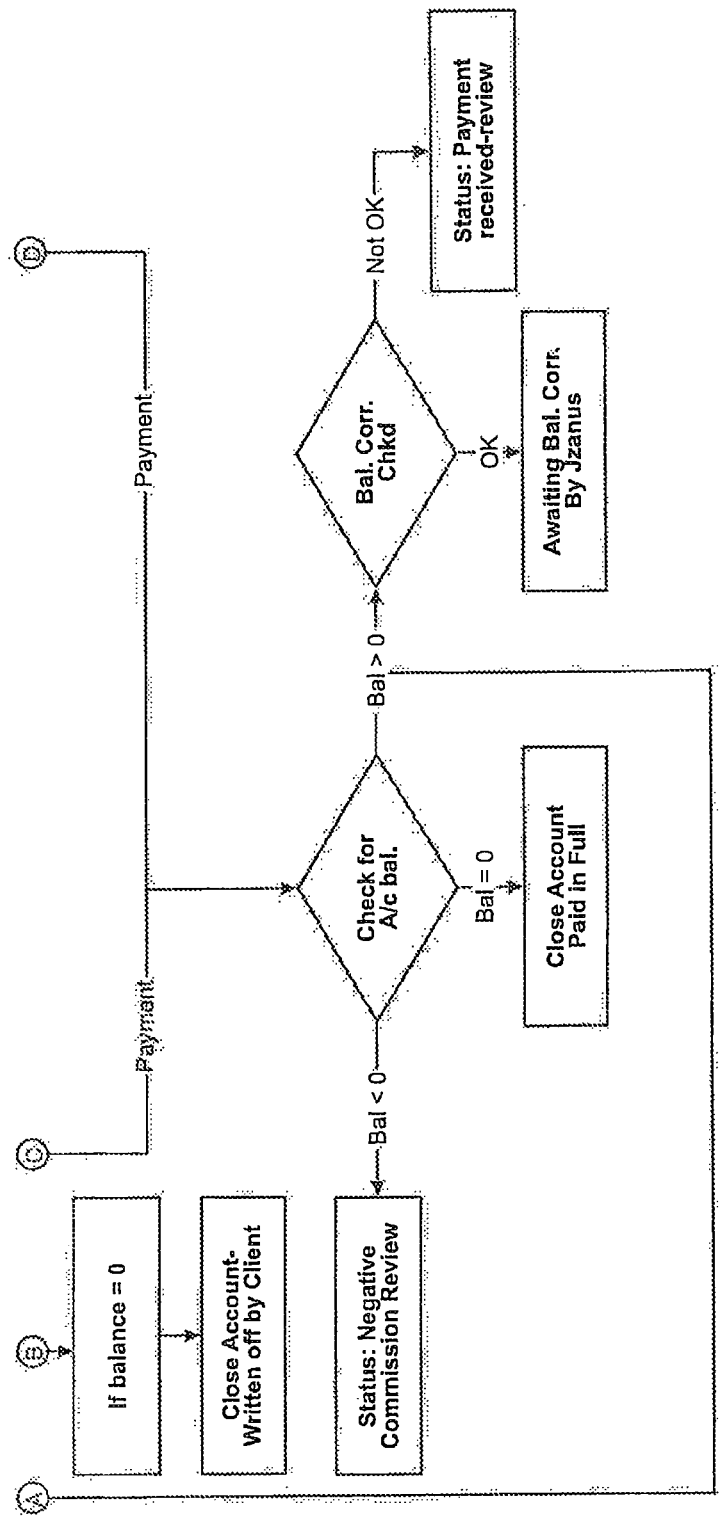
Figure 3A:
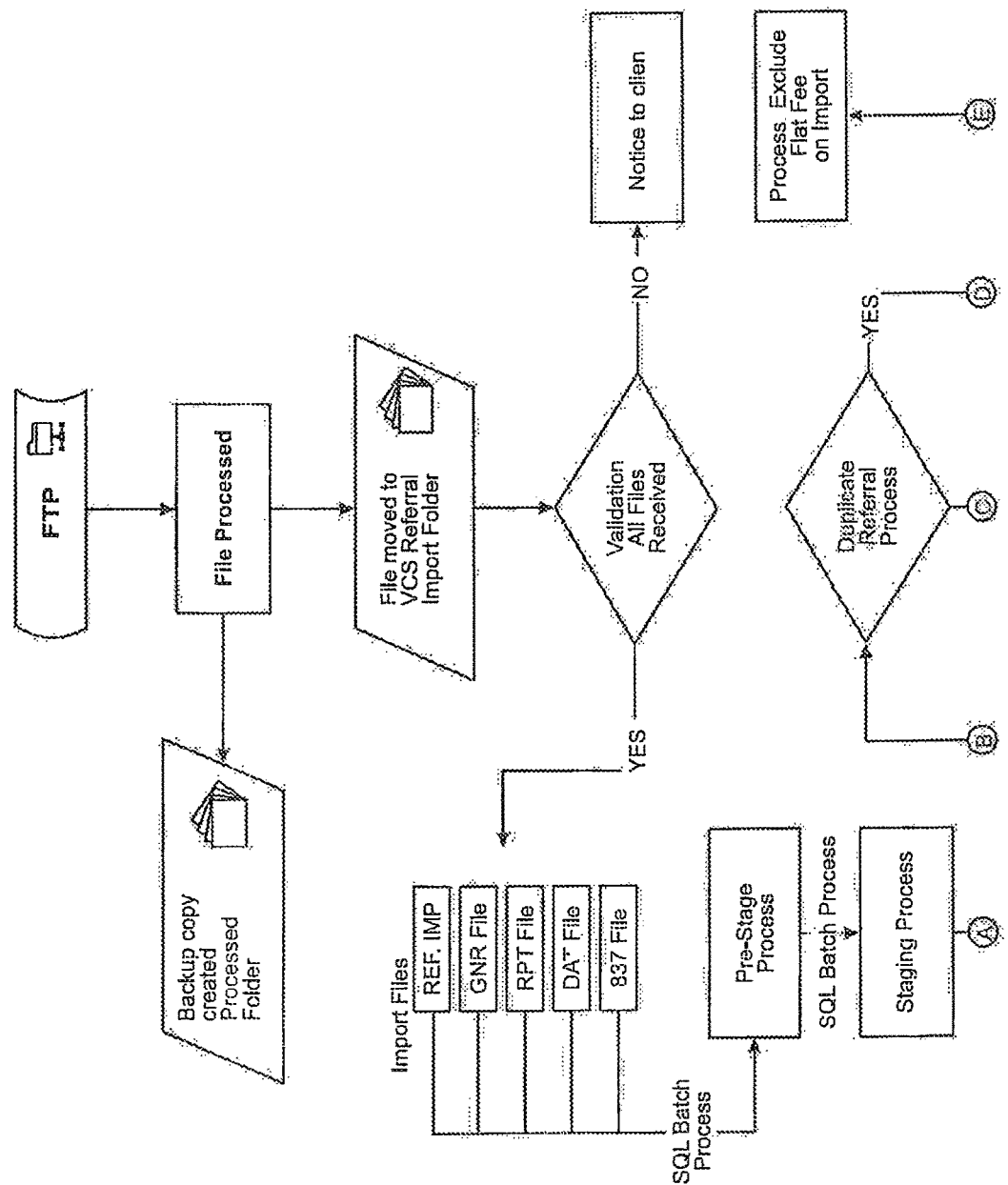
FIG. 3A-B illustrate a import process for importing data (e.g., client accounts, claims, etc.) into the VCS according to an exemplary embodiment of the present invention.
Figure 3B:
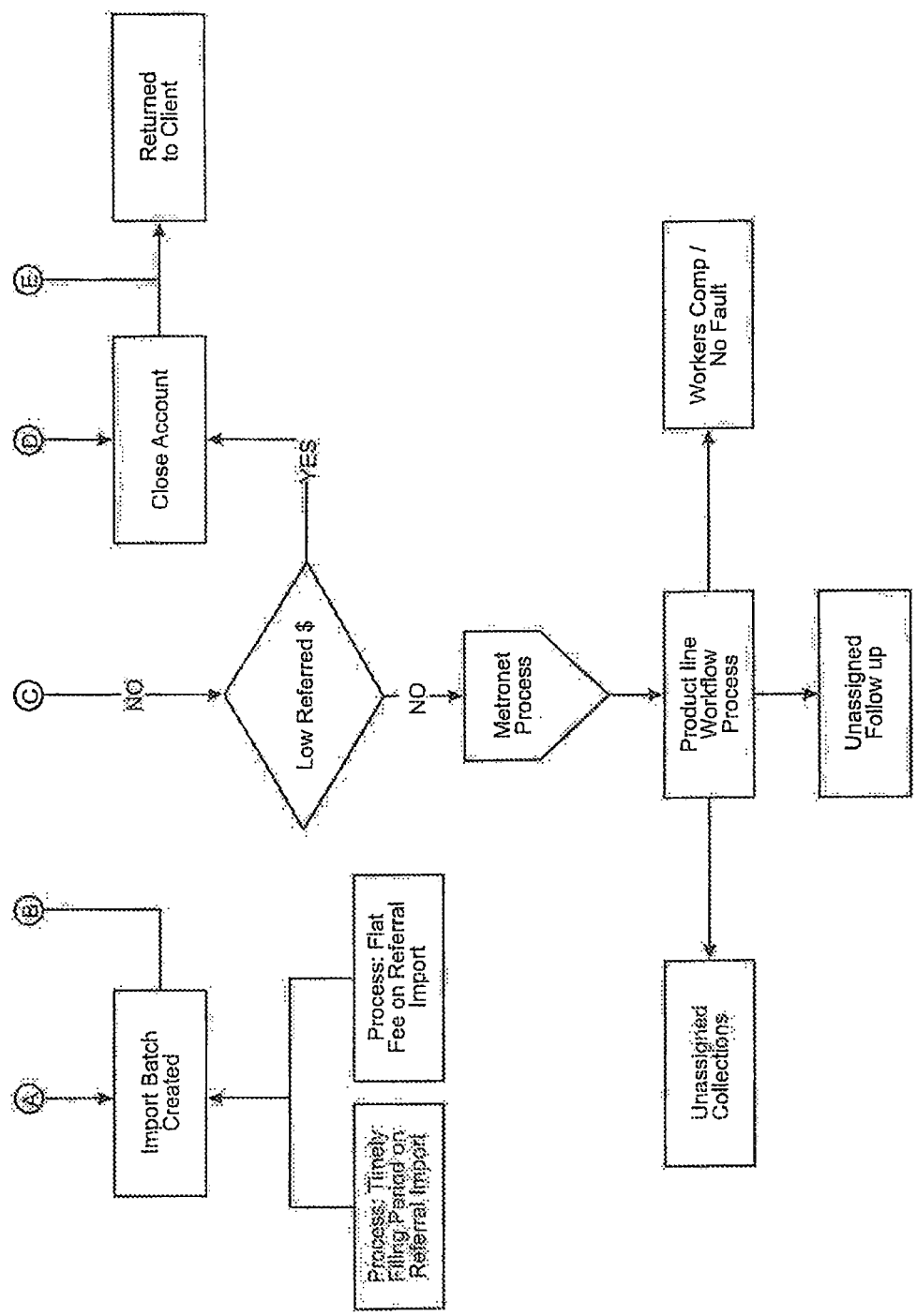
Figure 4A:
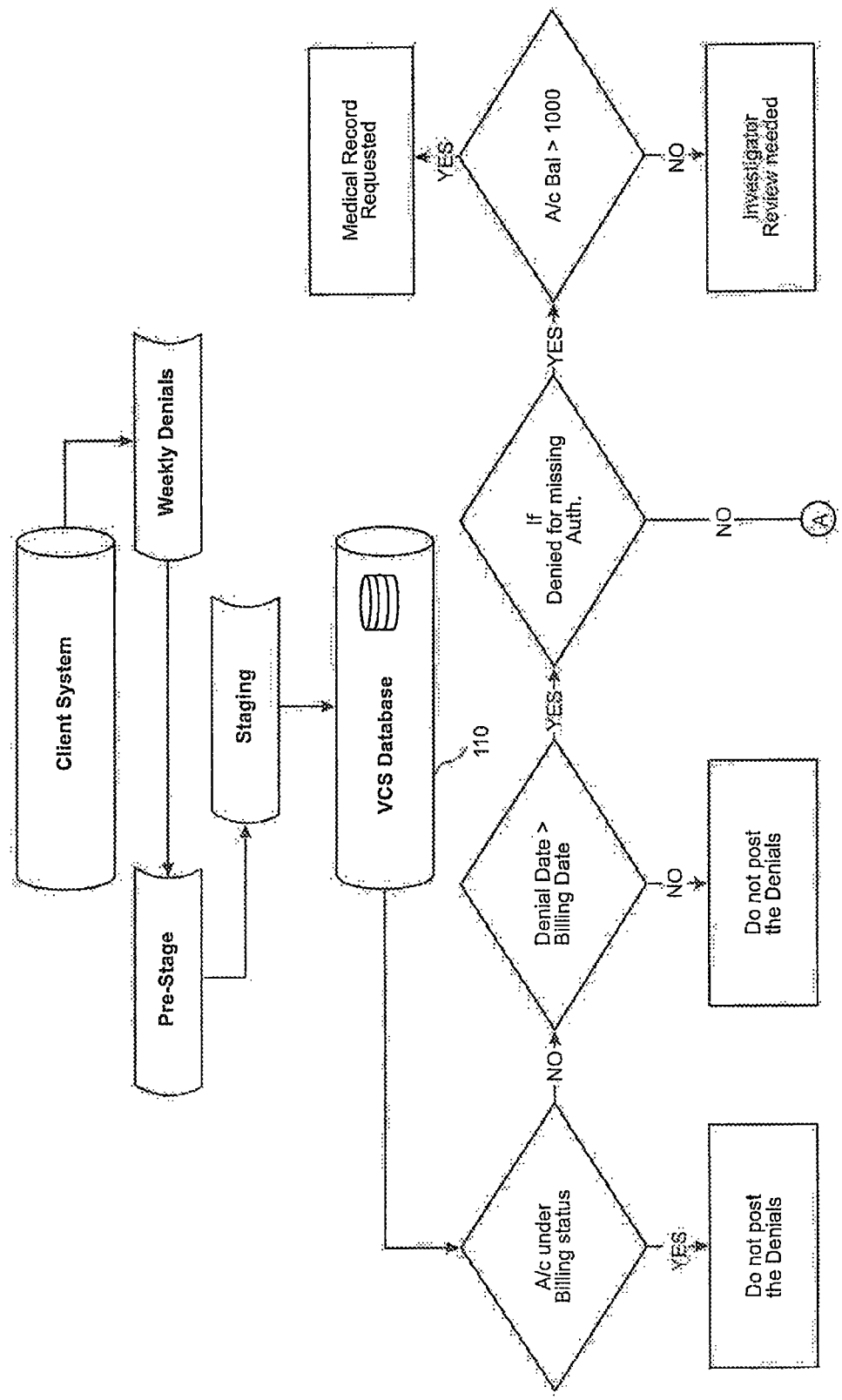
FIG. 4A-B illustrates a denial workflow that may be executed by the VCS according to an exemplary embodiment of the present invention.
Figure 4B:
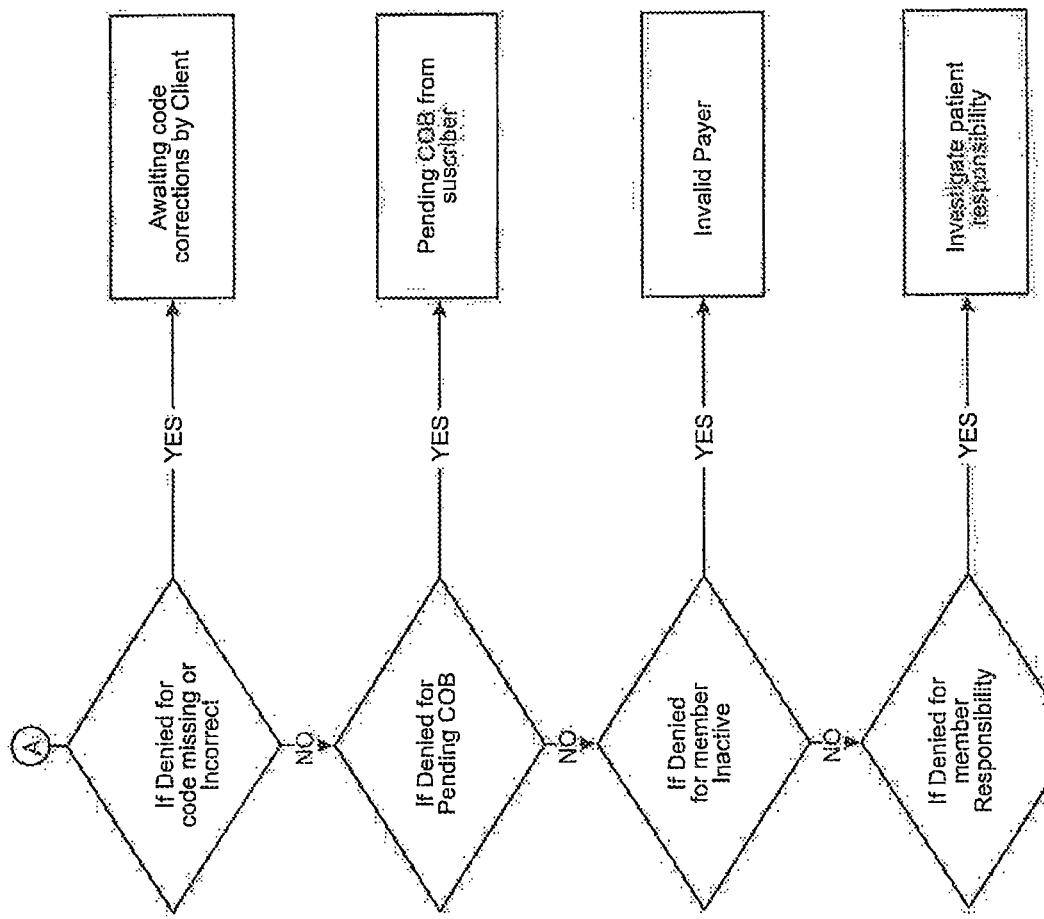

Visual Collections System 100 performs a pre-stage process (e.g., preprocessing) on the received data (S101). This process pulls all the data from a client's file into an internal file having an internal proprietary format. The data of the internal file is then split and saved into different tables (e.g., pre-staged tables). The data is stored permanently. This process may execute one or more sub-processes. For example, the process may execute a payment workflow on the Weekly Payments 210, a referral import workflow on the Weekly Referrals 220, and a referral denial workflow on the Weekly Denials 230. The payment workflow will be discussed later in more detail with respect to FIG. 2A-B. The referral import workflow will be discussed in more detail with respect to FIG. 3A-B. The referral denial workflow will be discussed in more detail with respect to FIG. 4A-B. The referral import workflow may also be performed on a manually entered referral entry.

The Visual Collections System 100 performs a staging process in which data is copied from the pre-staged tables into tables of a relational database 110 (S102).

The Visual Collections System 100 may perform a Reopen Accounts process (S103). Data representing a patient account is maintained in the system when the patient owes money to a healthcare provider (e.g., a hospital, a doctor, etc.) due to the healthcare provider providing a service to the patent, and the patient not paying the healthcare provider the full amount for the service. For example, if the full amount is a $50 dollar co-pay and the contracted reimbursement amount for the service from the health insurance company of the patient, and the patient has only paid the co-pay, the data would be present in the system. Then, after the contracted reimbursement amount is paid by the health insurance company, the data representing the patient account can be deleted. For example, the patent account can be closed. However, if the contracted reimbursement amount is recalled (recouped) by the insurance company, the reopen account process can be invoked to reopen the account. The reason for the recoupment may be due to the overpayment on a previous claim to the same patient or an inadvertent payment made by inactive insurance (claim was paid while insurance had lapsed). Investigators can review the claims of the reopened account to determine whether the recoupment was correct. If the recoupment is not correct, the claim can be resubmitted to the insurance company. If the recoupment was correct because the wrong payer was billed, the claim can be submitted to the correct payer(s).

The Visual Collections System 100 is configured to perform an Auto Close Process/Self Pay process (S104). The Auto Close Process/Self Pay process will be discussed in more detail later with respect to FIG. 5A-C.

Figure 6A:
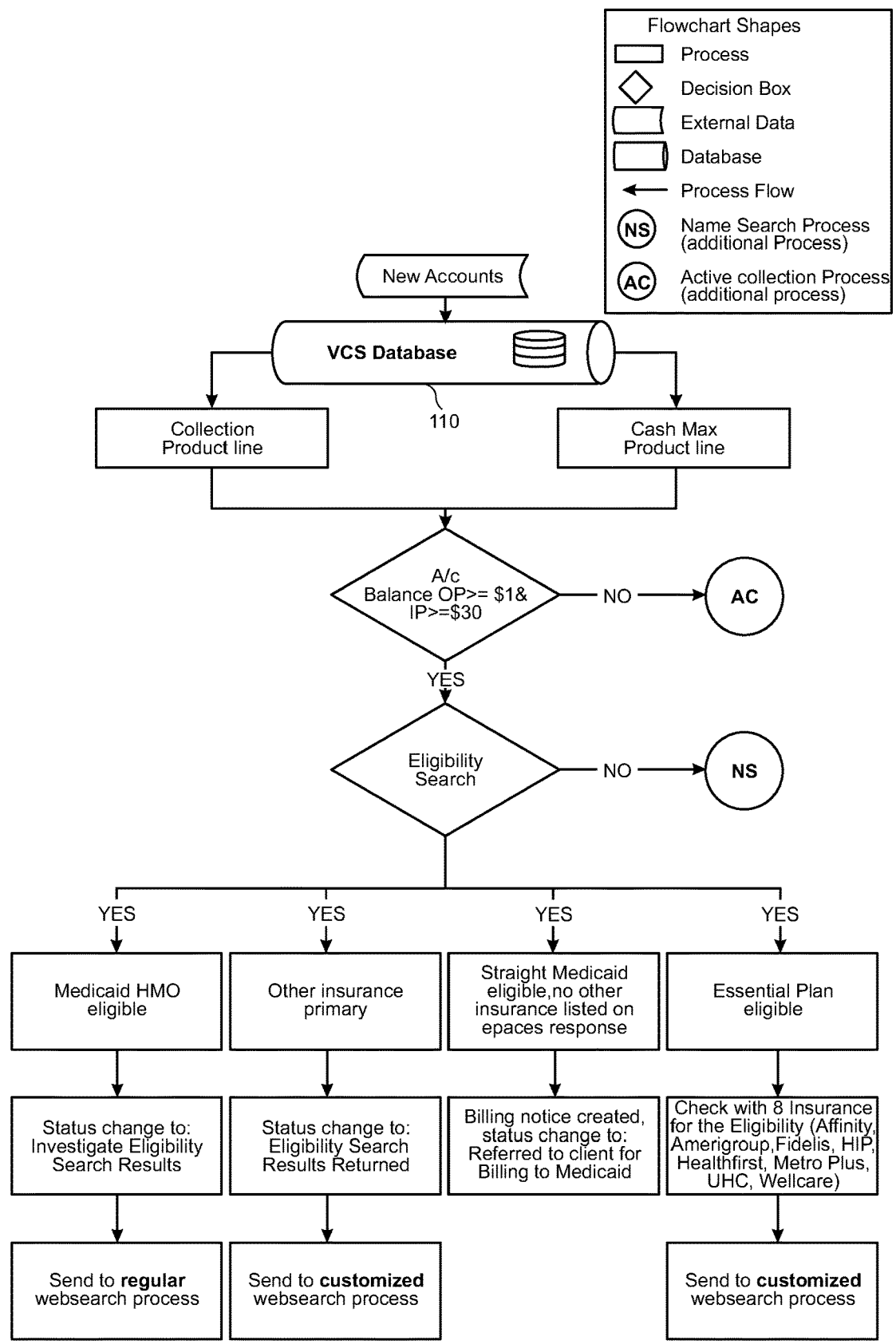
FIG. 6A illustrates a Medicaid Eligibility Search Process that may be executed by the VCS according to an exemplary embodiment of the present invention.
Figure 6B:
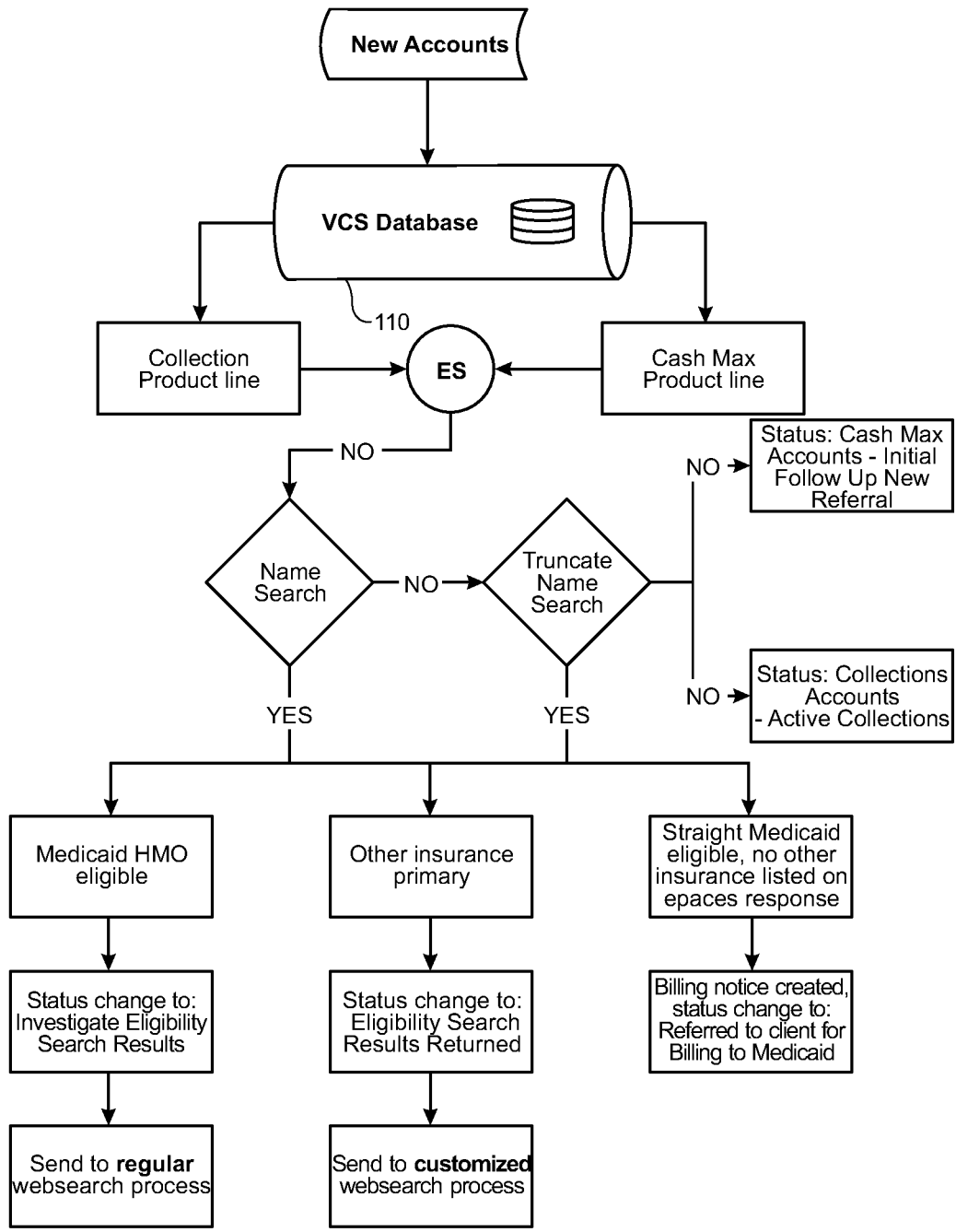
FIG. 6B illustrates a Medicaid Name Search Process that may be executed by the VCS according to an exemplary embodiment of the present invention.
Figure 6C:
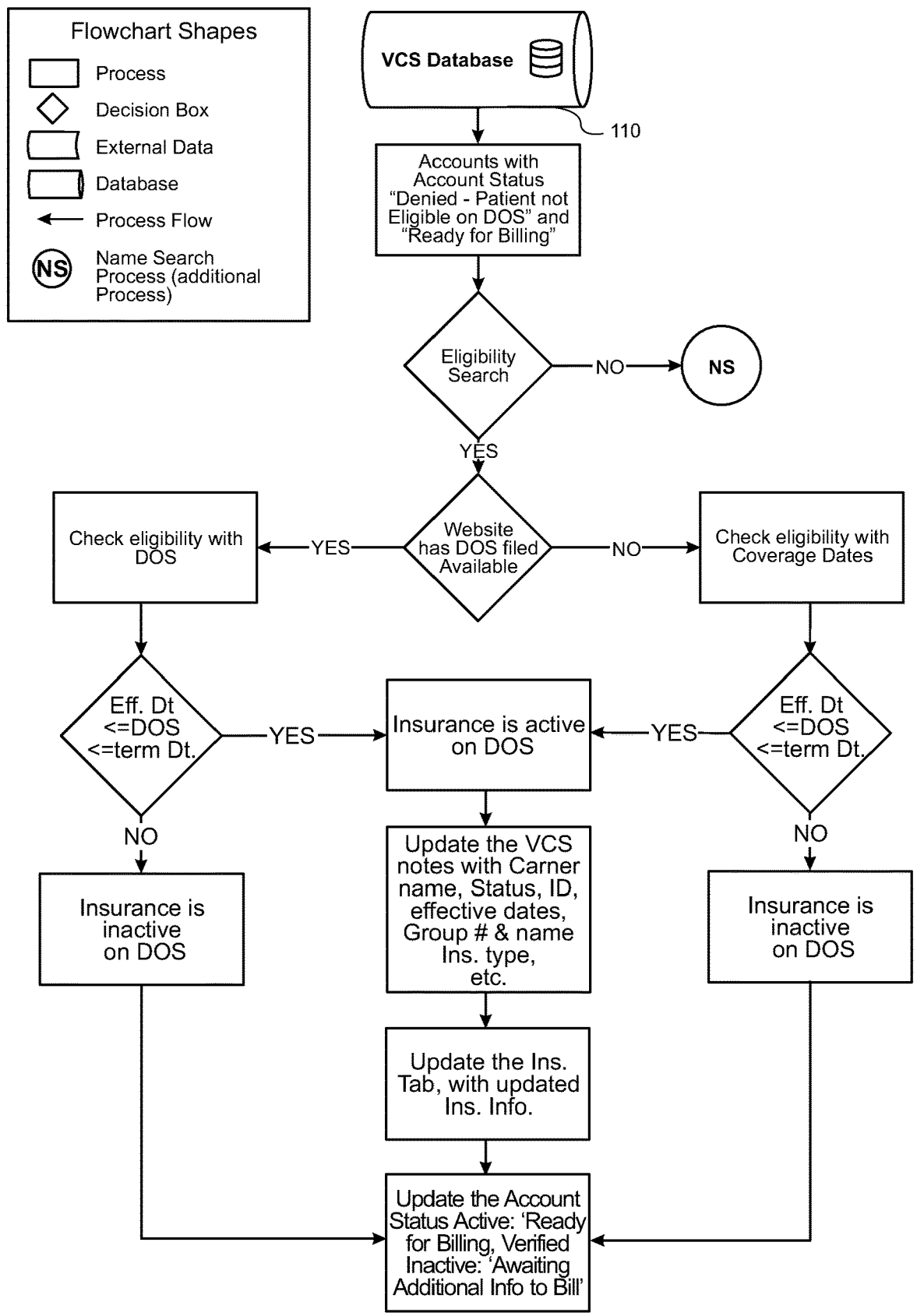
FIG. 6C illustrates an Eligibility WebSearch Process that may be executed by the VCS according to an exemplary embodiment of the present invention.

The Visual Collections System 100 is configured to perform a Name Search/Insurance Verification process (S105). The Name Search/Insurance Verification process will be discussed in more detail later with respect to FIGS. 6A, 6B, and 6C.

The Visual Collections System 100 is configured to perform a Claim Verification Process (S106). The Claim Verification Process will be discussed in more detail later with respect to FIGS. 7A and 7B.

The Visual Collections System 100 is configured to perform a Timely Filing & Due Date Process (S107). The Timely Filing & Due Date Process will be discussed in more detail later with respect to FIG. 8A-B.

The Visual Collections System 100 is configured to perform a Denials Process (S108). The Denials Process will be discussed in more detail later with respect to FIG. 9A-B.

Figure 5A:
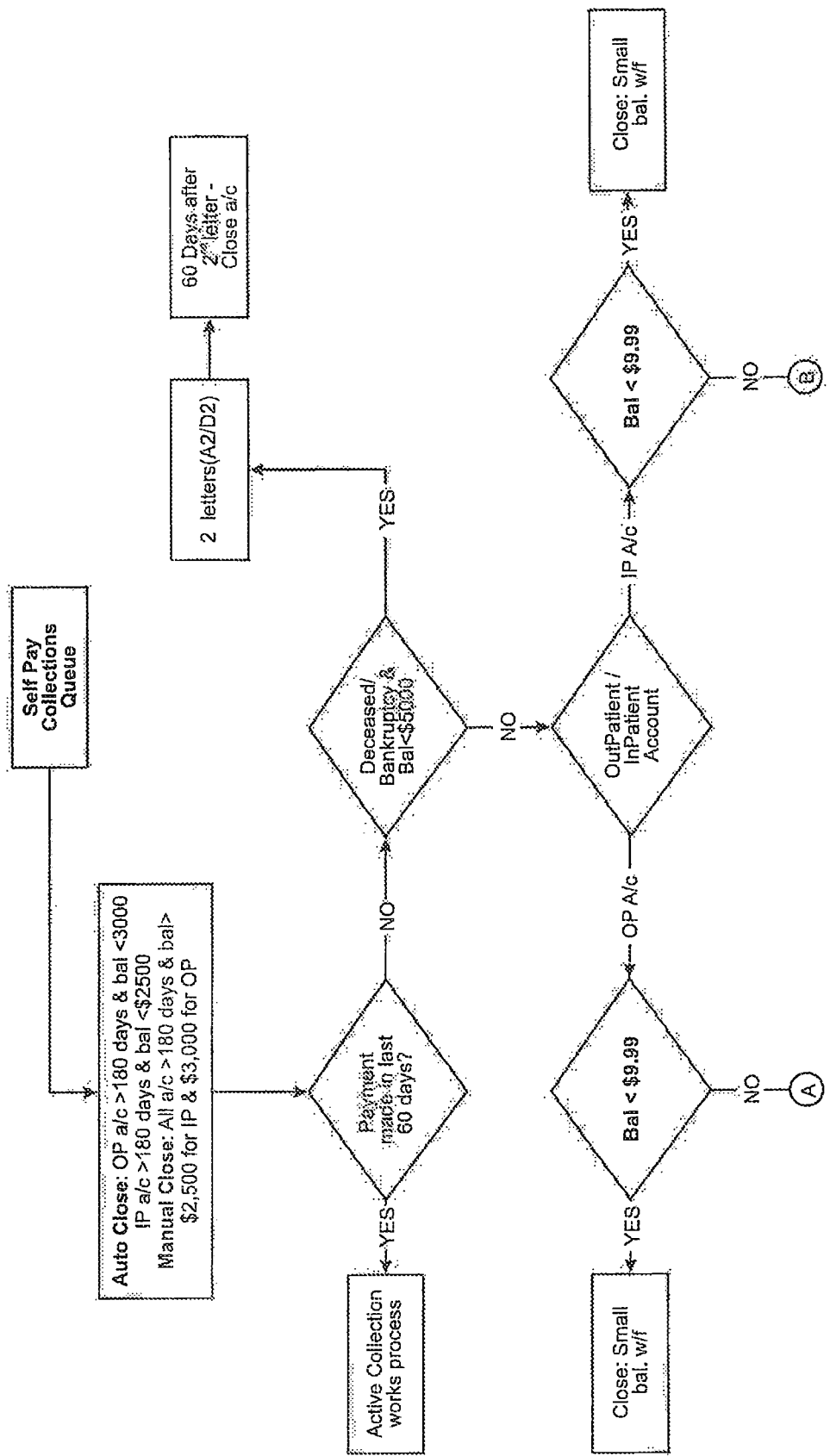
FIG. 5 illustrates an Auto Close Process and Self Pay process that may be executed by the VCS according to an exemplary embodiment of the present invention.
Figure 5B:
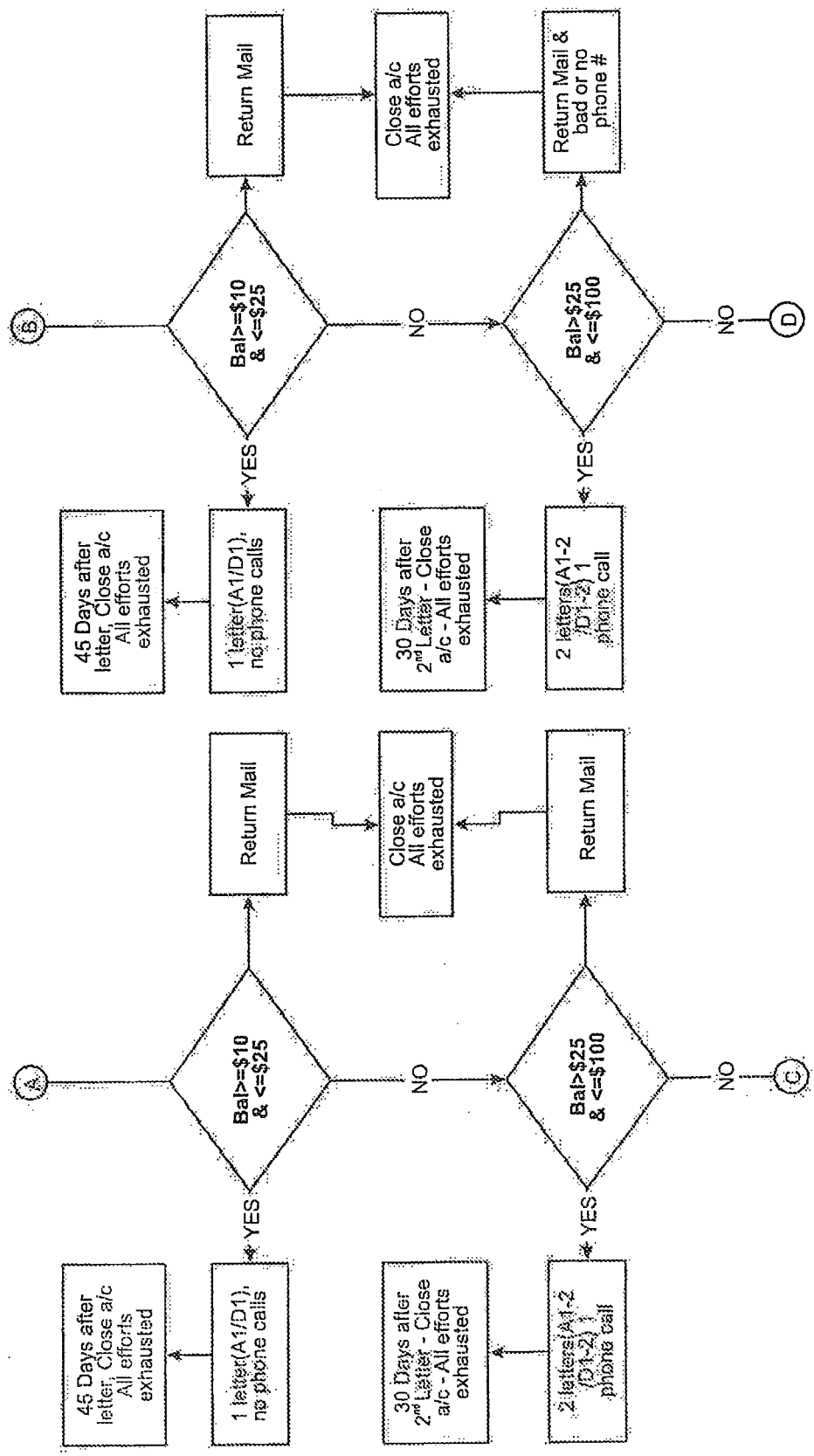
Figure 5C:
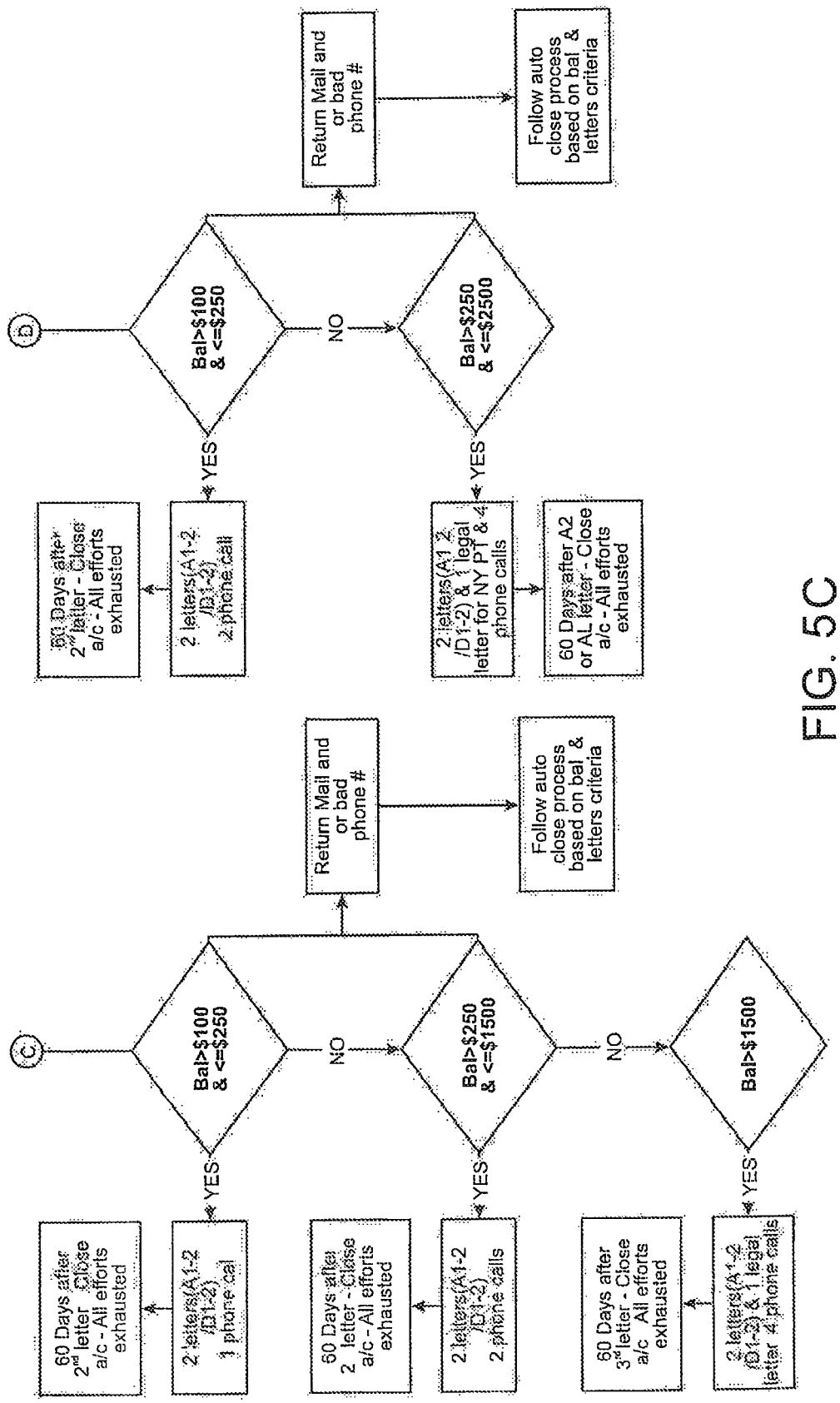

The Visual Collections System 100 is configured to perform a Self Pay Process (S109). The Self Pay Process is shown in FIG. 5A-C.

Figure 10A:
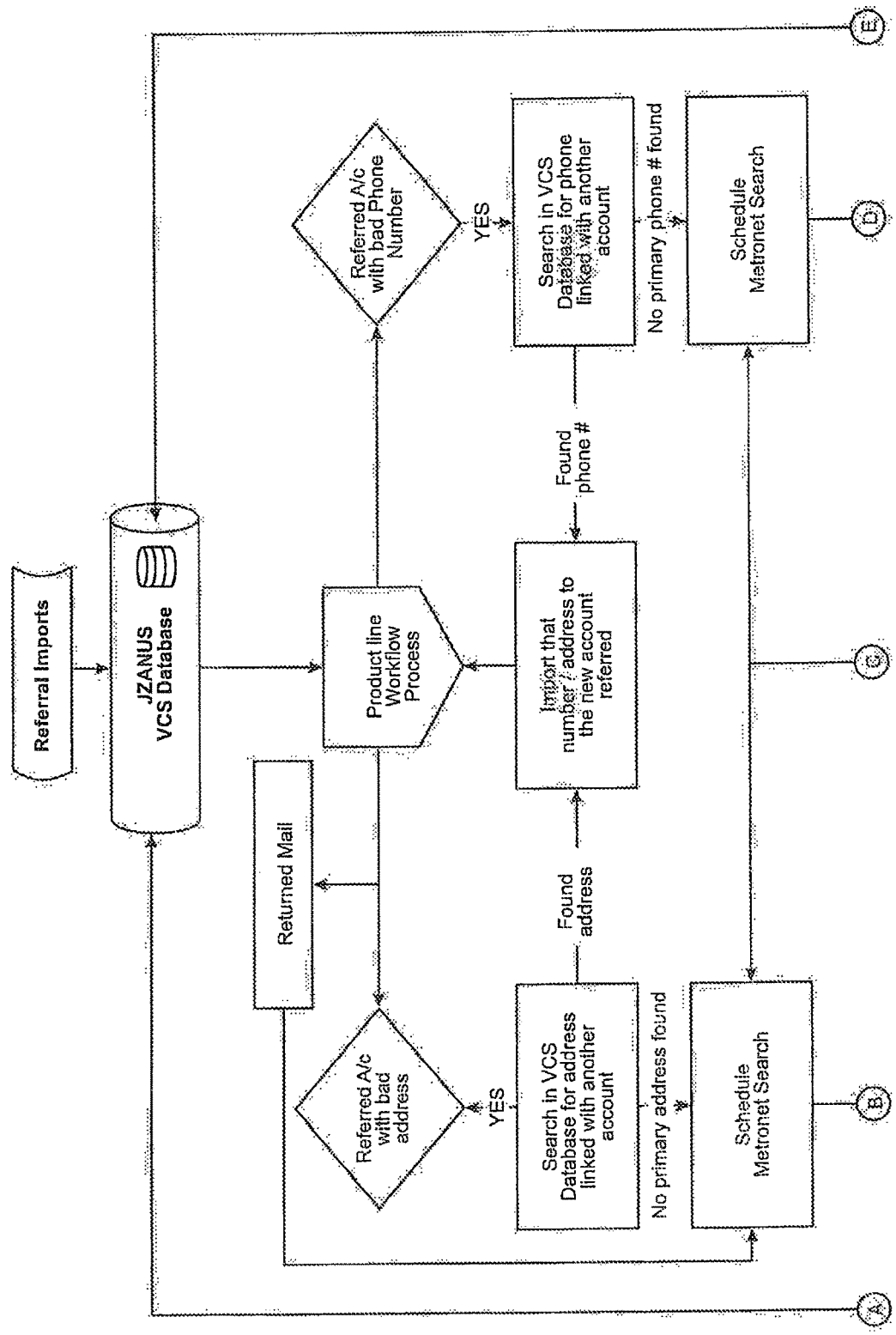
FIG. 10A-B illustrates a Metronet Process that may be executed by the VCS according to an exemplary embodiment of the present invention.
Figure 10B:
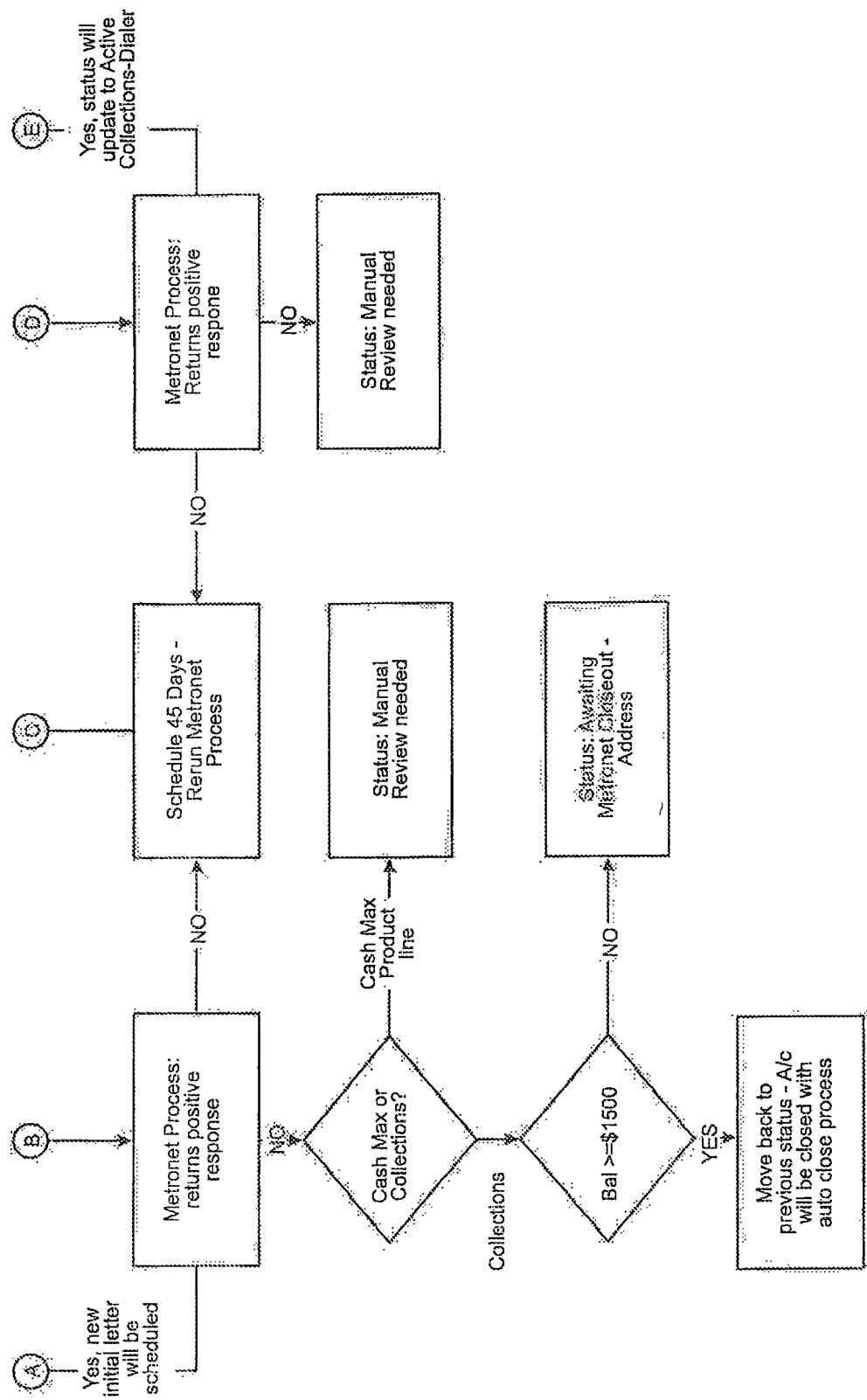

The Visual Collections System 100 is configured to perform a Metronet Process (S110). The Metronet Process will be discussed in more detail later with respect to FIG. 10A-B.

Figure 11A:
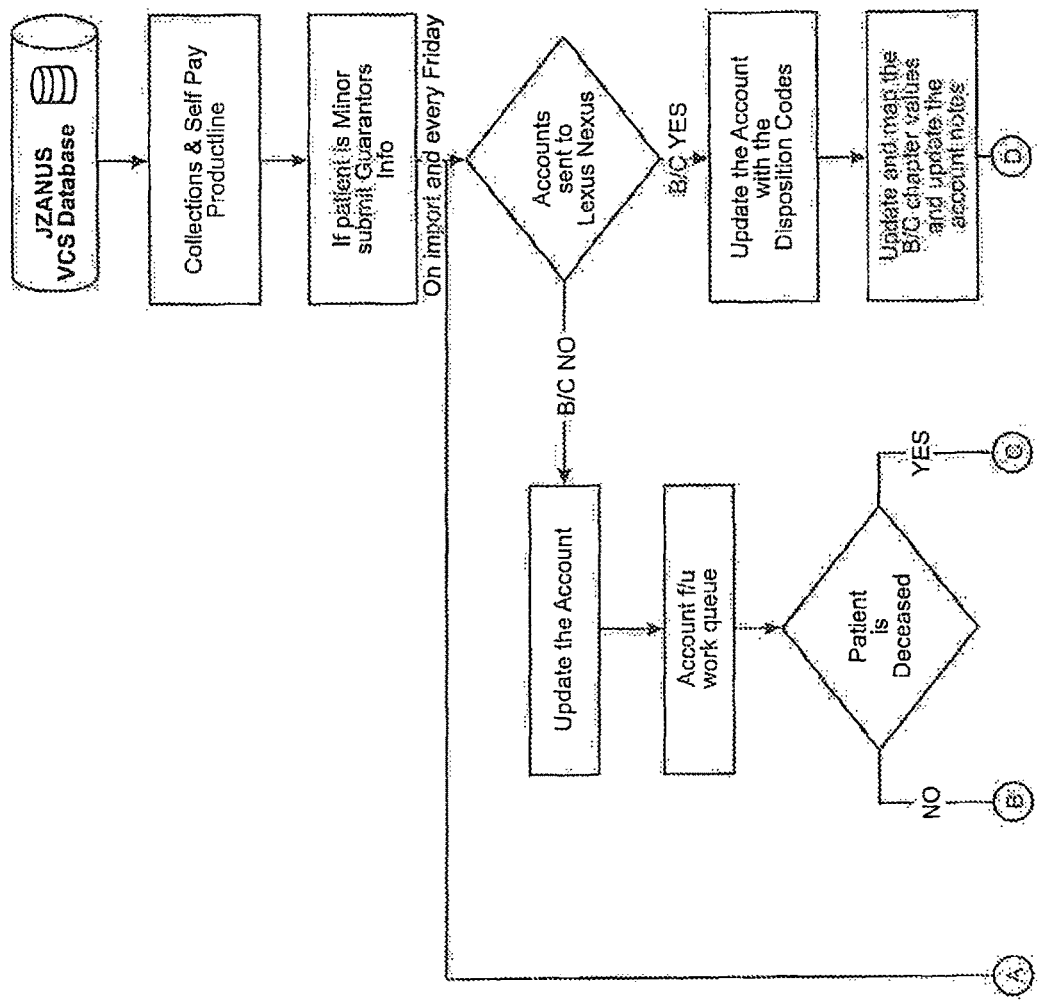
FIG. 11A-B illustrates a Bankruptcy Process that may be executed by the VCS according to an exemplary embodiment of the present invention.
Figure 11B:
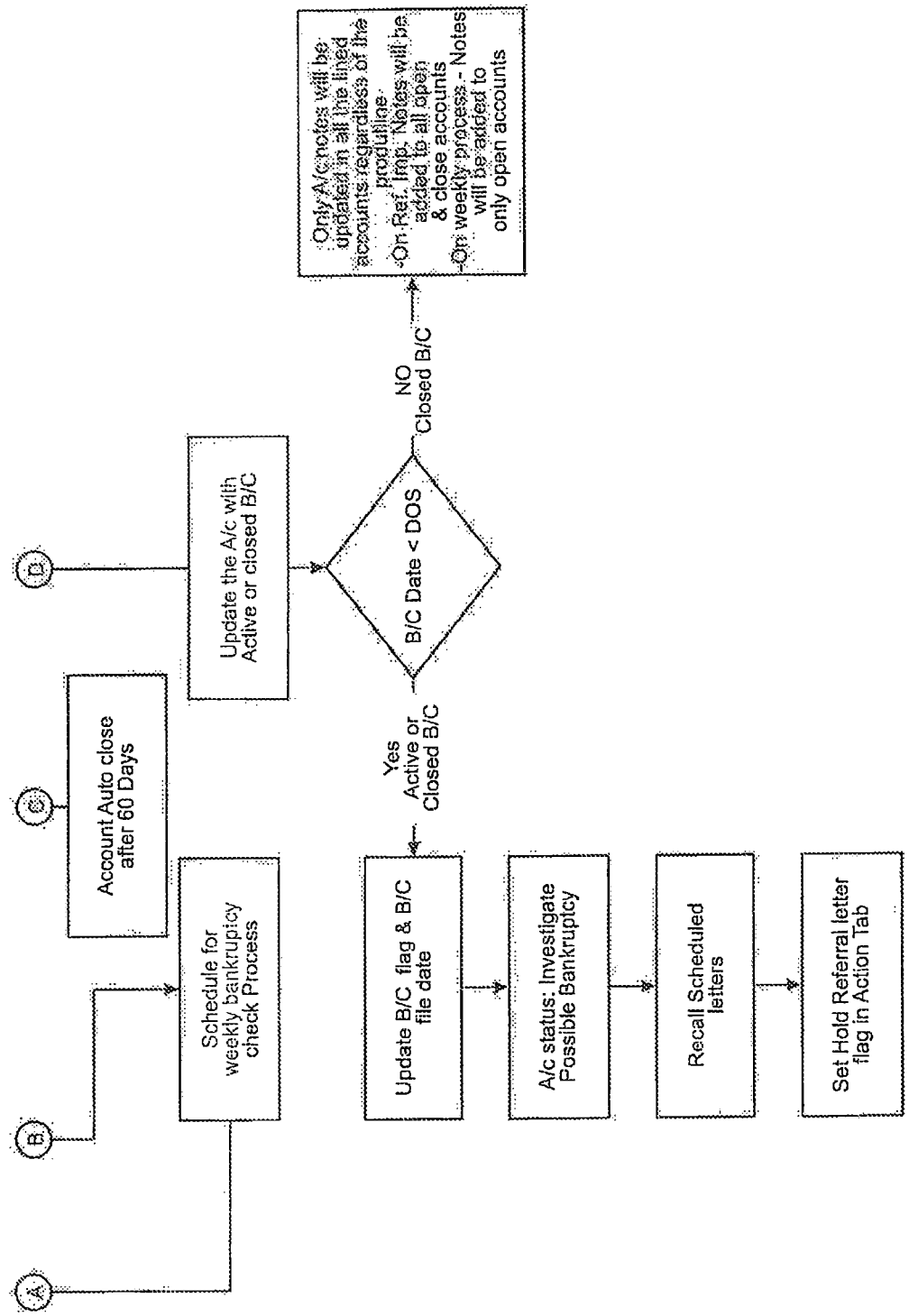
Figure 12A:
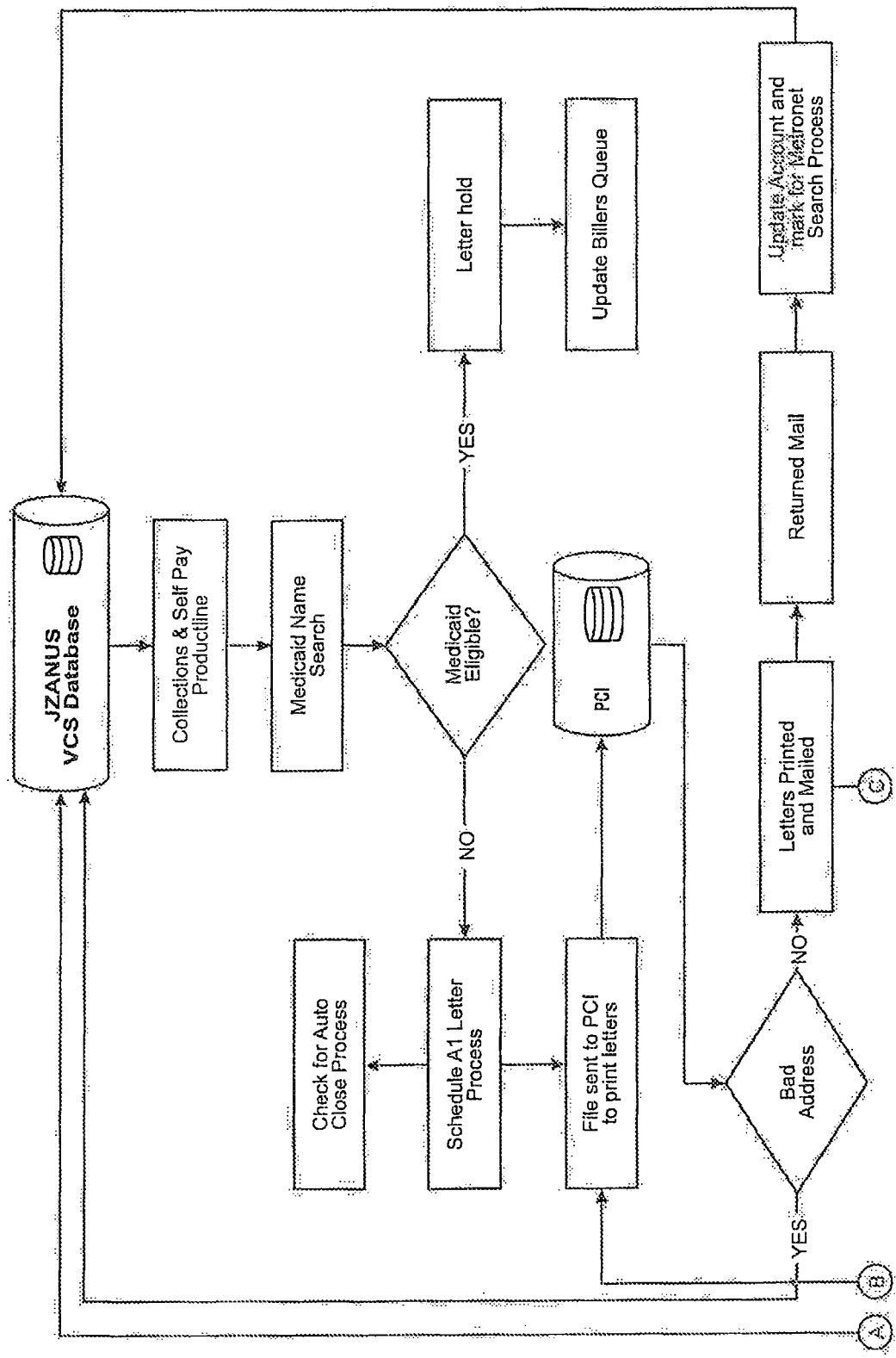
FIG. 12A-B illustrates a PCI and Mail Return Process that may be executed by the VCS according to an exemplary embodiment of the present invention.
Figure 12B:
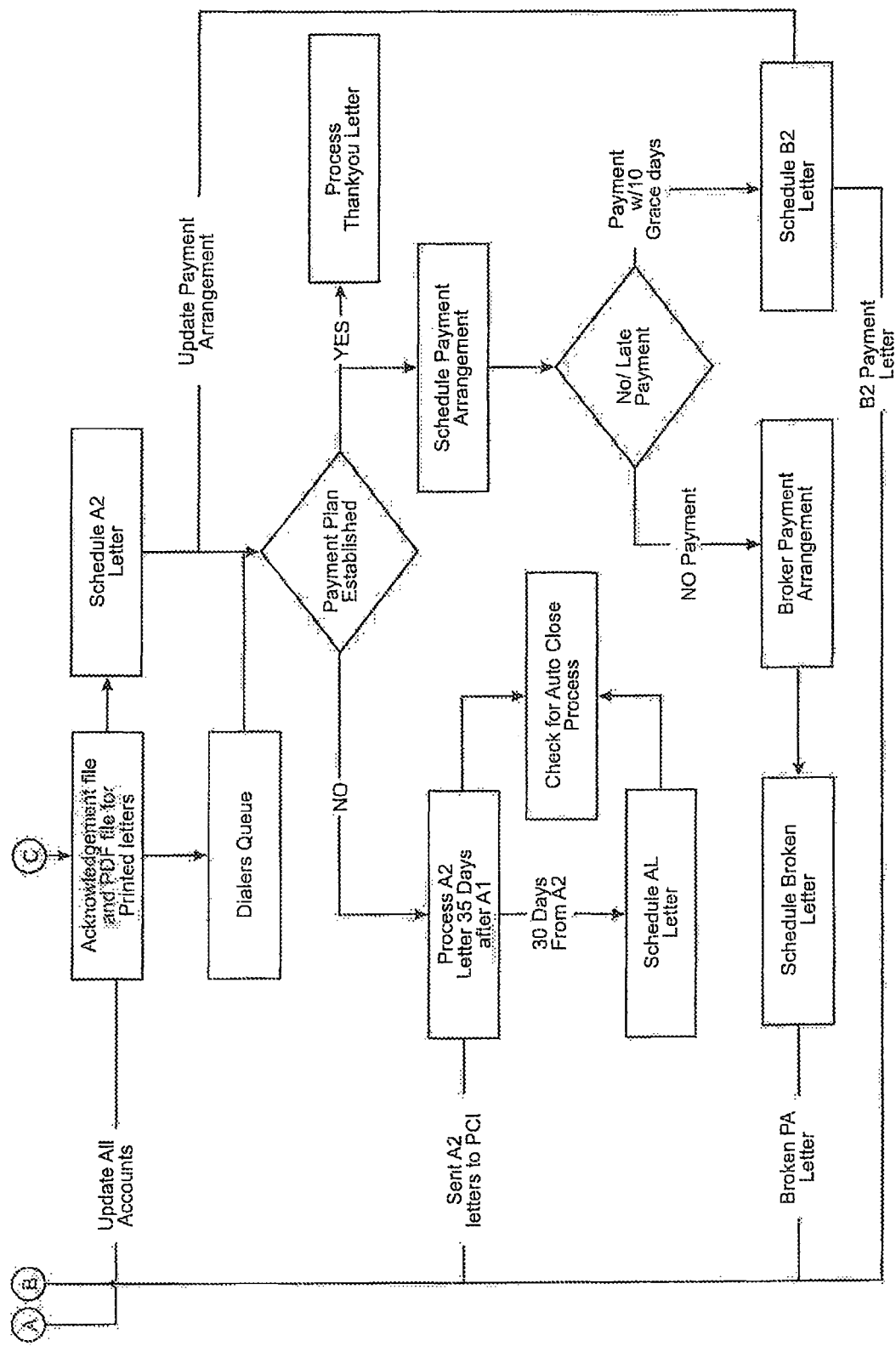

The Visual Collections System 100 is configured to perform a Bankruptcy Process (S111). The Bankruptcy Process will be discussed in more detail later with respect to FIG. 11A-B The Visual Collections System 100 is configured to perform a PCI and Mail Return Process (S112). The PCI and Mail Return Process will be discussed in more detail later with respect to FIG. 12A-B.

The Visual Collections System 100 is configured to perform a Collection Process (S114). The Collection Process is performed in FIG. 7A1-3.

Figure 13A:
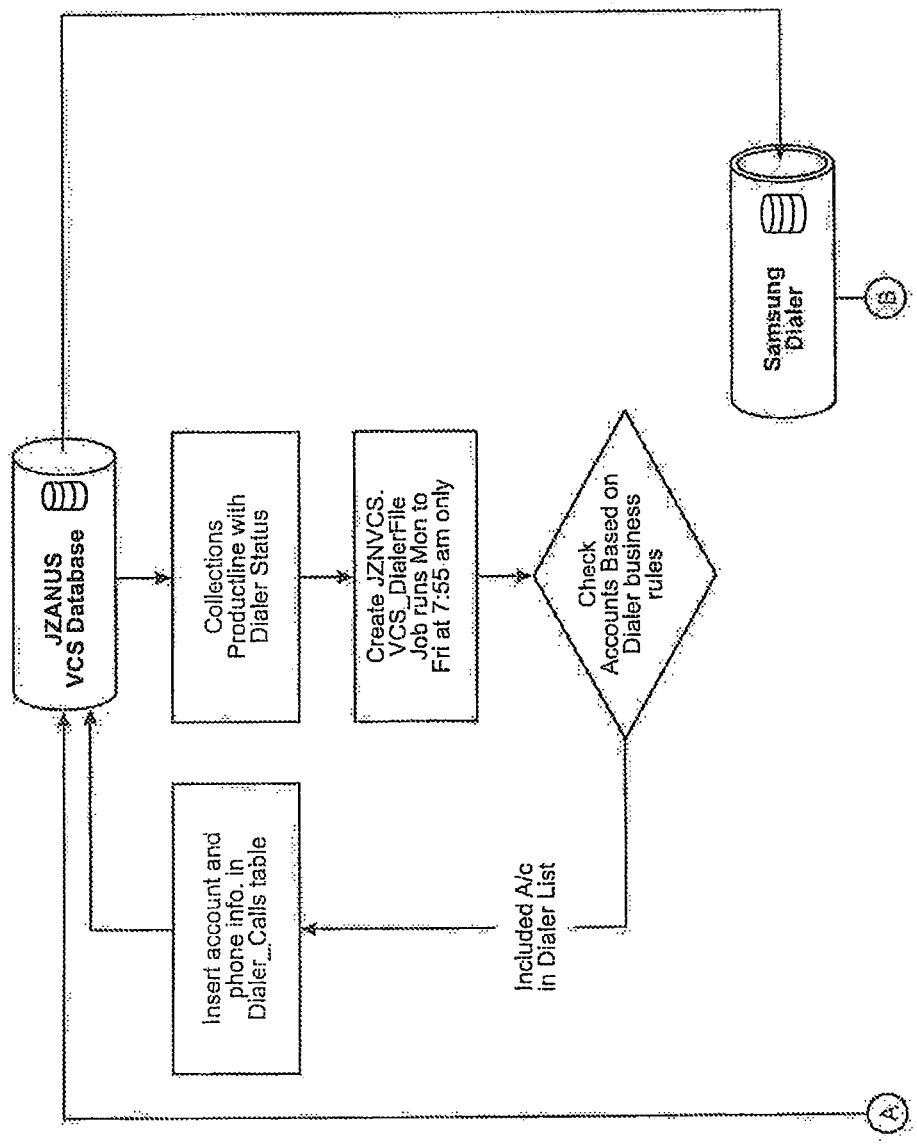
FIG. 13A-B illustrates a Dialer Process that may be executed by the VCS according to an exemplary embodiment of the present invention.
Figure 13B:
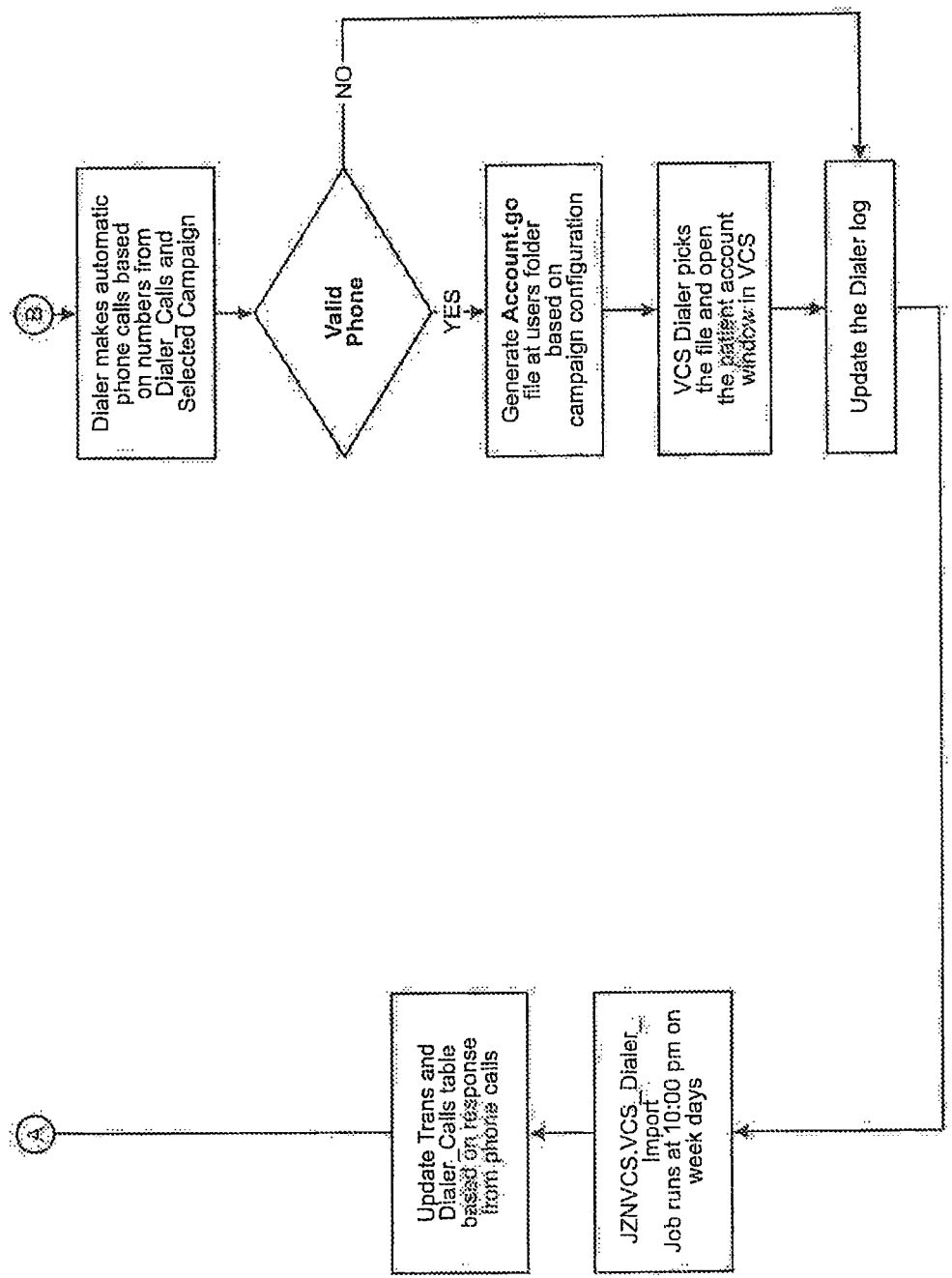

The Visual Collections System 100 is configured to perform a Dialer Process (S115). The Dialer Process will be discussed in more detail later with respect to FIG. 13A-B.

The Visual Collections System 100 is configured to perform a Payment Process (S116). The Payment Process is performed in FIG. 2A-B.

The Visual Collections System 100 is configured to perform a Clinical Appeals Process (S117). The Clinical Appeals Process will be discussed in more detail later with respect to FIG. 14A-C and FIGS. 23-32.

Figure 15A:
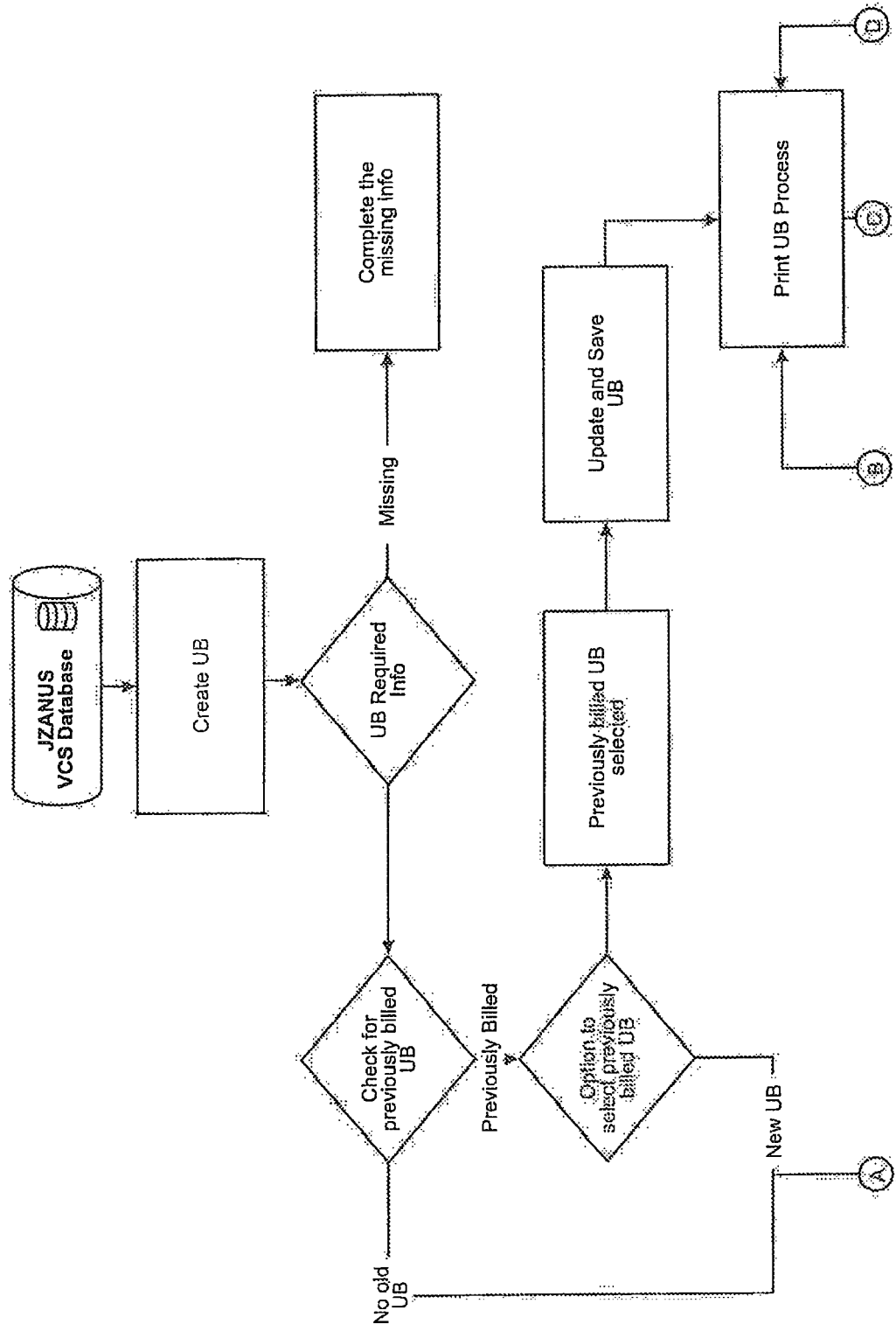
FIG. 15A-B illustrates a UB Process that may be executed by the VCS according to an exemplary embodiment of the present invention.
Figure 15B:
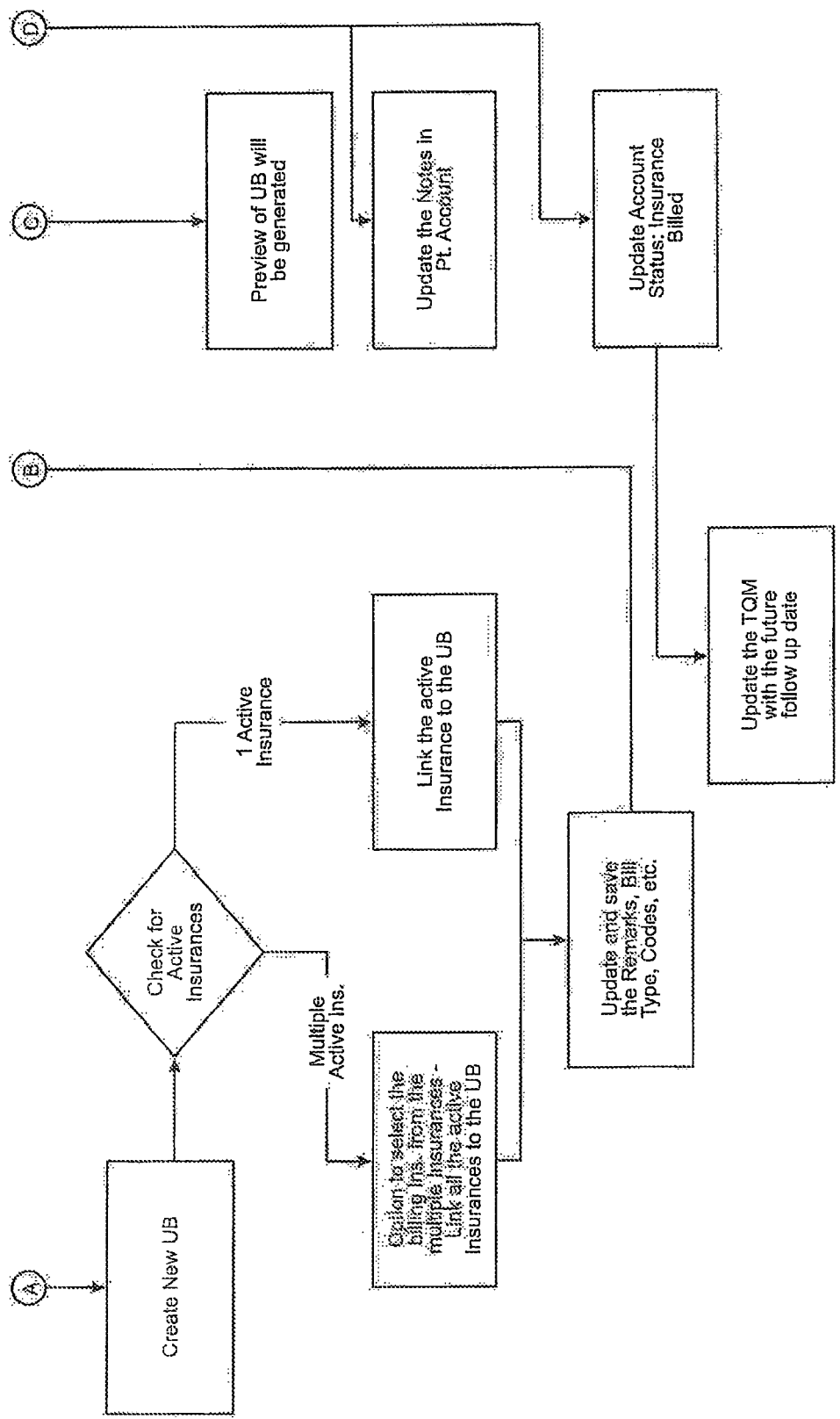

The Visual Collections System 100 is configured to perform a UB Process (S118). The UB Process will be discussed in more detail later with respect to FIG. 15A-B.

Figure 16:
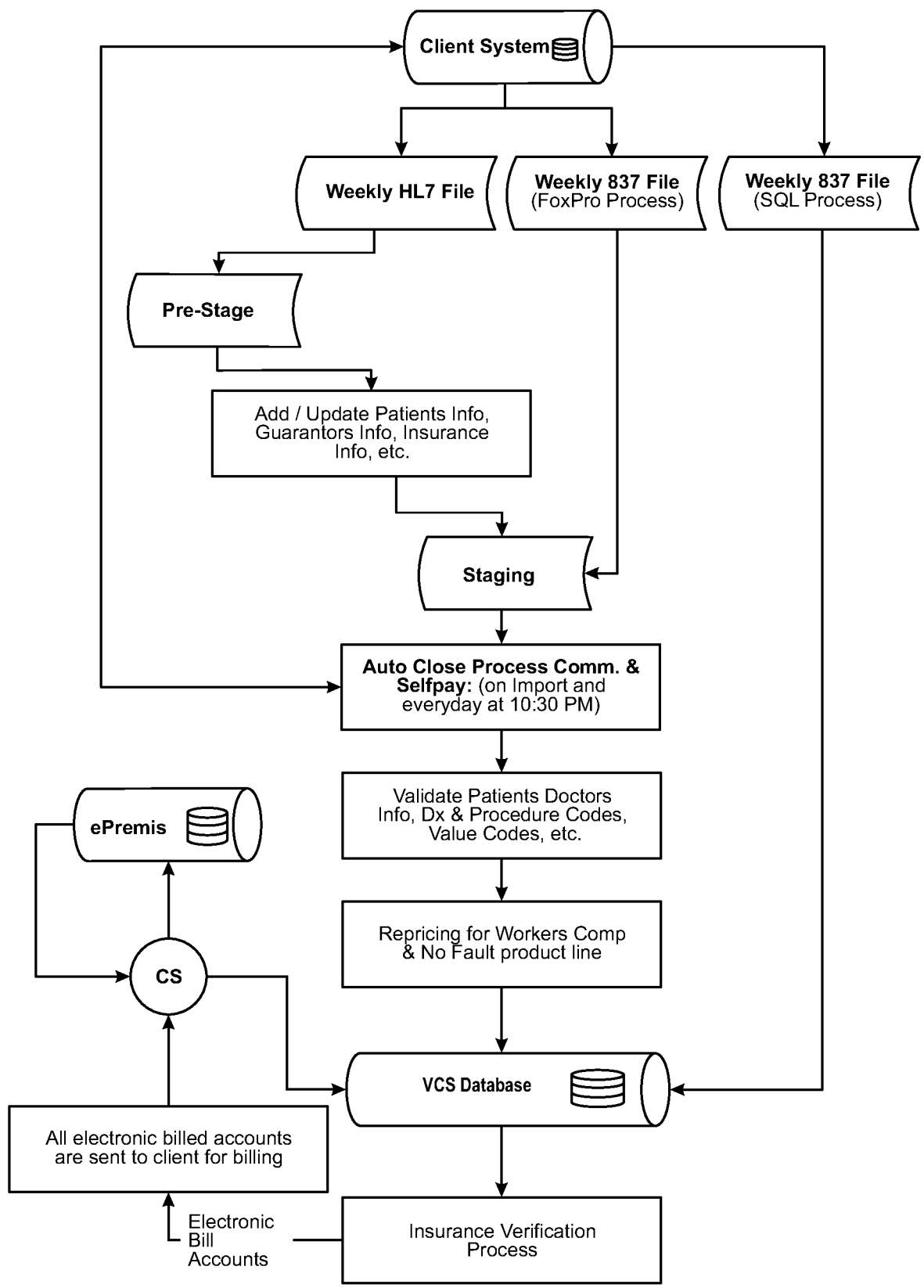
FIG. 16 illustrates a Claim Verification Process that may be executed by the VCS according to an exemplary embodiment of the present invention.

The Visual Collections System 100 is configured to perform a Claim Verification process with ePremis (S119). The Claim Verification process with ePremis will be discussed in more detail later with respect to FIG. 16.

Figure 17:
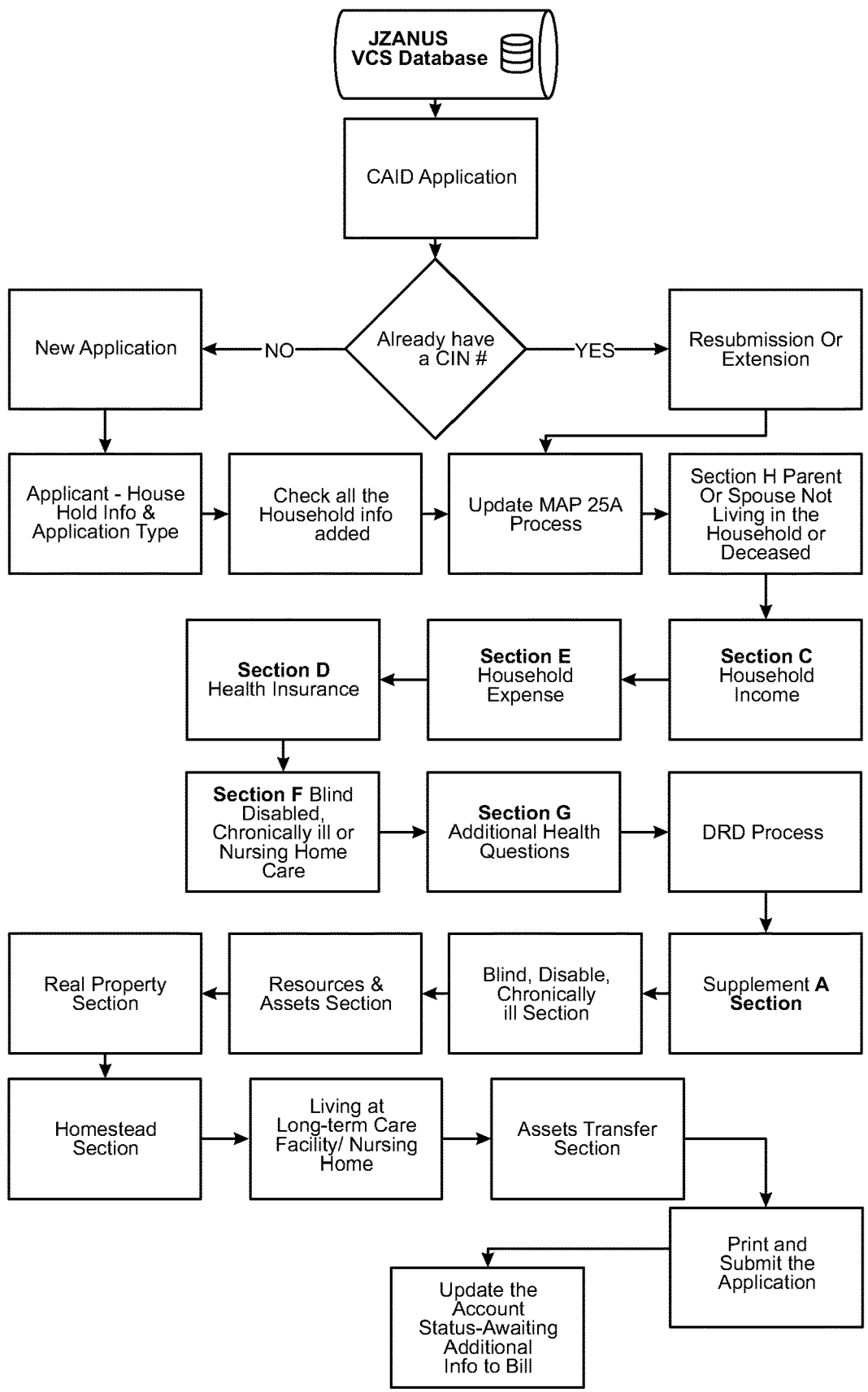
FIG. 17 illustrates a Medicaid Application Process that may be executed by the VCS according to an exemplary embodiment of the present invention.

The Visual Collections System 100 is configured to perform a Medicaid Application Process (S120). The Medicaid Application Process will be discussed in more detail later with respect to FIG. 17.

Figure 18:
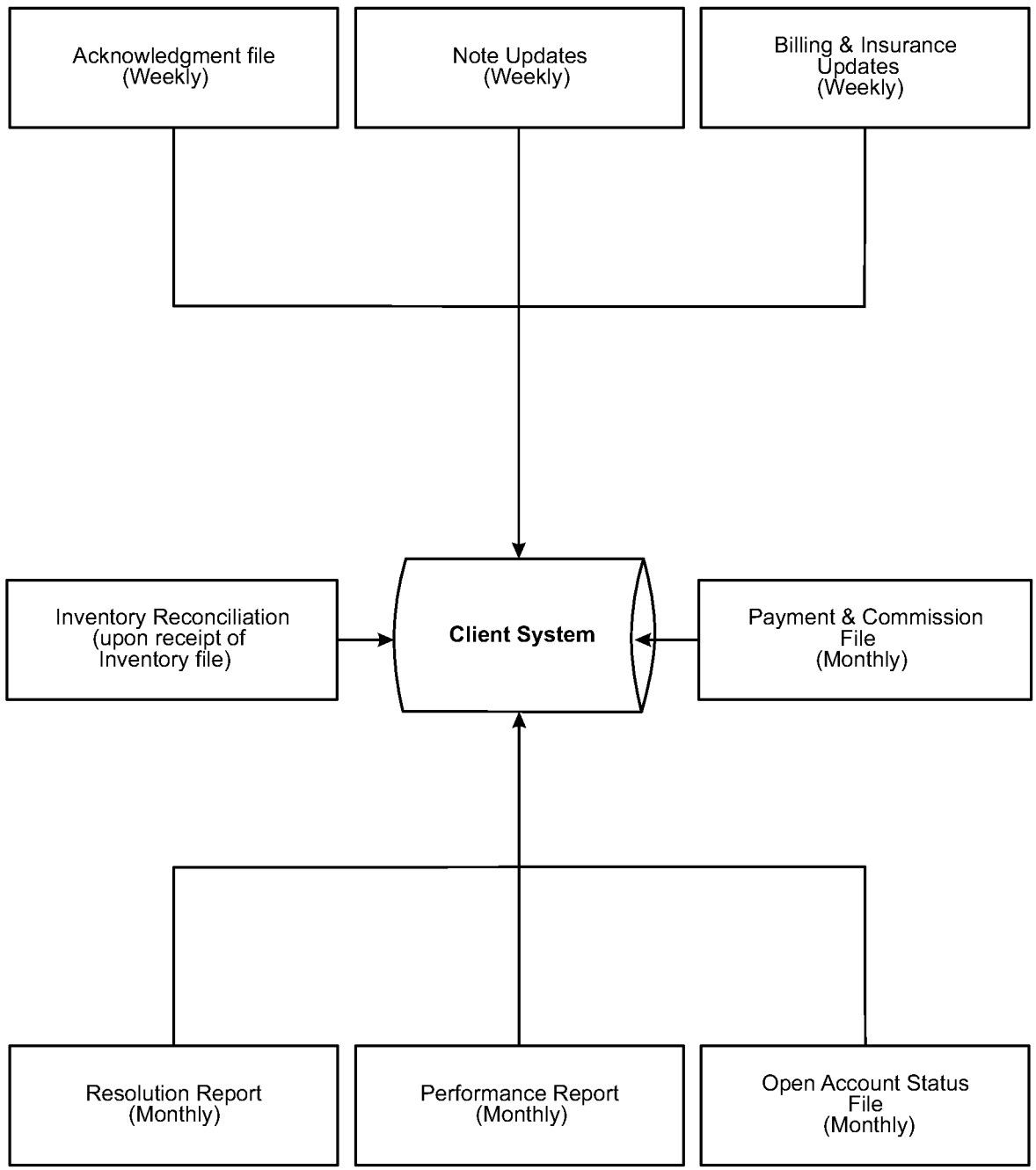
FIG. 18 illustrates a Reports to Client Workflow Process that may be executed by the VCS according to an exemplary embodiment of the present invention.

The Visual Collections System 100 is configured to perform a Reports to Client workflow Process (S121). The Reports to Client workflow Process will be discussed in more detail later with respect to FIG. 18.

Figure 19:
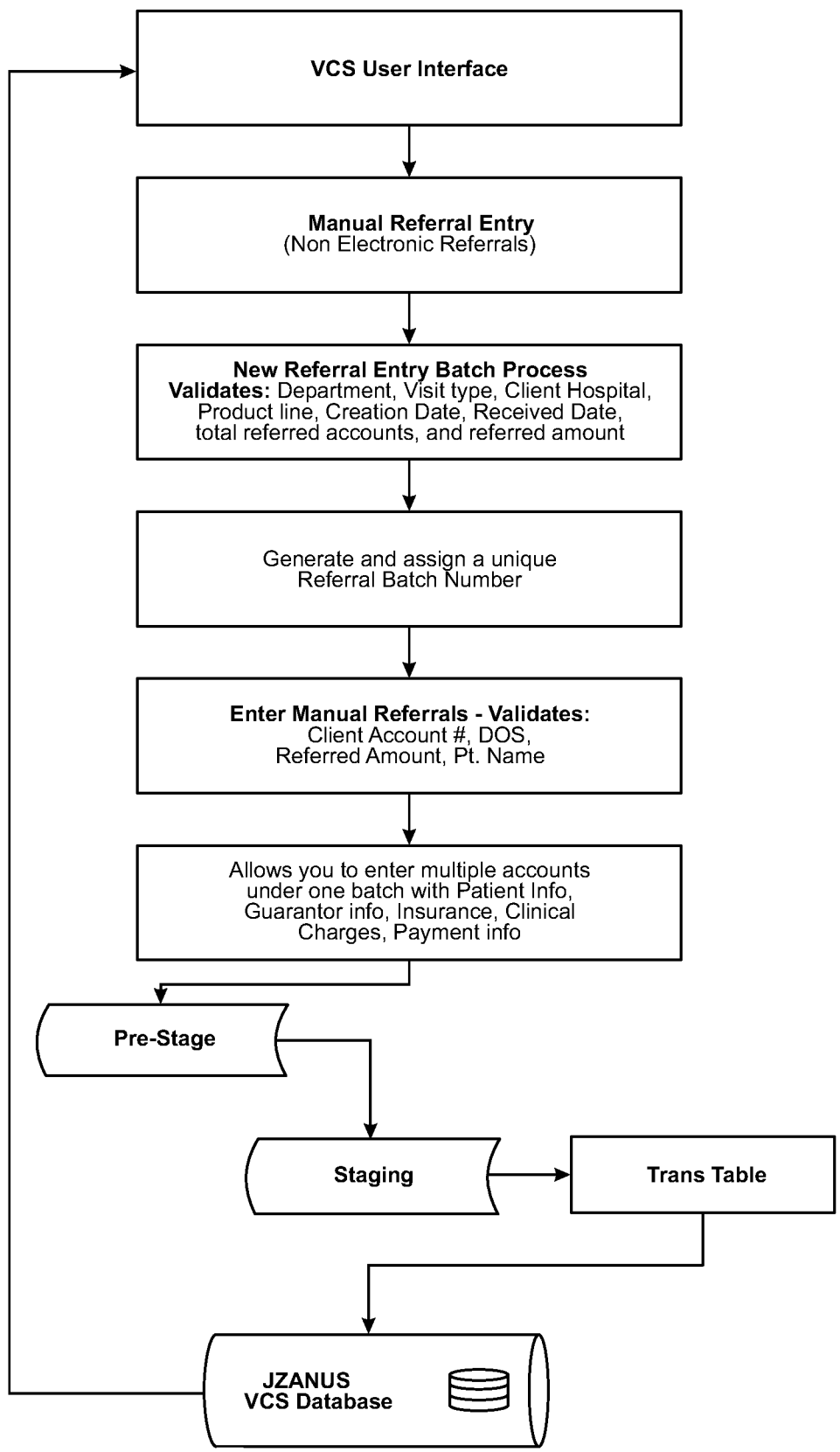
FIG. 19 illustrates a Manual Referral Entry Workflow Process that may be executed by the VCS according to an exemplary embodiment of the present invention.

The Visual Collections System 100 is configured to enable a user to manually enter a referral according to a Manual Referral Entry Workflow Process (S121). The Manual Referral Entry Workflow Process will be discussed in more detail later with respect to FIG. 19.

The Visual Collections System 100 is configured to periodically submit the patient account updated to a corresponding client (S122). The updated file may contain account notes, billing information, insurances updates, claims information, and status information about one or more claims (e.g., processed, denied).

Referring back to FIG. 8A-B, the Timely Filing & Due Date Process is used to ensure that an unpaid claim in a client account is worked on within a timely manner. There is a limited amount of time to work on a claim that depends on the type of insurance and date of service (service provided to the patient by a healthcare provider such as a hospital). For example, each different type of insurance stipulates that a claim be filed (e.g., sent to the insurance company) within a different time period (i.e., the Timely Filing Period) from the date the service was provided (date of service) in order for the claim to be reimbursed. For example, the healthcare provider (i.e., the client) could specify an initial period that the healthcare provider (e.g., hospital staff) attempts to collect on the claim, and if the Client (hospital) has a contract with an outside vendor (e.g., an agent) to collect the missing revenue, then they can refer the claims to outside vendors as per the contact between Hospital & Vendors. After that, an outside vendor (collector) is authorized to begin collection of the claim. For example, if the Initial Period is 60 days and the Timing Filing Period is 180 days, the Hospital will transfer the referral to an outside vendor at the end of day 60. Now the Vendors and the collector would have 120 days left to submit the claim to the appropriate insurance company. In an exemplary embodiment, the Timely Filing & Due Date Process adds the Timely Filing Period and the Last Due Date (DOS+Timely Filing Period) to each of the accounts. In an exemplary embodiment, for a given account, if the current Date is greater than the Last Due Date or close to the Last due Date, the account is displayed in a manner designed to get the attention of the collector. For example, the text that identifies the account could be displayed with a Red color, as flashing text, etc. The Timely Filing & Due Date Process may be linked with the Claim Verification Process that is configured to pull all the accounts that are approaching the Last Due Date and has no claim information. The Last Due Date or Timely Filing Period is determined by the contract between the Hospital and the Insurance companies. All received accounts have Patient Insurance information. The Timely Filing period starts from the Date of service provided by the Hospital. The team manager can then assign these accounts to one or more investigators (collectors), so they can check the claim, contact the insurance company, or rebill the insurance if needed.

The Visual Collections System 100 maintains a secure Web-based location (e.g., having a certain Internet Protocol Address). The client then electronically transfers a file to the secure Web-based location that includes information on one or more client/patient accounts (S801). As an example, the file may be transferred using the File Transfer Protocol (FTP). The file may include codes of services provided to a patient, the dates these services were provided, the amounts charged for these services, the identity of the health insurance(s) carried by the patient, the amount the patient owes on each service, etc.

The system 100 periodically (e.g., weekly) checks the Web-based location for a new file, opens the new file, extracts the data from the file, and imports the data into the database 110 (S802). The data may include patient visit information about a patient visit to a healthcare provider such as Patient Name, Date of Birth, Social Security Number, demographic information, insurance information, type of service provided (e.g., procedures performed), date service(s) provided, amount of payments already made, source of those payments (e.g., patient, insurance company), denial information (e.g., identity of insurance(s) that denied payment).

The system 100 may calculate the Timely Filing Period for each account imported into the database, and add the Timely Filing Period to an account associated with the imported account.

The system 100 updates the Timely Filing Period based on addition/changes to the insurance of a patient (S803). For example, the Timely Filing and Due Process can periodically check all the open accounts in the VCS for any update or changes in the insurance. One patient can have multiple accounts, where each visit to the hospital will open a new account. A patient can have multiple insurances also. For example, if a patient has 2 insurances, one has to be primary and the other has to be secondary. The primary insurance is first billed once, and then afterwards the secondary insurance is billed if any copay or coinsurance is applied by the primary insurance. If Primary Insurance is being billed, then the Timely Filing Period depends on the contract between the primary insurance and the hospital. If secondary insurance is being billed, then the timely filing period depends on the contract between the secondary insurance and the hospital. An Insurance Eligibility process can be used to determine whether a patient has active insurance or not. If the insurance is changed, then the system 100 enables a user to manually update the database 110 to reflect the new insurance.

The processes of FIG. 7A1-A3 and/or FIG. 7B1-3 may then be used to verify the imported claim to determine whether the claim was billed or not billed (S804). For example, a claim is considered billed if the claim was already submitted to insurance.

FIG. 7A1-3 depicts a collections workflow for the system 100. The system is configured to periodically run a claim status process on the claims previously imported into the database 100 to get status on the claims that were submitted to a particular insurance company (S701). The claim status process of step S701 may be implemented by the process depicted in FIG. 7B1-3.

Referring to FIG. 7B1-3, in the Web Claim Search process (S750), the process is programmed to look for those insurances which provide online claim status. The system uses a pre-defined list created based on the insurances which provide online claim status.

The list was created by a manual web search done by the investigators. In an embodiment, the process maintains the website address and login credentials of several insurance companies.

Insurances which do not provide the Online claim status are excluded from this Claim Websearch Process (S770) and the Account Status will not be changed/updated by this process. The investigators can manually contact those Insurances via Phone/Fax or by postal mail to inquire about the claim status.

The process retrieves all the accounts it has stored in the database 110 for the Insurances which provides online claim status and the accounts with a pre-defined set of Account statuses (S751). In an embodiment, the set of statuses includes statuses of "Eligibility Search Result Returned", "Initial Follow-up", "Investigate Eligibility/Name Search", "Name Search Returned", and "Investigate Patient Responsibility". In an embodiment, the only accounts that are retrieved are ones with claims not already websearched and not already paid by the insurance company.

For example, a record may be present in the database 110 that corresponds to a given account that includes a unique patient identifier (ID) to identify a patient, a patient name, a date of birth, a gender, a social security number, a date of visit, a visit type, charges, insurance information, etc.

The status "Initial Follow-up" is the first status assigned to an account when the patient account is imported into the system 100. This status could indicate that the patient account has a link to valid insurance.

The status "Investigate Patient Responsibility" means that a collector should check whether the patient is responsible for the amount of an owed balance.

The process stores information about each of the retrieved accounts that indicates claim information of the corresponding account to search, and whether the account has already been searched (S752). For example, if an account has not been searched already and has active claims that were previously submitted, the information could include data indicating the account needs to be searched (i.e., the account is marked).

The process then passes data representing each of the marked accounts to the websearch manager (S753).

The websearch manager locks each of the marked accounts in the database 110 to prevent a user from manually changing the status of these accounts while the websearch is being performed (S754).

The websearch manager searches the website of the insurance company for claims of each the marked accounts to retrieve claim status information (S755).

If the search of the website retrieves one or more results, the websearch manager converts the claim status information into a file that is easier to parse (S756). In an embodiment, the file is a comma-separated values (CSV) file, which is a delimited text file that uses a comma to separate values. A CSV file stores tabular data in plain text.

The websearch manager then converts the CSV file into a format that is compatible with the database 110 (S757). In an embodiment, this conversion results in the creation of 4 datasets, header data including high level information, line item data including detailed information, reasons data including information on claims (e.g., information on whether claim paid/denied/pending, amount paid, reason claim denied, etc), and reasons master data including information for decision making on the denial response received. The Parsing process in which the System reads the data from CSV and moved to 4 different tables (Header, Line Item, Reason, and Reason Master) is unique for each insurance, as it depends on how the insurances are providing the data. The parsing program will look for those key words and pull the data into the respective tables. For example, some insurances refer to an ID associated with a claim as a Claim number, while others refer to the same element as a Claim ID, or a Customer Claim number. Fields in the Header table include: Account Number, Plan name, Client Code, Claim Number, Patient ID, Patient Name, Date of Birth, Service Date, Status, Claim Amount, Subscriber Name, Subscriber ID, Gender, Patient Control Number, Billing Provider Name, Billing Provider Tax ID, Billing Provider Address, Service Provider Name, Service Provider Tax ID, Service Provider Number, Service provider Address, Service provider Plan ID, Payment Date, Payment Method, Check Number, Check Date, Payer Name, Claim Status Date, Category Code, Status code, Entity, Remit Code, Check Trace Number, Bill Type, Medical Record Number, Claim Receive Date, Patient Responsibility, Total Claim Adjustment, Service Line Adjustment DRG Code, Check Bulk Amount, Check Status, Claim Status, Line of Business, Group, Authorization, Allowed amount, CAP FSS, Claim Reprocessed, Medicaid paid, Other insurance paid, Patient not covered, Physician provider not covered, and Physician Provider Adjusted, Service Desc. Trans Insurance.

Fields in the Line Item table include: Service ID, Service Date, CPT Code, Modifier, Units, Revenue Code, Claim Category, Status Code, Remit Code, Charge Amount, Payment Amount, Adjustment Amount, Adjustment Group, Adjustment Reason, Co Insurance, Co Pay, Deductible, Entity Ident, Diagnosis Code, Procedure Code, DRG code, Cap, Key, Allowed amount, Disallowed amount, Denial Reason, Line number, Denial Date, Link Check Date, Line Check Number, Medicare Paid, Other Insurance paid, Physician Provider not covered, Physician Provider adjusted, Service Desc., Patient not covered.

Fields in the Reason Table include: Claim Category, Reason Code, Reason Description, Key, and Line Item Number.

Fields in the Reason Master Table include: Denial Category, Carrier Code, Denial Reason Code, Denial Reason Description, Status Code, and Action.

The websearch manager analyzes the reason data to determine whether the claim is pending (S758).

If the claim is not pending, the websearch manager moves the data from the data sets into tables of the database 100 (S759). For example, the header data is moved into a header table, the line item data into a detail table, and the reasons data into a reason table in the database 100 (S759).

The websearch manager then determines from the reason data (e.g., in the reason table) whether the claim was paid or denied (S760).

If the claim was paid, the websearch manager updates the status of the account to "Investigate Patient Responsibility" or "Awaiting Payment Verification" (S759). For example, even though the claim is set to be paid by the insurance, the patient could still be responsible for a co-payment. For example, information in the patient account for the claim could indicate the patient has not paid the co-payment.

If the response type indicates the claim is in progress, the status of the account is updated to indicate the insurance company was billed and the claim is pending (S772).

Figure 9A:
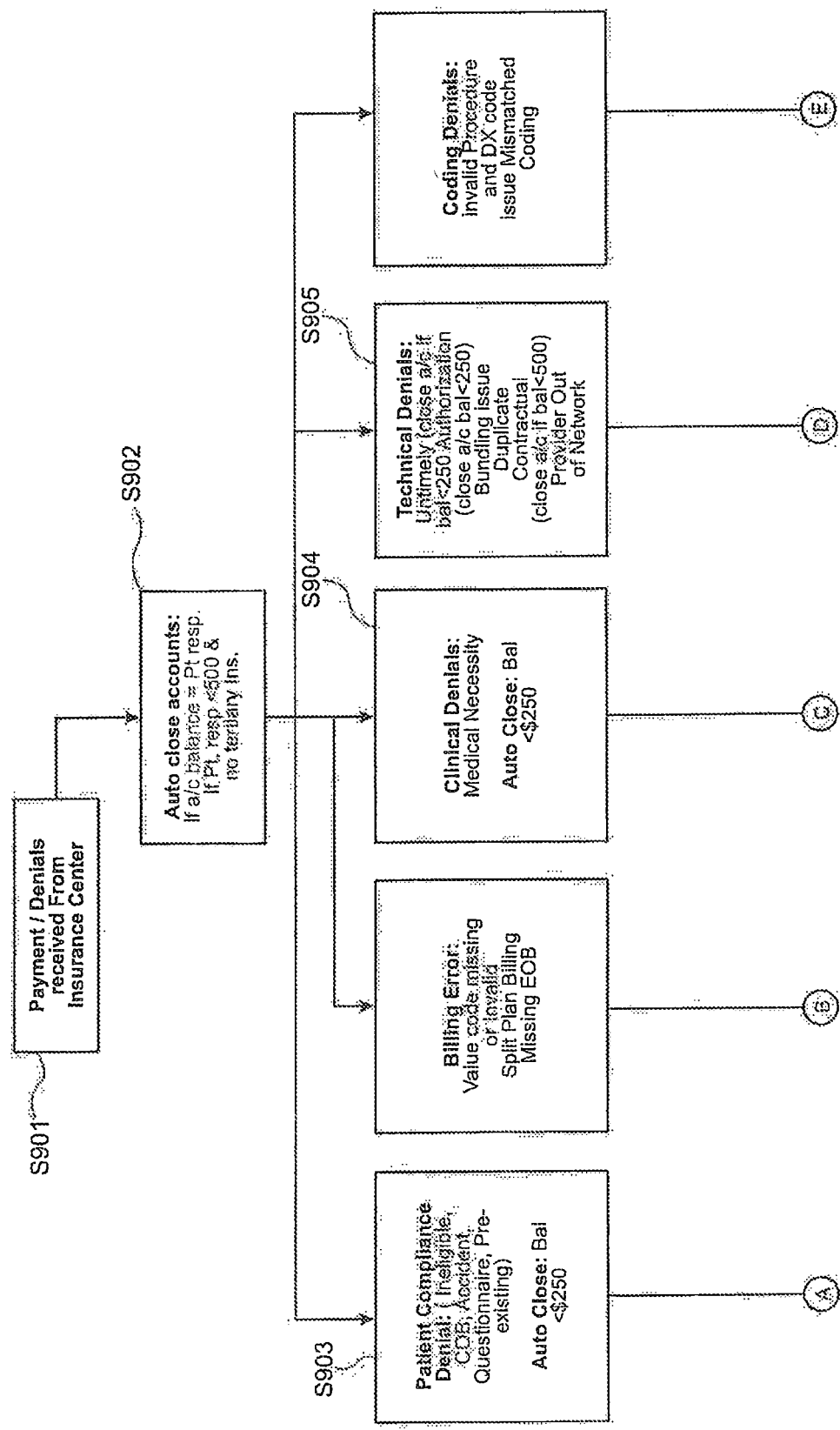
FIG. 9A-B illustrates a Denial Process that may be executed by the VCS according to an exemplary embodiment of the present invention.
Figure 9B:
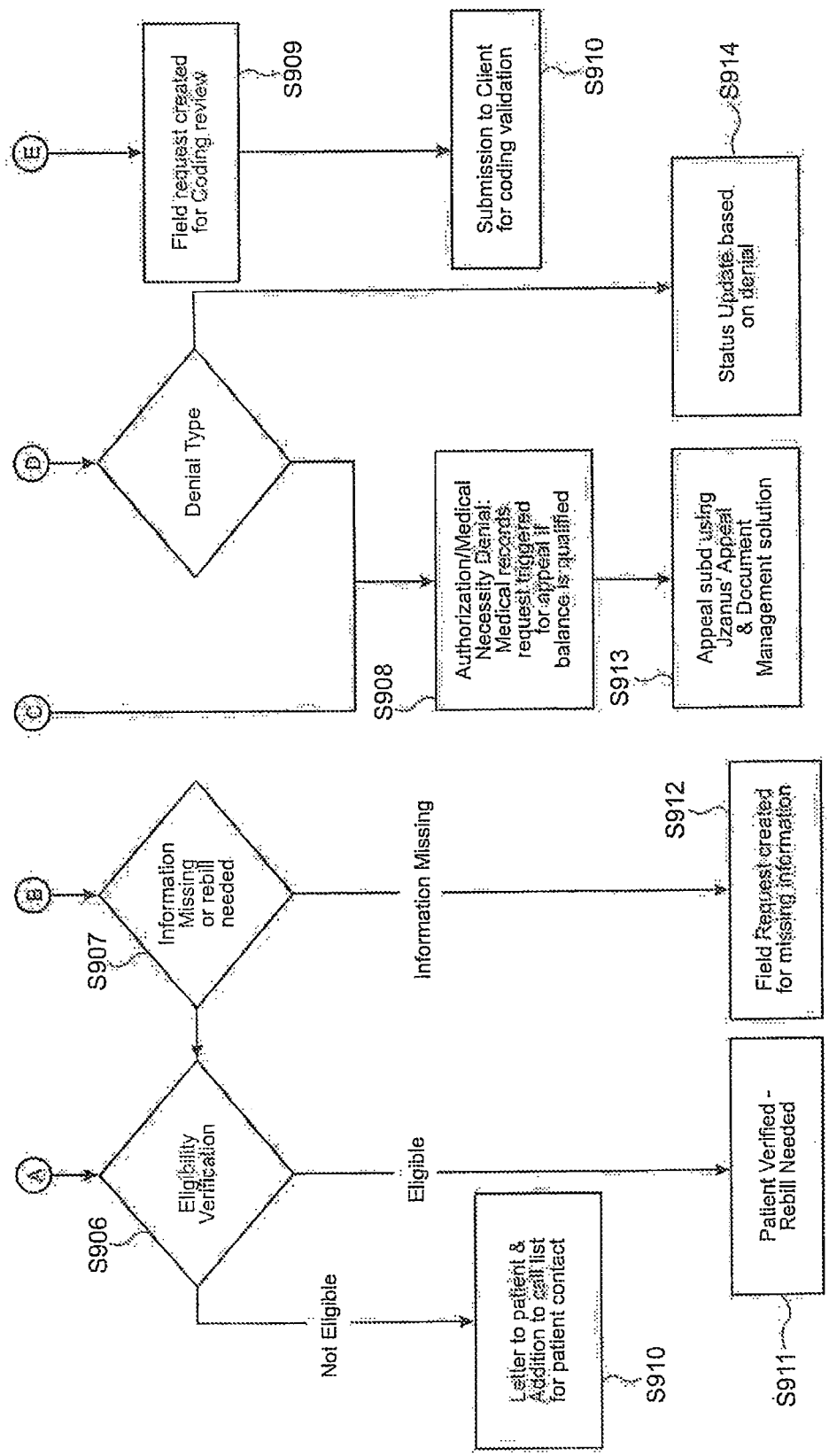

If the response type indicates the claim was denied, the websearch manager updates the status of the account depending on the denial type (S762), and executes the denial management workflow (S763) shown in FIG. 9A-B. Examples of different denial types include: non-covered charges, Duplicate Claim (e.g., same claim is submitted multiple times to insurance company), service not covered, provider not in contract with insurance company, etc.

The patient account is updated with status information about the claim (S764). For example, if it is determined that the claim was denied, a reference in the patient account to the claim is updated to indicate the claim was denied.

A log is then created with information about the claim searched on (S765). The log may identify the claim (e.g., include a claim number) and include information discovered as a result of searching on the status of the claim such as claim status, amount paid, date of payment, patient responsibility, and denial reasons.

The account status is updated according to the websearch response (S766).

If there is still some money owed on the claim (e.g., the co-pay is the responsibility of Patient or secondary insurance if patient has secondary insurance), the process is rerun using the secondary insurance (S767).

If the search of the website in S755 was not successful, then a log can be updated to indicate that No Claim was found (S768), which suggests that the claim was never submitted to the insurance company. Thus, a status flag of the account is set to indicate that it is ready for billing so a user of the system knows to submit the claim (S769).

Figure 8A:
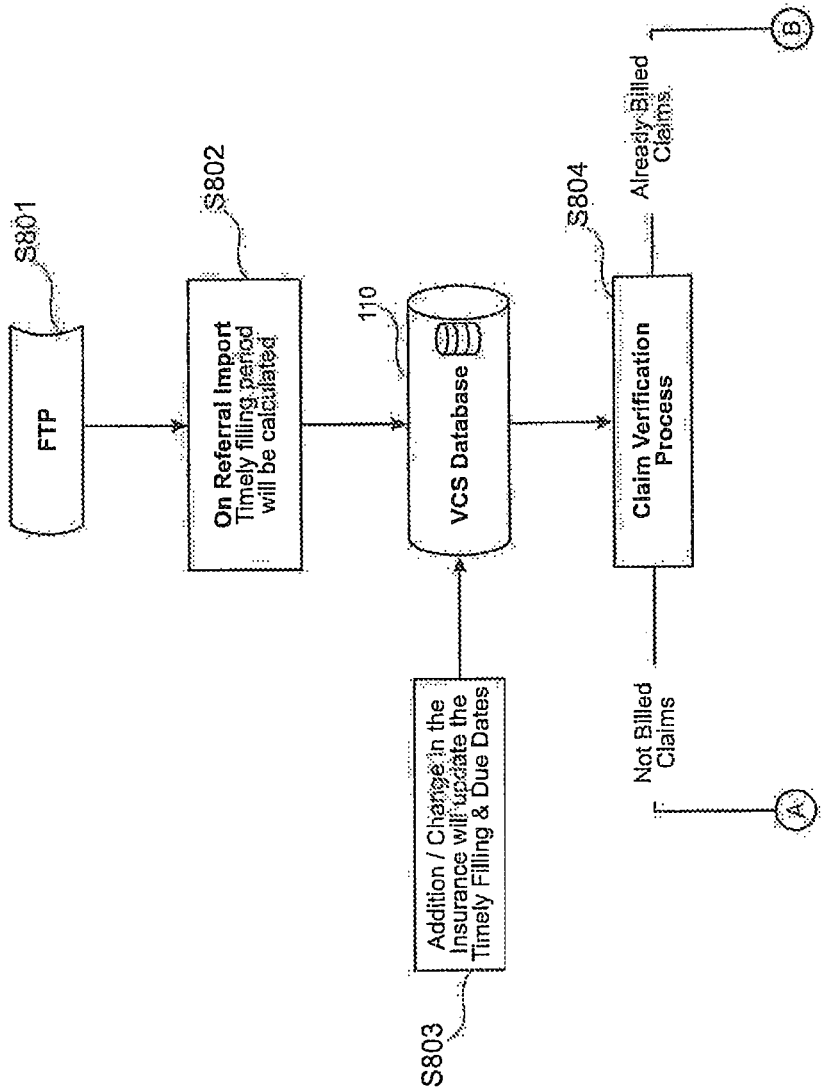
FIG. 8A-B illustrates a Timely Filing & Due Date Process that may be executed by the VCS according to an exemplary embodiment of the present invention.
Figure 8B:
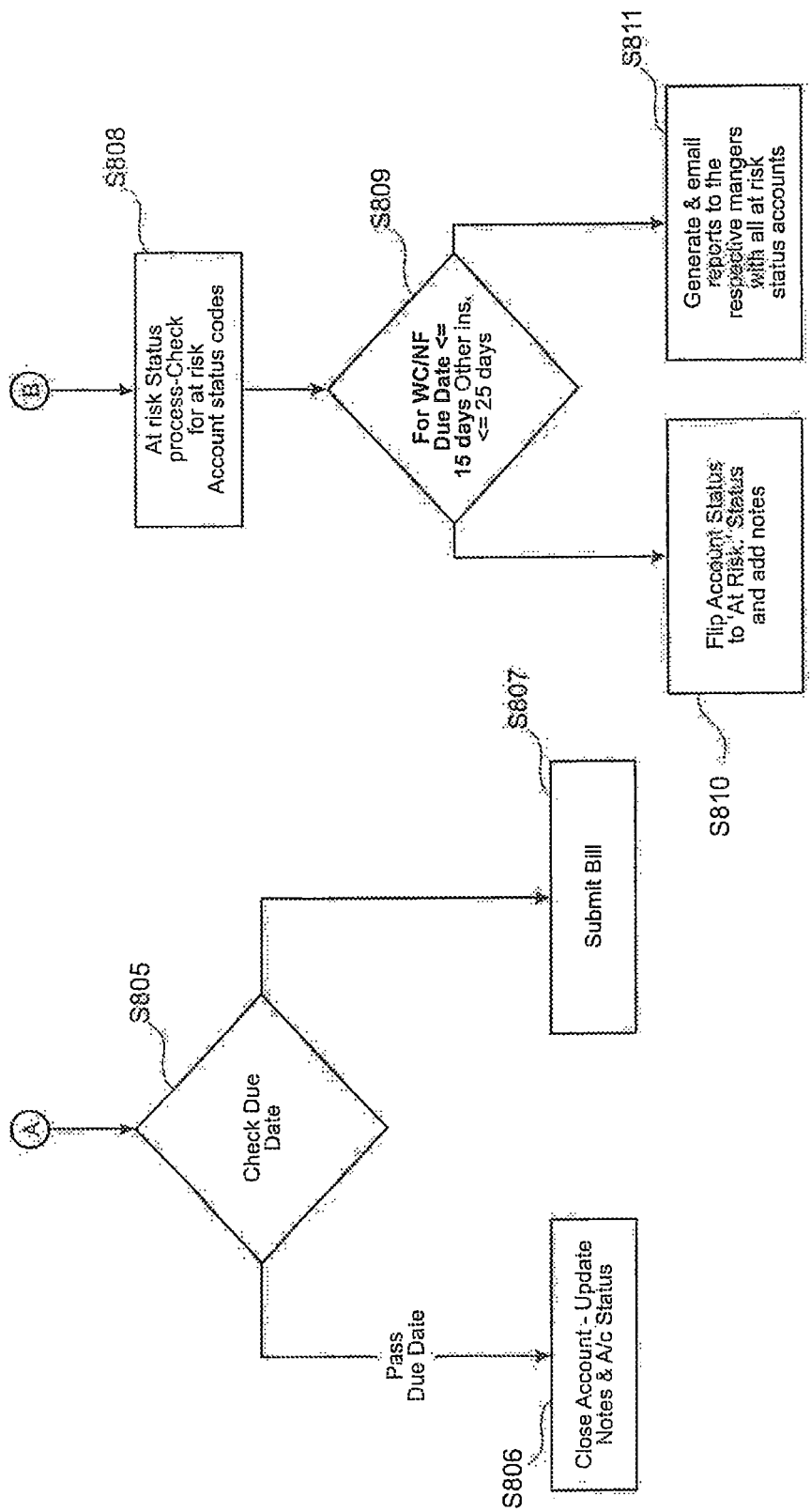

Referring to FIG. 8A-B, the Timely Filing and Due Date Process checks the due date of the claim that has not yet been billed (S805). The check may be performed by calculating the Last Due Date from the previously determined Timely Filing Period and Date of Service, and comparing the Current Date against the Last Due Date. The Timely Filing and Due Date Process could close the account associated with the claim if the Current Date exceeds the Last Due Date (S806). In an embodiment, a status field is associated with a claim, and the status is updated to 'closed' when the Current Date exceeds the Last Due Date. The Timely Filing and Due Date Process submits the claim (e.g., to insurance) if the current date does not exceed the Last Due Date (S807).

The Timely Filing and Due Date Process checks the risk account status of the claim if it was already billed (S808). The Timely Filing and Due Date Process may use processes of FIG. 7A1-3 and/or FIG. 7B1-3 to perform this check. For example, if an already billed claim is missing some information, but was submitted anyway, the system 100 can conclude the claim is at risk for being denied. The system 100 can then change the status of the account associated with the claim to "At Risk", draft a report about the risk, and email the report to a manager. The Timely Filing and Due Date Process then determines determine whether the already billed claim falls under Worker's Compensation (WC) or No Fault (NC), and determine whether the due date for submitting such a claim is close to being reached (S809). For example, WC/NF has 30-60 days for timely filing the claim. For example, if the claim falls under Worker's Compensation or No Fault, and the due date is in less than a certain period of time (e.g., 15 days), the status of the account is updated to "At Risk" (S810). If the due date is not in less than the certain period of time, the process generates a report on any at risk accounts or claims, and emails the report to a corresponding manager (S811). The process checks all the accounts which have not been billed to the Insurance and which are approaching the Billing Due Date. For all accounts returned by this check, the process flips the account status to an At Risk status, and sends an email report to the respective managers. Multiple emails may be generated depending on the number of accounts and clients (e.g., hospitals).

Referring to FIG. 9A-B, the Denial Management Workflow receives a payment/denial file from a client (e.g., a hospital) (S901). The payment/denial file has claims payment information or claims denial information. If the payment was made on the Claim, the claims payment information includes the Patient Account #, the DOS, a Claim Number, the Billed Amount, the Claim Paid Amount, the Patient Responsibility, the Claim Processed Date, the Check #, the Check Amount, the Check Date, the Check Cashed Date, the Co-Pay Amount, and the Allowances Applied Amount. If the claim is denied, the claims denial information includes the Patient Account #, DOS, Claim Number, Billed Amount, Claim Paid Amount, Patient Responsibility, Claim Denied Date, Denial Reason, and a Denial Code. The Denial Codes used by one insurance company vary from the Denial Codes used by another insurance company. For example, the Denial Code used by a first insurance company to represent a Denial indicating the patient is ineligible for reimbursement could be a first value and a second other value for a second insurance company. Examples of the Denial Codes include Ineligible, Coordination of Benefits (COB) error, accident, questionnaire, pre-existing condition, valid code missing, Invalid Split Plan Billing, missing EOB, not medically necessary, Untimely, not Authorized, Bundling Issue, Duplicate, Contractual issue (e.g., claim includes a procedure not covered by a contract between hospital and insurance company), provider-out-of-network, Invalid Procedure (e.g., issue with Procedure code due to incorrect Gender or Age), DX (e.g., diagnosis) code issues, and mismatched coding.

A DX code is a diagnosis code. There are primary DX codes and secondary DX codes. For example, the primary DX codes typically refer to the source of a disease such as an infection and the secondary DX codes typically refer to symptoms of the disease such as high fever, headache, running nose, sore throat, etc. If the doctor enters the symptom (e.g., running nose) as the primary DX code or enters the source of the disease such as the infection as the DX code, it will result in a DX code error.

Diagnosis codes are linked with the Procedure code and Procedure codes are linked with Service codes (codes associated with services provided). For example, if you have a DX code for a viral infection linked with a Service Code for repairing a fractured bone, it would result in a mismatch coding error.

In medical billing, you can link some services (charges) together under one code, which is known as Bundling. For example, a physician may have performed one service as the result of performing a second other service. For example, if a surgeon is performing an abdominal surgery and decides to remove the patient's appendix as well, the surgeon may not be able to bill for the appendectomy. Bundling occurs when a procedure or service with a unique CPT® or HCPCS code is included as part of a more extensive procedure or service provided at the same time. Sometimes, two different procedures are applied to two different parts of the body at the same time and can be billed separately, but insurance denied the claim as a Bundling Issue.

Getting a claim Authorized (i.e., preauthorized) is the process of getting an agreement from the payer (Insurance Company) to cover specific services/procedures before the service is performed.

Split Plan Billing means one insurance will cover one type of care (e.g., all the clinical visits) and another insurance will cover a second type of care (e.g., all emergency visits). A Split Plan Billing error could mean that the Clinical visit claim was submitted to insurance that was responsible to cover the emergency visits only or vice versa. Untimely means that a claim was submitted to the insurance company after the Last Due Date. The insurance company can deny a claim that is submitted too far after the date of service (DOS). Each insurance company has a different contract with the healthcare provider/client (e.g., Hospital) and as per the contract; the claim needs to be submitted within a certain period after the DOS. For example, that period ranges between from 30 days and 2 years depending upon the contract and type of insurances (Workers Comp, No Fault, Commercial, Medicaid, etc).

The system groups some of these different types of denials into related denial categories. A COB process determines which services are covered under the insurance plan. If the patient has multiple insurances, the COB process determines which insurance plan has the primary payment responsibility and the extent to which the other plans will contribute. The COB process could return a COB error if it is unable to determine which services are covered under each insurance plan, is unable to determine which insurance plan has the primary payment responsibility, or is unable to determine the extent to which other plans will contribute when there are multiple insurances. The COB process can ensure that claims are paid correctly by identifying the correct insurance and also ensure that the amount paid by the plans in dual coverage situations does not exceed 100% of the total claim.

The denial types of ineligible, COB error, accident, questionnaire, and pre-existing condition are grouped into a first denial category referred to as "Patient Compliance Denial".

The denial types of Value code missing, invalid split plan billing, and missing EOB are grouped into a second denial category referred to as "Billing Error".

The denial types of not medically necessary are grouped into a third denial category referred to as "Clinical Denial Error".

The denial types of untimely, not authorized, Bundling Issue, Duplicate, contractual, and provider-out-of-network are grouped into a fourth denial category referred to as "Technical Denials".

The denial types of invalid procedure, DX code issues, and mismatched coding are grouped into a fifth denial category referred to as "Coding Denials".

In an exemplary embodiment, the system assigns each denial category its own unique category code.

The system maintains a table for each insurance company that maps each of their denial codes to one of these category codes. For example, if a denial code of 1 is received from a first insurance company that represents a denial based on a pre-existing condition, and a denial code of 2 is received from a second insurance company that also represents a denial based on a pre-existing condition, and the category code for patient compliance denials is 11, both of these received codes (e.g., 1 and 2) can be mapped or converted to 11 using the table.

The denial process determines whether to close a patient account based on certain conditions (S902). A closed account is returned to the client, and collectors only work on accounts that are open. This determination may include determining whether the balance of the patient account is the responsibility of the patient or not. For example, the patient is responsible for the deductible and the co-payment. If the balance does not include the deductible or the co-payment (e.g., deductible and co-payment already paid), and the primary insurance has already paid its share, the system can bill secondary insurance the balance. If the primary and secondary insurance were already billed and a balance remains due to only patient responsibility, the system closes the account. The system can close the account if the claim was both processed by primary and secondary insurance, there is no tertiary insurance, and the patient is responsible for less than a certain amount (e.g., $500).

The denial process also determines whether to close the accounts based on the category of denial and the amount owed.

If the type of denial is a Patent Compliance Denial, and the balance of the account is less than a certain amount (e.g., $250), the account is closed (S903).

If the type of denial is a Clinical Denial, and the balance of the account is less than a certain amount (e.g., $250), the account is closed (S904).

If the type of denial is a certain type of Technical Denial, and the balance of the account is less than a certain amount, the account of closed (S905). For example, if the claim is denied because it is untimely or for lack of authorization, and the balance is less than a first certain amount (e.g., $250), the account is closed. For example, if the claim is denied due to a contractual reason, and the balance is less than a second certain amount (e.g., $500), the account is closed.

If the category of denial is a Patient Compliance Denial, and the balance that is owed is >=a certain amount (e.g., $250), the system performs an eligibility verification process to determine whether the claim is eligible for reimbursement by insurance (S906). If the claim is not eligible, then the system drafts a letter to the patient and adds the patient to a call list so that the patient can be contacted (S910). For example, an entry is added to the call list identifying the patient, listing contact information of the patient (e.g., a telephone number, a mailing address, and email address, etc.), and listing information about the claim (e.g., amount owed, service performed, date of service, identity of provider of service, type of denial, etc.). If the claim is eligible, then the system either automatically re-bills the claim (e.g., resubmits the claim to the insurance) or sets a status of the claim to indicate that a re-bill is necessary (S911). For example, a human being can review the claims whose statuses have been set to re-bill to determine whether the claim needs to be revised before it should be re-billed.

If the category of denial is a Billing Error denial due to missing information, the system attempts to automatically insert this missing information (S907). If the attempt is not successful, then the system creates a field request for the missing information (S912). For example, the system can maintain a log that lists claims that are missing information so that an individual can review the claims in the log and manually edit them to insert the missing information. If the missing information was successfully inserted or the Billing Error was not due to missing information, the systems passes the claim onto the Eligibility Verification process that is executed at step S906.

Figure 14A:
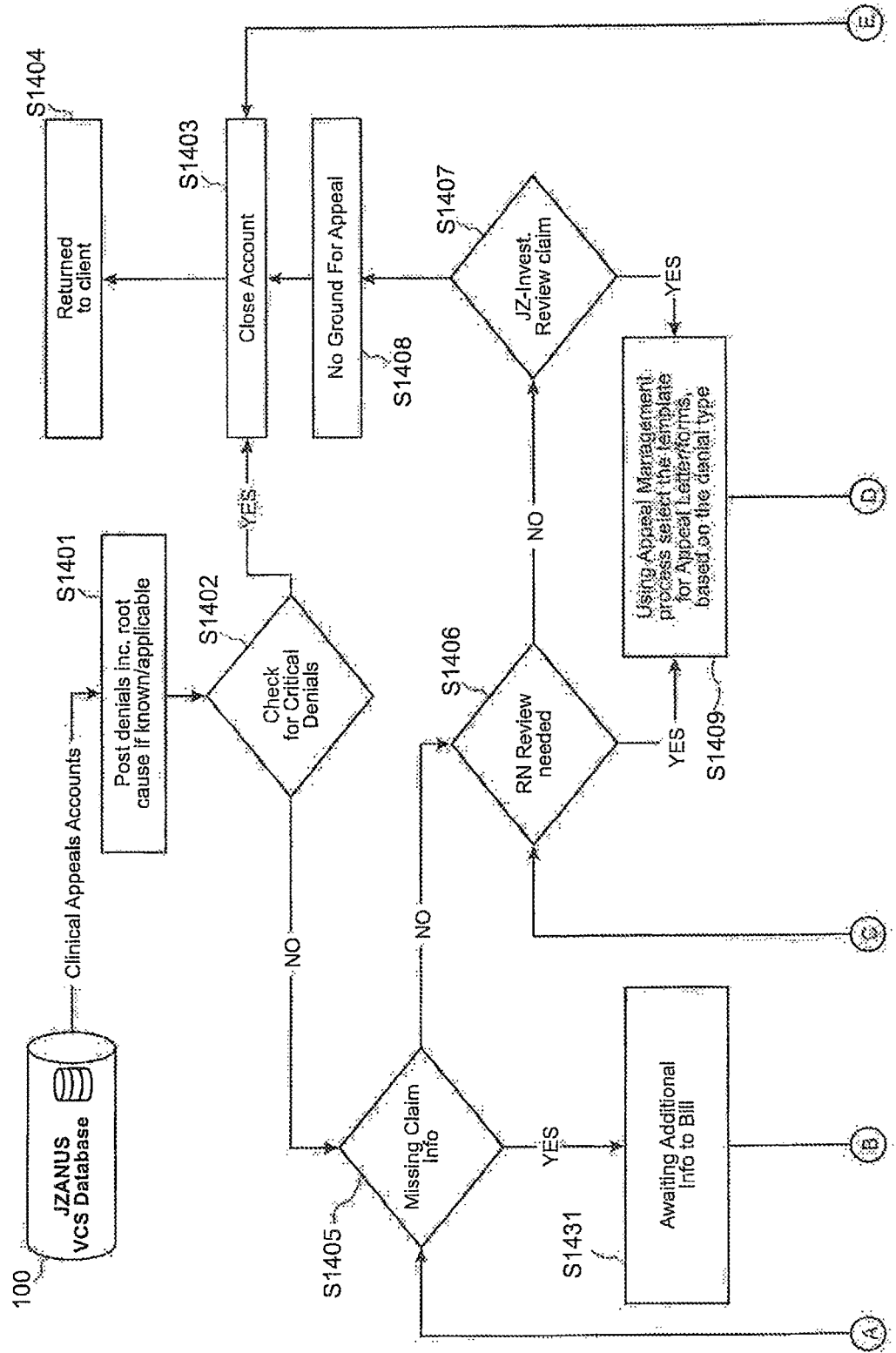
FIG. 14A-C illustrates a Clinical Appeal Process that may be executed by the VCS according to an exemplary embodiment of the present invention.
Figure 14B:
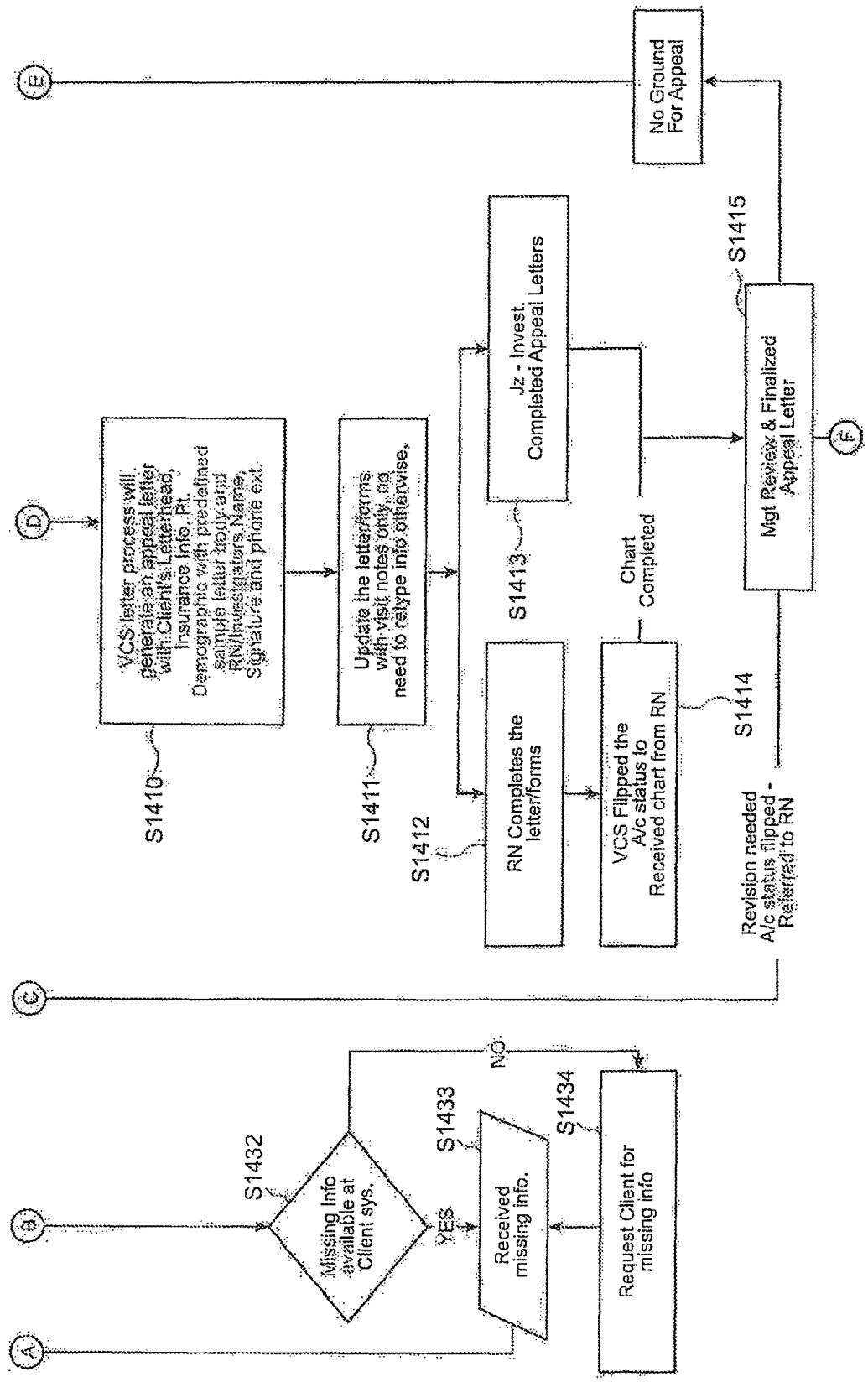
Figure 14C:
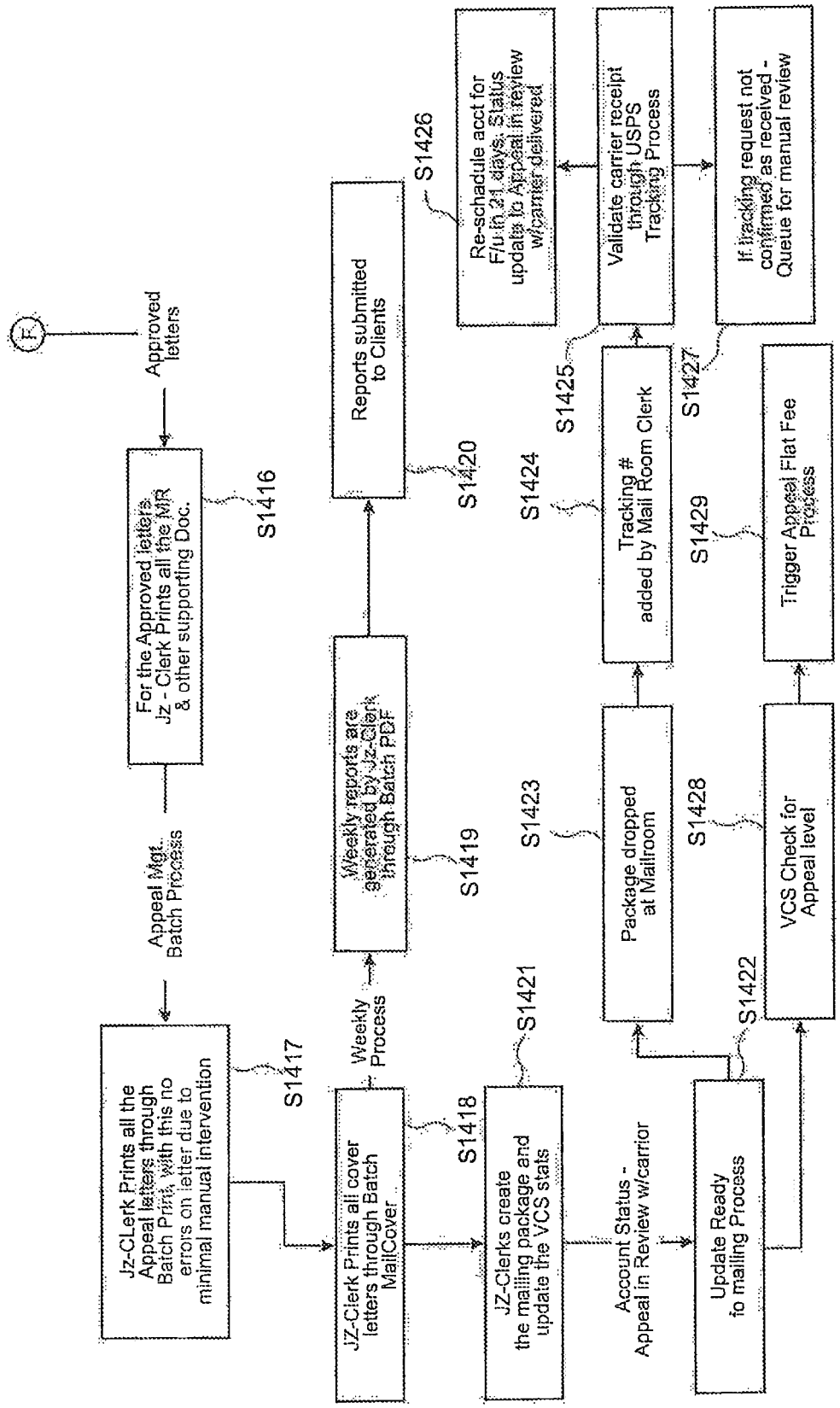

If the category of denial is a Clinical Denial or a Technical Denial, and the balance on the account is qualified (e.g., above a certain amount), the status of the claim may be set to indicate that it is to be appealed (S908). For example, the system can be set to appeal certain types of Clinical Denials such as Medically Necessary and certain types of Technical Denials such as Lack of Authorization. The system can then automatically appeal the claim using the Clinical Appeal Process (S913), which is illustrated in FIG. 14A-C.

If the claim has a category of denial of Coding Denial, the system creates a field request for a coding review of the claim (S909). For example, the claim can be added to a log that lists claims that need to have their billing codes reviewed. The system can then send a notification (e.g., an email) to the client (e.g., the hospital) that indicates the claim has a coding error and identifies the code with the error (S910).

The system may also update the status of the claim with the category of denial or the specific denial type of the category of denial (S914). The denial type may be mapped to some action.

Referring back to FIG. 14A-C, in the Clinical Appeals Workflow, a user can submit a denied claim to the Clinical Appeal Process (S1401). Once the denial is received, the investigators will post that denial in the patient account, determine the root cause of the denial after reviewing the denial, and update the information in the patient account. The process determines whether the denied claim was denied for a reason other than a critical denial (e.g., claim was submitted late) (S1402). The reason may be found in the reason table. If the reason is a critical denial, then the account is closed (S1403) and the resolution is added to the account and an Account status flag will be changed to closed, and returned to the client (S1404). For example, a flag associated with the account may be set to a value that indicates the account is to be sent back to the client and also the account is closed. When an account is closed, no one can update any information in that account. Closed accounts are never deleted from the VCS. They are just updated with a certain resolution and marked as being a closed account.

If the denial is not a critical denial, the process determines whether the claim was denied due to missing information (S1405). For example, a claim needs to include a certain required set of information to be submitted, and if the claim is missing one or more of the required information, it is considered to be missing information.

If the claim was not denied for having missing information, the process determines whether review by a healthcare provider (e.g., someone skilled in medicine such as a nurse or a doctor) is needed (S1406). For example, if the claim was denied for a reason only the healthcare professional would understand, it can be concluded that the claim needs to be reviewed by a healthcare Professional (e.g., a Nurse). If review of the claim by a healthcare Profession is needed, the team supervisor will assign the claim to the healthcare Professional for their review.

If the denied claim does not need to be reviewed by a Healthcare Professional, then the team supervisor will assign that claim to an Investigator for their review (S1407).

If the Investigator determines there is no ground for appeal, a status flag associated with the claim is set to indicate that there is no ground for appeal (S1408). For example, the Investigator can use a graphical user interface of the system to review a denied claim that they are allowed to review and update the Account status and add a resolution to the account so that the account will be closed.

For example, the system may include a graphical user interface accessible by the healthcare professional to view all claims that require review by the healthcare professional. The graphical user interface is configured to provide template appeal letters/forms (e.g., see FIGS. 23-32) to the healthcare professional based on the denial type (S1409). In an exemplary embodiment, a letter template has three sections, a non-editable header section, an editable middle section (e.g., Letter Body), and a non-editable foot/footer section. The header section may include Hospital Letterhead (e.g., name/address of hospital, name of department, etc.), insurance information, and patient demographic information. The information in the header section is automatically populated by the system and non-editable (e.g., grayed out) by a healthcare professional or an investigator. The middle section is the Letter body and may be fully editable by a healthcare professional or an investigator. For example, the healthcare professional typically enters clinical details and other appeal information in the middle section. The footer section is non-editable and pre-populated with a signature, a designation (e.g., Nurse, LPN, RN, etc), and contact information of the healthcare professional or the investigator.

An investigator may also use the graphical user interface to create an appeal letter for a claim that does not require review of a healthcare professional and for which an investigator deems worthy of appealing. After the worker selects a given pre-selected template, and enters information into fields of the template, the process generates an appeal letter with letterhead of the client, the insurance information of the patient, demographic information of the patient, the investigator's name (e.g., name of healthcare professional reviewing the claim), a signature of the investigator, and contact information for the investigator or the collector (S1410). The graphical user interface will be described in more detail below with respect to FIGS. 23-32.

The process automatically inserts into the letter/forms visit notes (S1411). These notes are created in the letter templates with Service codes, dates or units which are marked with text (e.g., XXXX) which indicates that data needs to be entered by a Healthcare Professional Nurse or an Investigator. Thus, there is no need for the professional/investigator to retype the visit notes into the appeal letter, which could introduce errors.

The graphical user interface includes a mechanism to enable the healthcare professional to set a status of the appeal letter for the claim to indicate the letter has been completed (S1412).

The graphical user interface includes a mechanism to enable the investigator to set a status of the appeal letter for the claim to indicate the letter has been completed (S1413).

A process can be run in the background that periodically checks the status of appeal letters to determine whether a given letter has been completed. If the letter has been completed, the process sets a status of the claim to indicate that the appeal letter is ready to be reviewed (S1414).

The system may include a graphical user interface accessible by a manager that enables the manager to review all the appeal letters that are ready to be reviewed, and to inform the system whether the appeal letter is to be approved or a revision is needed (S1415). For example, the appeal letter that is ready to be reviewed may be presented in the graphical user interface with toggle buttons labeled Finalized or Voided where selecting the Finalized toggle button results in the approving of the appeal letter, and selecting the Voided toggle button may result in requesting the Healthcare Professional/Investigator to recreate the Appeal letter.

A user interface of the system enables a clerk to print all the Medical Records (MR) and supporting documentation (e.g., clinical visit notes) for the approved appeal letters (S1416).

The system may perform a batch process to print all the approved appeal letters (S1417). Since many parts of the letters were pre-populated from information extracted from the claim and information extracted from the account of the patient, the letters should have little or no errors.

The process may then batch print all the cover letters for the approved (finalized) appeal letters (S1418).

A graphical user interface of the system may be present that enables the clerk to generate a weekly report about the appeal letters for a given client that was approved (S1419).

The system may then automatically send the report to the client (e.g., a hospital) (S1420). For example, the system can email the report to the client.

A clerk may create the mailing package and update a VCS Account Status to Appeal in Review with Carrier (S1421).

The Process determines whether the Package is ready to mail, which triggers the Appeal flat fee process that depends upon the level of appeal and also the contract with client hospital (S1422). The Appeal flat fee process checks the Appeal Level (e.g., $1^{st}/2^{nd}$ level or reconsideration, etc.) and adds the Flat fee process.

The Package may be moved to the mailroom department (1423).

The Clerk may add a tracking number (e.g., USPS tracking number) to the package and add the tracking number to information in the corresponding patient account under the Notes Tab (S1424).

In an embodiment, the process automatically checks the shipment after 21 days from the mail date by using the USPS tracking process (e.g., United States postal service tracking process) to confirm whether a package with the tracking number has been delivered (S1425).

If the process determines that the package has been delivered, the process sets a follow up flag and updates the account status to Appeal in review with carrier delivered (S1426). If the tracking # is not updated with delivered status by the USPS tracking process, then the Account status is updated to indicate Manual Review needed. Once the Account Status is updated with Delivered Status, the system notifies an investigator that they should contact the insurance company regarding the corresponding appeal letter.

If the process determines that the package has not been delivered, the process updates the Account status to Manual Review needed (S1427). For example, the system may include a graphical user interface that enables a user to review the appeals letters requiring a manual review based on these flags. For example, the user could discover that the mailing address of the insurance company is incorrect during the review, so the user can update the corresponding information and re-submit the appeal letter.

The system checks an appeal level of the claim (S1428), and based on the appeal level, the system decides how much to charge the client (S1429).

If the claim is missing information, then the status of the Account is set to indicate to an investigator that some information is needed (e.g., from hospital) in order to process the claim (S1430).

If the claim was denied due to missing information, the process determines whether the missing information is located on a system of the client (S1431). If the investigator finds the missing information, they update the claim and move to step S1406 For example, as discussed above, a claim needs a certain required set of information in order to process the claim and also sometimes insurance can deny the claim if they think that the performed procedure was not necessary. In that case, the claim has to be submitted with the Attending physician or operating physician notes. If the missing information is not available on the client system, then the Investigator submits the request to the Hospital and once the request is fulfilled, they update the missing information and submit the claim to the Insurance.

The investigators then determine whether the missing information has been received from the client system (S1432).

If the missing information is received from the client system, the process resumes to step S1405 (S1433).

If the missing information is not received from the client system, then the investigator resubmits the request to the client hospital (S1434). For example, a graphical user interface of the system can present the claims having missing information that need to be manually requested from the client using a Hospital Field Request.

FIG. 20A-C illustrates a graphical user interface (GUI) of the system according to an exemplary embodiment of the inventive concept that enables a user to access patient account information. The GUI may include a first field 2001 that enables a user to display patient account information for a particular client, and more specifically for one or more sites managed by the client. For example, the first field 2001 may include a first dropdown menu (e.g., Client) to enable the user to select an option to display patient account information for one of a plurality of clients and a second dropdown menu (e.g., Hospital Name) to enable a user to select an option to display patient account information for one of a plurality of sites of the one selected client.

The GUI may include a second field 2002 that lists all of the patient accounts of the selected client and selected site. For example, the second field 2002 may list a unique account number for each patient. The GUI may further include a third field 2003 that lists a name of a patient associated with each patient account. The GUI may further include a fourth field 2004 that lists the balance owed on each patient account. The GUI may further include a fifth field 2005 that indicates a date that a health care service was performed for a patient associated with the patent account. The GUI may further include a sixth field 2006 that lists the site where the service was performed.

The GUI may further include a seventh field 2007 that lists a status associated with each patient account. For example, the status could indicate that the billing for the patient is split plan billing, that an investigator should review a prior payment made to the patient account, that no claim is on file (e.g., a claim for payment based on the service to an insurance company was not submitted), a rebill is needed, awaiting additional information to bill (e.g., lacking social security number of patient, lacking address of patient, etc.), or insurance billed. Thus, an investigator can view the seventh field 2007 to quickly determine what action to take.

The GUI may further include an eighth field 2008 that identifies the investigator assigned to each patient account. Thus, an investigator can view the eighth field 2008 to determine which of the patient accounts they are assigned to investigate. The GUI may further include a ninth field 2009 that indicates the date that each patient account was received. For example, an agent of the client that is managing the system may be contracted to perform a certain task with respect to a patient account within a certain period of time from the date of receipt The GUI may further include a tenth field 2010 that indicates the insurance carrier or insurance company that is associated with each patient account. Thus, an investigator can view the tenth field 2010 to determine which insurance carrier to submit a claim for a given patent account.

In a preferred embodiment, the GUI includes an eleventh field 2011 that indicates the due date to submit a claim to the insurance carrier or indicates that the due date has past. In an exemplary embodiment, the due date is based on a submission timeframe (e.g., a time period), which is a length of time one has to submit a claim, counting from the date of discharge or date of service. For example, if a patient is discharged from the hospital on Jan. 1, 2018, and the payer time frame is 45 days, then the due date would be Feb. 16, 2018. Previous interfaces only recorded the discharge date and did not calculate or display the due date.

Each insurance carrier may have its own submission timeframe. Further, a same insurance company could apply a different submission timeframe to different healthcare providers (e.g., hospitals) based on a given contract with that provider. The system has knowledge of the submission timeframe of each insurance carrier that is to be applied to each client. The above-described Timely Filing & Due Date Process is used to calculate the due date for each patient account. The Timely Filing & Due Date Process may be run periodically since the contracted submission timeframes may change. Thus, the eleventh field 2011 can be updated dynamically so that the most up to date due date is displayed. Accordingly, an investigator can view the eleventh field 2011 to quickly determine which accounts they should devote their attention. For example, the investigator can determine the due date without having to open up another menu and without spending time manually calculating the due date.

In an exemplary embodiment, the due date in the eleventh field 2011 displays one of i) the due date for submitting a claim and ii) the due date for appealing a denied claim that was submitted. For example, initially the due date in the eleventh field 2011 displays the due date for submitting a claim to the corresponding insurance carrier, and after the claim has been submitted and denied by the insurance carrier, the due date displays the deadline date for appealing the denied claim. In this case, the status in the seventh field 2007 may update to indicate that the claim needs to be appealed or to indicate the reason the claim was denied.

Thus, a single field 2011 is used to display both the due date for submitting a claim and the due date for appealing a denied claim so the user does not need to bring up another window to determine the appeal deadline date.

In an exemplary embodiment, the eleventh field 2011 presents a given one of its rows in different visual styles (e.g., colors and/or fonts) to indicate the priority of submitting or resolving a claim associated with the corresponding patient account. For example, the text of the due date could be red to indicate it needs to be worked on first and green to indicate that work on the account can be delayed. If the due date of given account is past due, the priority associated with that account could be set to a lowest level. In an embodiment, the priority is based on the balance size. For example, even if an account has claims that are not due for 2-3 months, the account could be given a highest priority if the balance exceeds a threshold (e.g., if the balance is very high). The GUI also allows a user to sort and filter the results based on the due date information.

Figure 21A:
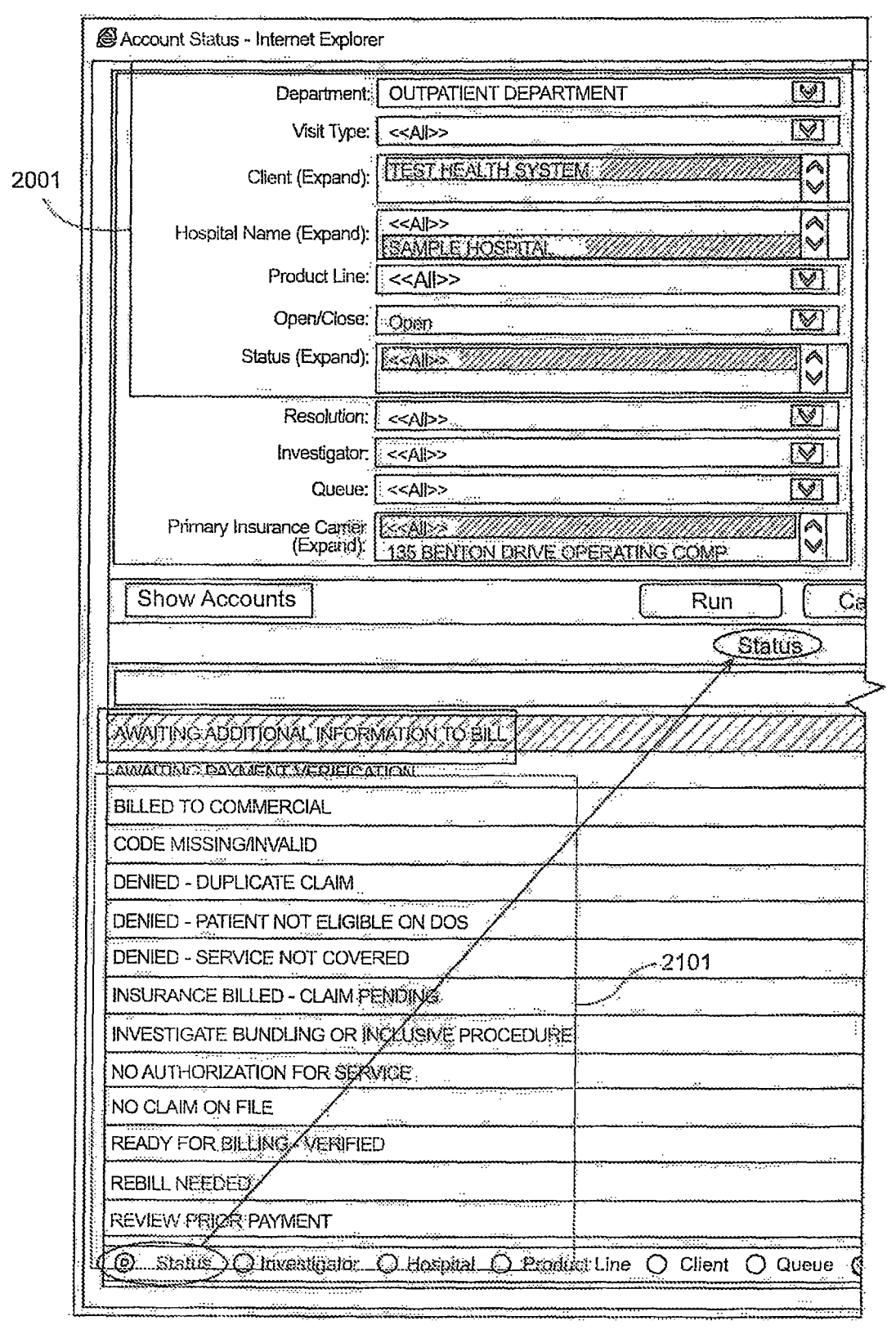

Thus, the user interface (i.e., the GUI) of FIG. 21A-C provides a particular manner of summarizing and presenting information in electronic devices. The user interface provides a specific manner of displaying a limited set of information to the user that differs from what was presented by conventional user interfaces. Conventional user interfaces had many deficits relating to the efficient functioning of the computer, requiring a user to scroll around and switch views many times to find the right data/functionality. Because small screens tend to need data and functionality divided into many layers or views, prior art interfaces requires users to drill down through many layers to get to the desired data or functionality. Accordingly, such prior art interfaces, are slower, more complex, and more difficult to learn, particularly to novice users. The user interface of FIG. 21A-C improves the efficiency of the electronic device by bringing together a limited set of commonly accessed stored data, which can be accessed directly from a main menu of the GUI. In particular, since the same field 2011 of GUI is capable of being dynamically updated to represent a first deadline for submitting the claim, updated to indicate the first deadline is past due, updated to represent a second deadline for appeal a denial of the claim, and further updated to indicate the second deadline is past due, an investigator can use a single menu without opening additionally menus to determine whether it is necessary to begin performing first work required for submitting a claim, to determine whether it is too late to begin this first work so another claim or appeal can be worked on, to determine whether the claim was submitted and denied, to determine whether it is necessary to begin performing second work required for appealing the denied claim, and to determine whether it is too late to begin this second work so another claim or appeal can be worked on. Thus, the speed of a user's navigation through various views and windows can be improved because it saves the user from navigating to the required application, opening it up, navigating within that application to enable the data of interest to be activated. Rather than paging through multiple screens of options, only 2 steps may be needed from start up to reaching the required data/functionality.

FIG. 21A-C illustrates a graphical user interface (GUI) of the system according to an exemplary embodiment of the inventive concept. The GUI may include the first field 2001 of FIG. 21A-C, which enables a user to display patient account information for a particular client. The GUI may include a window that presents status information on all the accounts that are being managed. The window may include a second field 2101 that lists all of the possible statuses (e.g., awaiting additional information to bill, awaiting payment verification, codes missing/invalid, denied due to being a duplicate claim, denied due to patient not being eligible, denied due to services not being covered, insurance billed/claim pending, investigate bundling, no authorization for services, no claim on file, ready for billing, rebill needed, review prior payment, etc.). The window may include a third field 2102 that lists the total balance for each of the listed statuses. For example, if the total balance for a given status is significantly higher than other statuses, the investigator can choose to investigate cases of this status. The window may further include a fourth field 2103 that lists the total number of accounts having each of the listed statuses. For example, if one of the statuses is only associated with a few accounts, but is associated with a high balance, it may be more efficient for the investigator to first target these accounts for resolution.

FIG. 22A-C illustrates a graphical user interface of the system according to an exemplary embodiment of the inventive concept. The GUI of FIG. 22A-C may be presented by a user selecting on one of the statuses listed in field 2101 in FIG. 21A-C. In the example shown in FIG. 22A-C, the user has selected the status of awaiting additional information to bill. Thus, in FIG. 22A-C, all of the patient accounts listed are those having the same status of awaiting additional information to bill.

Figure 23A:
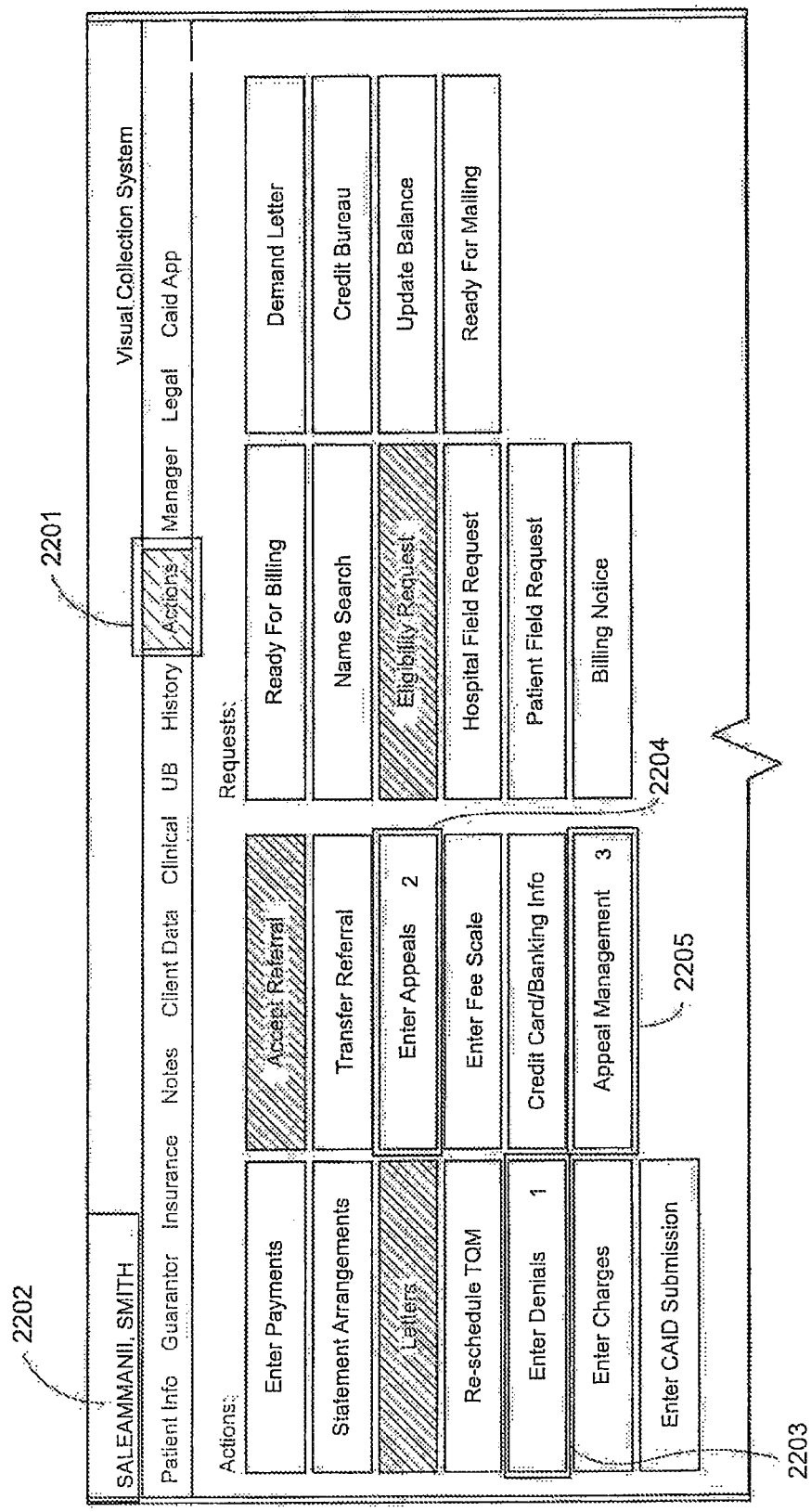
Figure 23B:
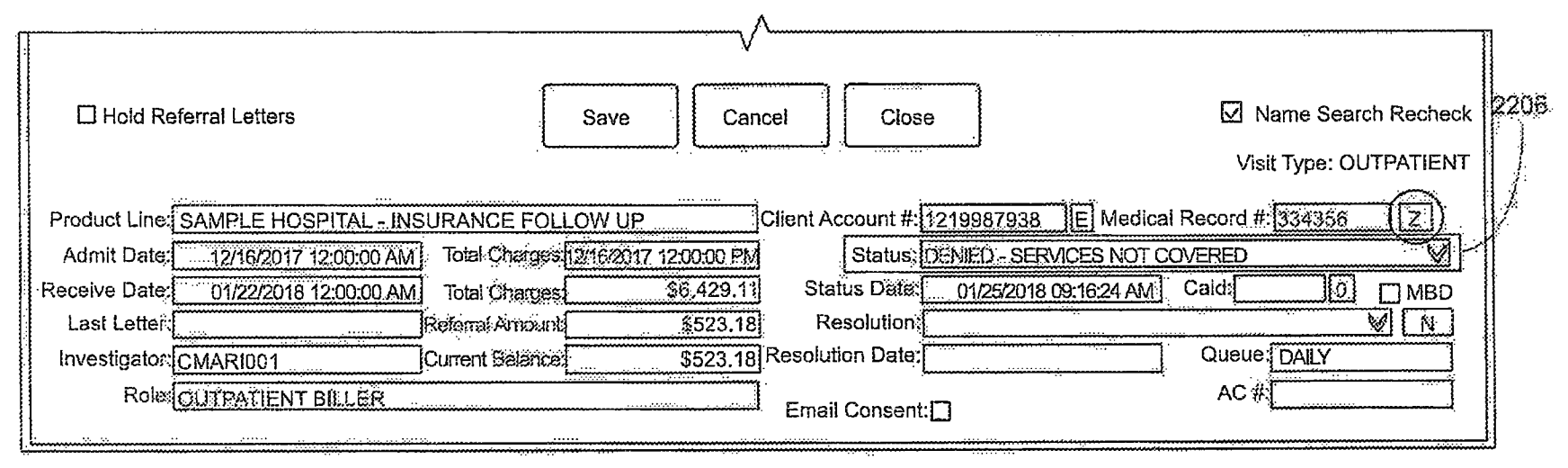

FIG. 23A-B illustrates a graphical user interface (GUI) of the system according to an exemplary embodiment of the inventive concept. The GUI (e.g., a pane) can be displayed by selecting an actions 2201 button. The GUI provides a user (e.g., the investigator) the ability to appeal a claim for a patient 2202 that was denied by an insurance company. The GUI includes a selectable option 2203 that enables the user to enter a denial associated with a claim of the patient of the system is not already aware of the specific denial, a selection option 2204 that enables the user to appeal an already denied claim, and a selectable option 2205 that enables the user to manage the appeal (e.g., edit an in-progress appeal). The GUI lists a status 2206 associated with the patient. In the example shown in FIG. 23A-B, the status 2206 indicates that a claim was denied because the services were not covered by the insurance of the patient. Thus, the user can review the status 2206 to determine whether an appeal should be submitted.

Figure 24A:
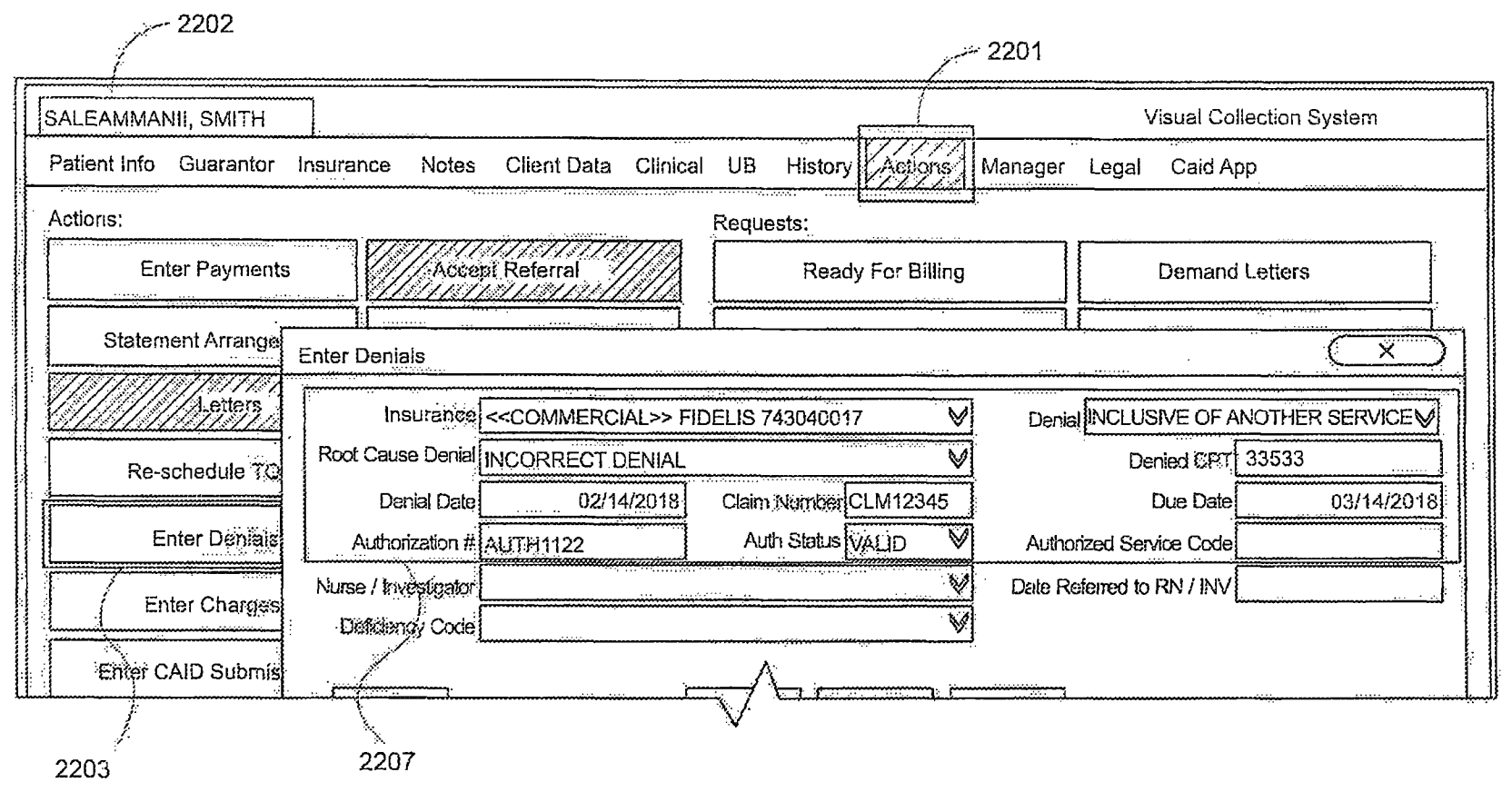
Figure 24B:
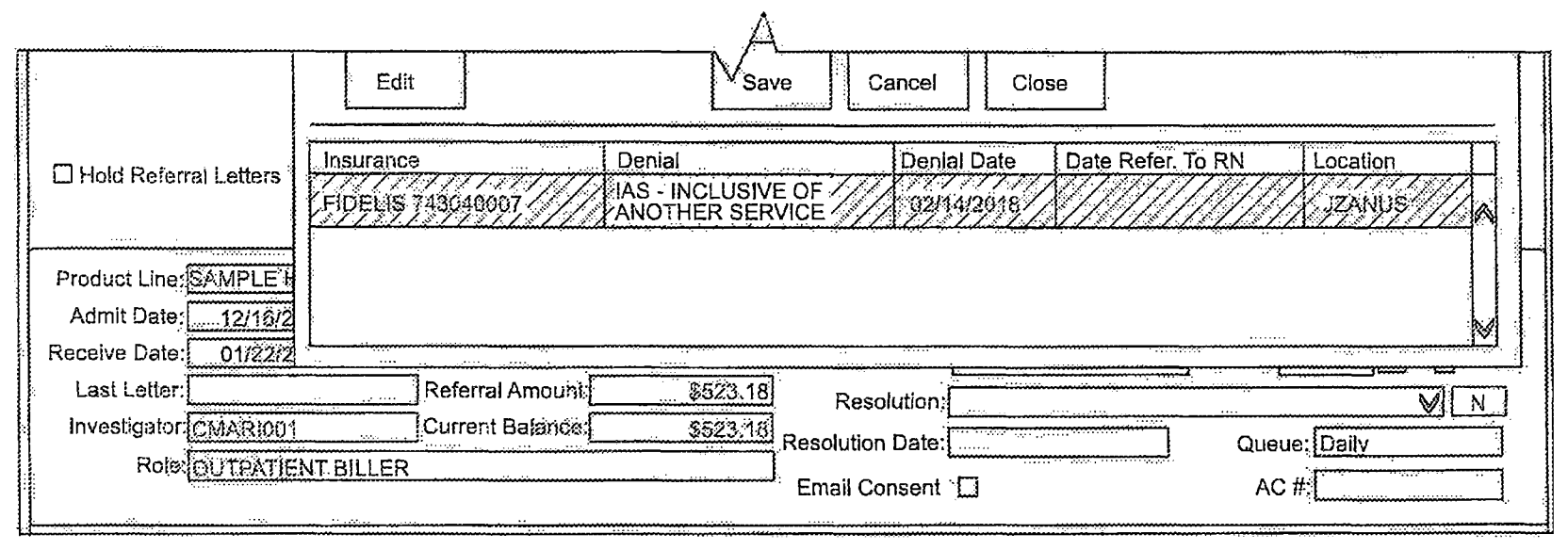

FIG. 24A-B illustrates a graphical user interface (GUI) of the system according to an exemplary embodiment of the inventive concept. The GUI is presented when the user selects the option 2203 for entering denials. The GUI includes a field 2207 for entering information about the denied claim such the identity of the insurance company of the patient, the cause of the denial, the type of denial, the due date for appealing the denial, and the identity of an investigator or a healthcare professional (e.g., a nurse) to which the appeal is to be assigned.

Figure 25A:
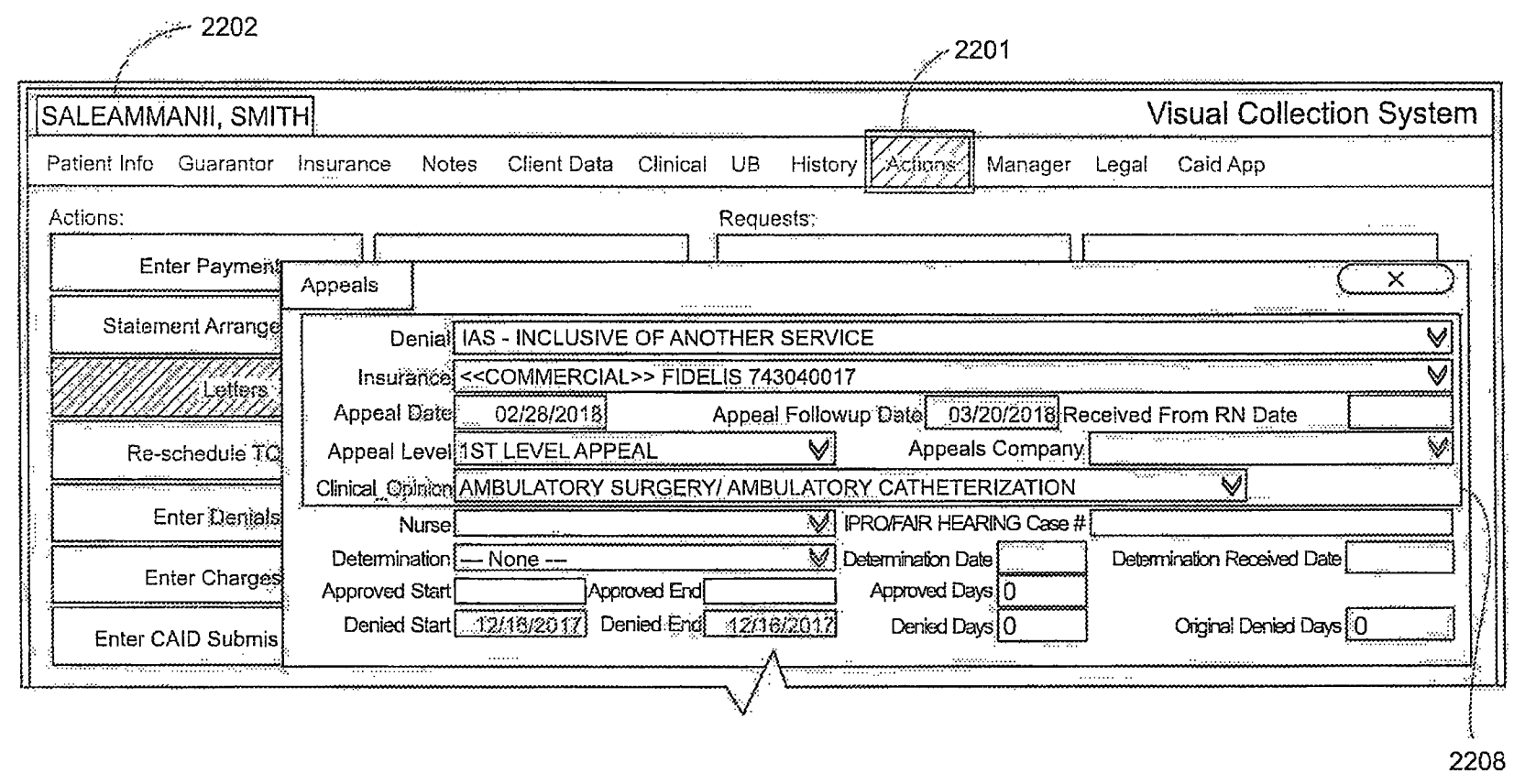
Figure 25B:
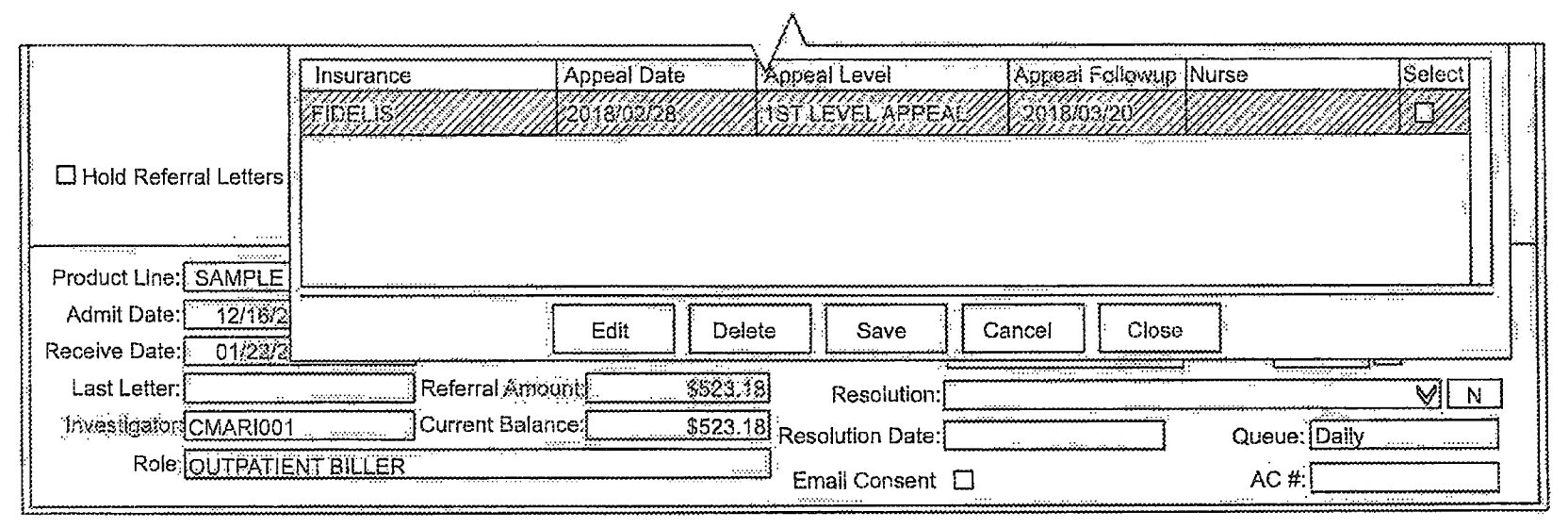

FIG. 25A-B illustrates a graphical user interface (GUI) of the system according to an exemplary embodiment of the inventive concept. The GUI is presented when the user selects the option 2204 for entering appeals. The GUI includes a field 2208 for entering and viewing information for the appeal such as the date of the appeal, the date the appeal should be followed up, the level of the appeal, a clinical opinion, and the date the claim was denied.

Figure 26:
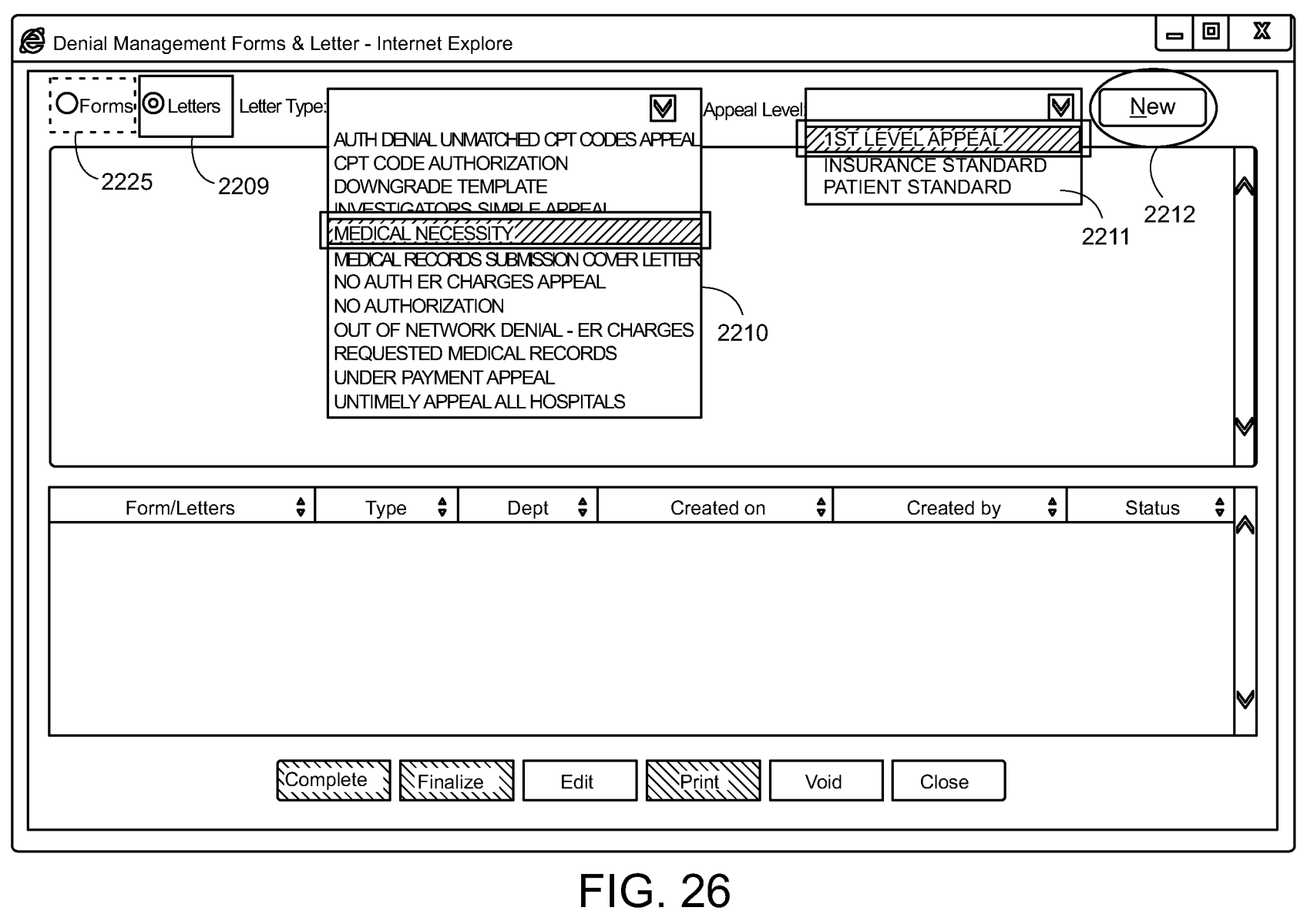

FIG. 26 illustrates a graphical user interface (GUI) of the system according to an exemplary embodiment of the inventive concept. The GUI is presented when the user selects the option 2205 for appeal management. The GUI includes an option 2209 for selecting one of a plurality of letters, an option 2210 for selecting the type of the letter (e.g., medical necessity, no authorization, out of network denial, requested medical records, untimely appeal, underpayment, etc.), one of a plurality of forms 2225, and an option 2211 for selecting an appeal level (e.g., $1^{st}$ level, insurance standard, patient standard, etc) of the appeal. Once the user selects the appropriate form/letter and type, the user can select an option 2212 to create the appeal. In an embodiment, the forms and letter templates are filtered by visit type. In the example shown in FIGS. 26-29, the patient had an outpatient visit and thus only outpatient letter templates are visible.

Figure 27A:
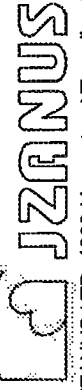

FIG. 27A-B illustrates a graphical user interface (GUI) of the system according to an exemplary embodiment of the inventive concept. The GUI is presented when the user selects the option 2212 to create the appeal. The GUI presents an option 2213 to select one of a plurality of types (e.g., letter types or form types) based on the visit type associated with the claim. In this example, the letter type is medical necessity, and accordingly the GUI presents a letter/form template for appealing a claim for the reason of a medical necessity. For example, certain insurance companies may deny a claim for a certain reason unless that claim is considered medically necessary by a healthcare provider. In an embodiment, the template includes editable and non-editable portions. The non-editable portions are automatically populated with data to reduce the chances of the appeal being denied. In an exemplary embodiment, the template includes a first portion 2214 (e.g., a header) that is non-editable and includes the return address of the agent (e.g., letterhead) who is appealing the claim on behalf of the patient or client (e.g., hospital) and the destination address of the insurance company to whom the appeal is being submitted. In the past, appeal letters were written manually and thus the portion including the addresses could include errors due to a human unintentionally entering the wrong address. For example, if an appeal letter includes an incorrect destination address, it is likely to be mailed to the wrong destination, and then the deadline for appealing the denial is likely to be missed. For example, if an appeal letter includes an incorrect return address, and the insurance company denies the appeal, it is unlikely the agent will receive mail from the insurance company notifying of the denial of appeal. For example, the notice typically includes the reasons the appeal was denied, which could be cured by the agent and resubmitted. Thus, the addition of the non-editable portion 2214 that automatically fills in the addresses greatly increases the chances of an appeal being accepted. In an embodiment, the template further includes an editable portion 2215. The editable portion 2215 may include an upper portion that is automatically filled with information based on the template type (e.g., appeal for medically necessary services), information about the client (e.g., name and address of hospital), visit type (e.g., outpatient service), information on the insurance company (e.g., identify of representative to send appeal), information about the denied claim (e.g., reason claim was denied, date service was provided, etc.). In an embodiment, the editable portion 2215 (e.g., body) includes a field 2216 that is automatically populated with the name and address of the client, a field 2217 that requires entry of the reason the claim was denied, and a field 2218 that is automatically populated with the date the service was provided. The field 2217 may initially include a graphic or text (e.g., xxxx) that informs the user that information should be entered here. The editable portion 2215 may include an additional editable portion that enables a user to enter factual reasons why the appeal should be approved. In this example, the user has entered a clinical summary into this portion explaining why the services were considered medically necessary. In an embodiment, the template further includes an optional non-editable portion 2219 (e.g., a footer) that includes an electronic signature of the user (e.g., the investigator). The footer may additionally include the role of the person associated with the signature their contact information (e.g., phone number). The GUI may include an option 2220 for saving the appeal.

Thus, the user interface (i.e., the GUI) of FIG. 27A-B provides a particular manner of summarizing and presenting information in electronic devices. The user interface provides a specific manner of displaying a limited set of information to the user that differs from what was presented by conventional user interfaces. Conventional user interfaces had many deficits relating to the efficient functioning of the computer, requiring a user to scroll around and switch views many times to find the right data/functionality. Because small screens tend to need data and functionality divided into many layers or views, prior art interfaces requires users to drill down through many layers to get to the desired data or functionality. Accordingly, such prior art interfaces, are slower, more complex, and more difficult to learn, particularly to novice users. The user interface of FIG. 27A-B improves the efficiency of the electronic device by bringing together a limited set of commonly accessed stored data and functions, which can be accessed directly from a main menu of the GUI. In particular, since the header 2214 and footer 2219 are non-editable and pre-populated with data, and the editable body 2215 additionally includes some pre-populated data (e.g., salutation, name of party appealing, type of appeal, identity of the patient, details of the claim, date of the service, identity of party providing service), it is not necessary for the user to open up additional menus to determine the information that is needed to be entered into the header 2214, the footer 2219 and the pre-populated portions of the body 2215. Thus, the speed of a user's navigation through various views and windows can be improved because it saves the user from navigating to the required application, opening it up, navigating within that application to enable the data of interest to be activated. Rather than paging through multiple screens of options, only 3 steps may be needed from start up to reaching the required data/functionality.

Figure 28A:
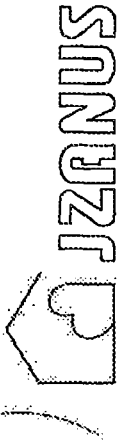
Figure 28B:
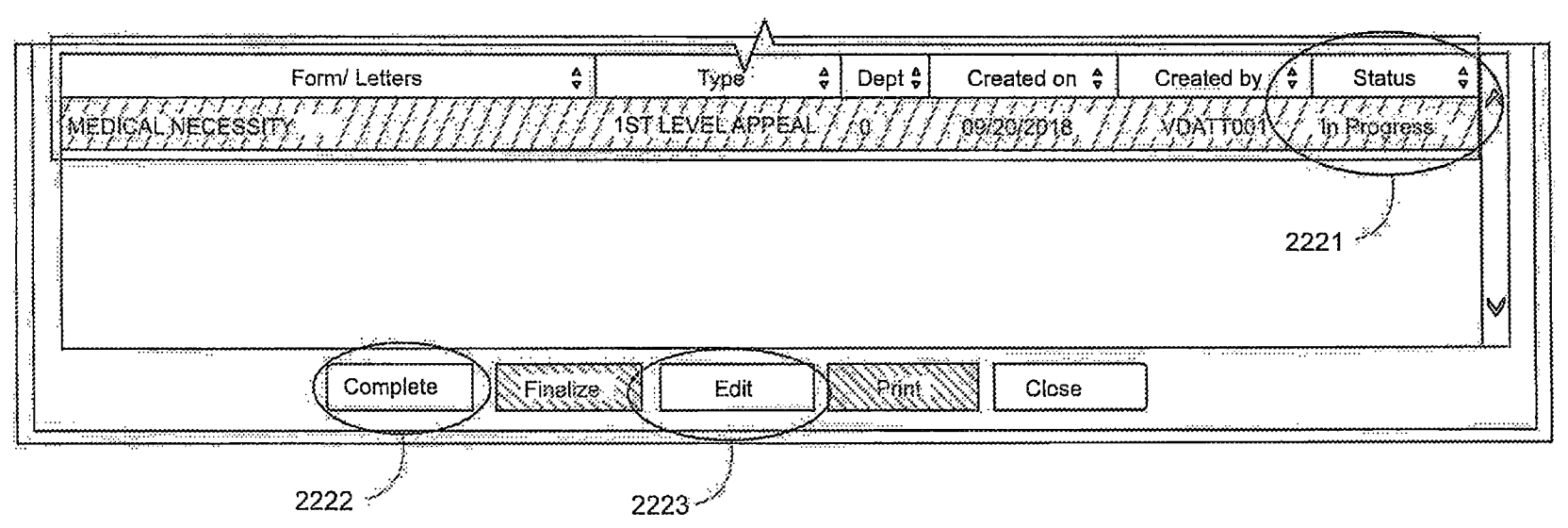

FIG. 28A-B illustrates a graphical user interface (GUI) of the system according to an exemplary embodiment of the inventive concept. The GUI is presented when the user selects the option 2220 to save the previously entered appeal. The GUI may present information 2221 that indicates the appeal is in-progress. While the appeal is in-progress, the user is able to go back and make changes to the appeal. For example, the user can select an option 2223 to edit the appeal. The GUI includes a preview window 2255 that enables the user to preview the in-progress appeal letter before deciding whether to select the option 2222 to complete the appeal letter. The preview window 2255 may include a slide bar that enables the user scroll through the entire appeal letter. Once the user has decided that no additional changes are needed, the user can select the option 2222 to complete the appeal. In an exemplary embodiment, once the option 2222 is selected, the GUI presents a warning message that warns the user will be unable to edit the appeal and includes options for abandoning the completion or confirming the completion. Once the appeal has been completed, the system can update the status of the account to indicate the clinical information needed for granting the appeal was received from a healthcare professional (e.g., received chart from RN).

Figure 29A:
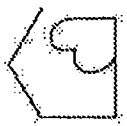
Figure 29B:
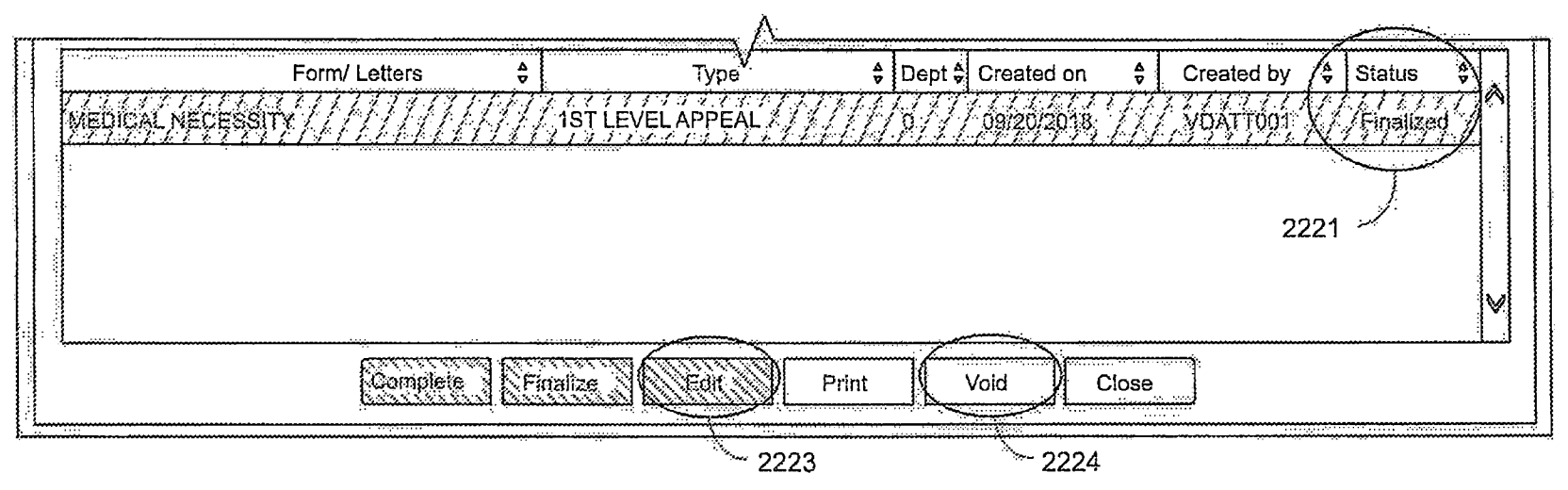

FIG. 29A-B illustrates a graphical user interface (GUI) of the system according to an exemplary embodiment of the inventive concept. The GUI may be presented when the user selects the option 2222 to complete the previously entered appeal. The GUI may present information 2221 that indicates the appeal is finalized. In an exemplary embodiment, the option 2223 for editing the appeal is grayed out to prevent the user from editing the appeal once the status of the appeal is set to finalized. In an exemplary embodiment, only a manager or supervisor can edit or void the appeal once it has been finalized. For example, a normal user is granted less permissions than a manager or supervisor. Thus, an individual, after logging in with credentials of the manager would experience a non-grayed out option 2223. Further, a void option 2224 may be presented to enable the manager to delete the previously entered appeal. In an exemplary embodiment, the system prevents the creation of a duplicate letter of appeal (e.g., same letter type and same appeal level) for a given patient account. For example, if a user tries to create a second letter with a type of medical necessity and an appeal level of $1^{st}$ level appeal, the GUI of the system will present a warning that the letter/form with the selected appeal type already exists.

Figure 30A:

FIG. 30A-B illustrates a graphical user interface (GUI) of the system according to an exemplary embodiment of the inventive concept. The GUI may be presented when the user selects the option 2225 for selecting one of a plurality of forms. The GUI may present a list 2226 of available forms such as a MISSING INFORMATION form, an RN LEVEL OF CARE CASE REVIEW form, and an RN NO APPEAL form. Appeal management forms may be linked with the client hospital and visit type.

Figure 31A:

FIG. 31A-B illustrates a graphical user interface (GUI) of the system according to an exemplary embodiment of the inventive concept. The GUI may be presented when the user selects the option 2225 to select one of the forms. The GUI includes a non-editable first portion 2300 (e.g., header) and an editable second portion 2301 (e.g., body). The GUI may include a third non-editable portion 2219 (e.g., a footer). The form shown in FIG. 31A-B is a MISSING INFORMATION form as an example. The first portion 2300 is automatically filled with information such as the name of the client (e.g., hospital), the name of the patient, the level of appeal, the account number, the date of service, and the reason for denial. In an embodiment, the second portion 2301 includes selectable options for the user to indicate what information is missing when the form is a missing information form.

Figure 32:
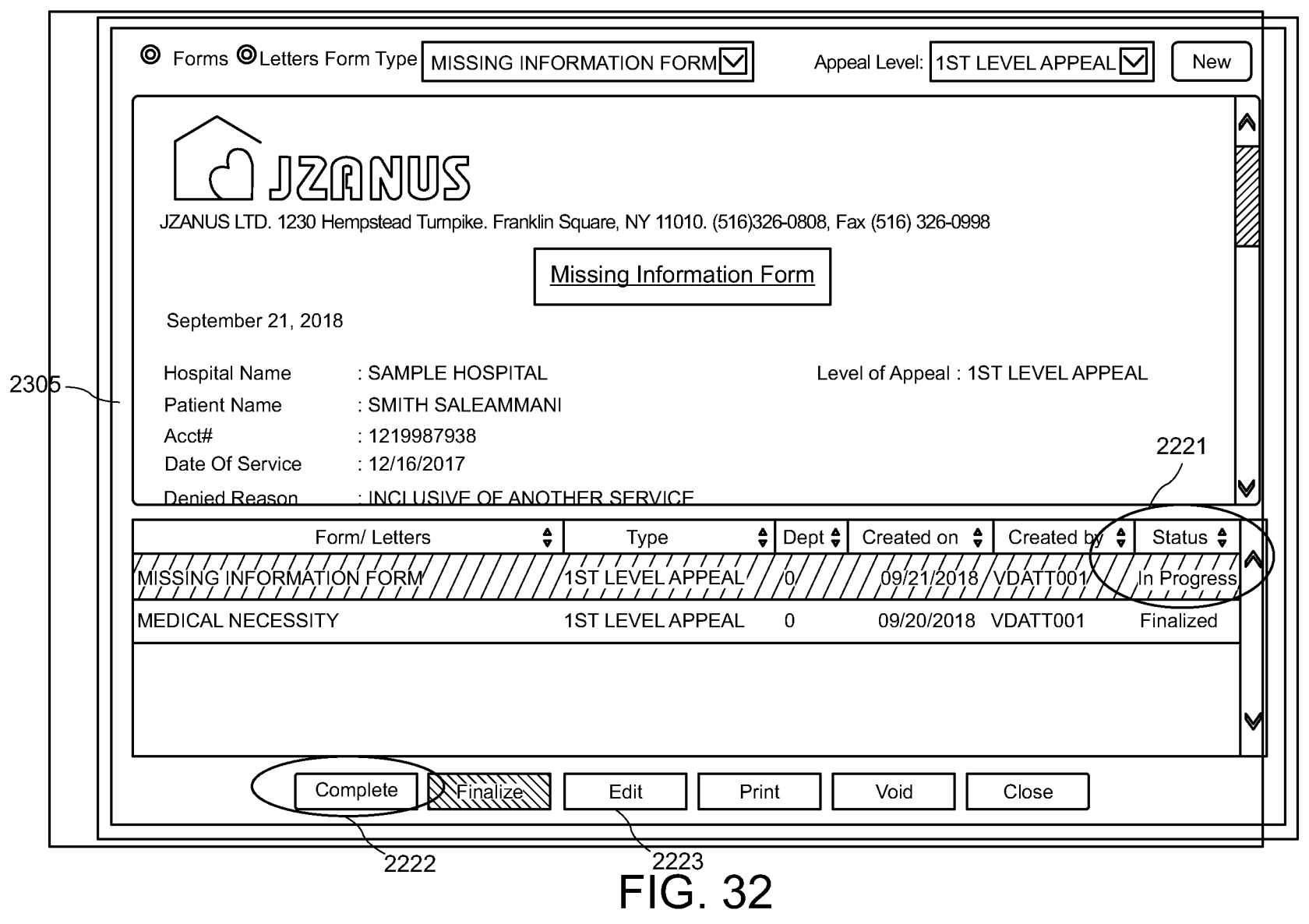

FIG. 32 illustrates a graphical user interface (GUI) of the system according to an exemplary embodiment of the inventive concept. The GUI is presented when the user selects the option 2220 to save the previously entered form. The GUI may present information 2221 that indicates the entry of the form is in-progress. While the form is in-progress, the user is able to go back and make changes to the form. For example, the user can select an option 2223 to edit the form. The GUI includes a preview window 2305 that enables the user to preview the in-progress from before deciding whether to select the option 2222 to complete the form. The preview window 2305 may include a slide bar that enables the user scroll through the entire form. Once the user has decided that no additional changes are needed, the user can select the option 2222 to complete the form. Although exemplary embodiments of the present invention have been described herein, those skilled in the art will readily appreciate that various modifications can be made in these exemplary embodiments without materially departing from the present invention. Accordingly, all such modifications are intended to be included within the scope of the disclosure.

Figure 33:
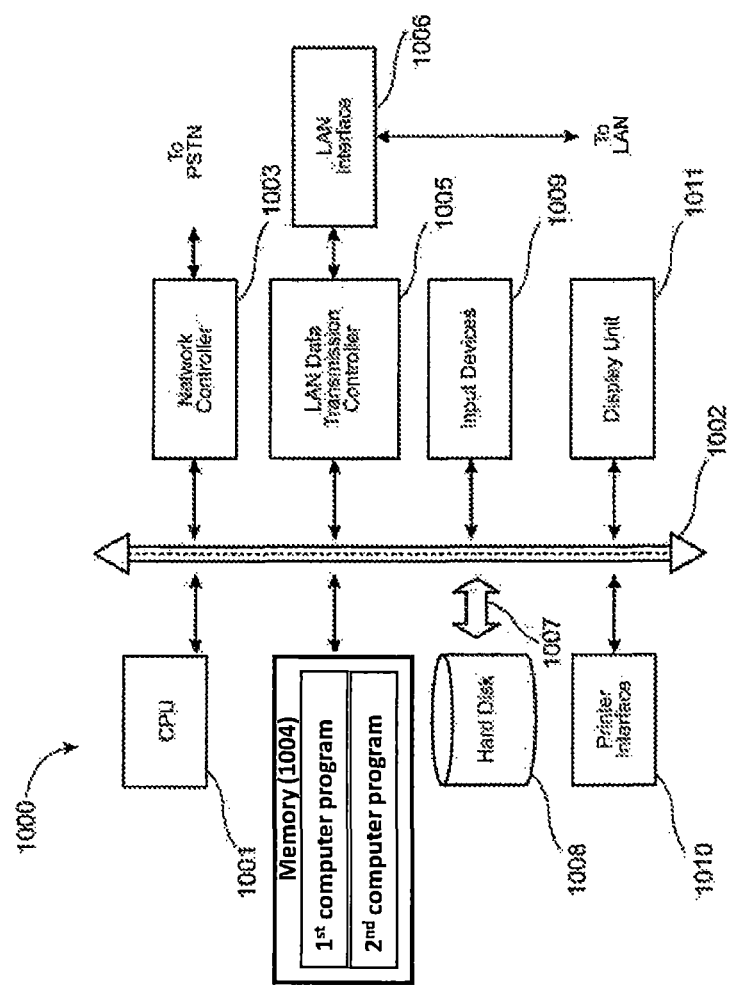
FIG. 33 illustrates an exemplary computer system that may be used to implement embodiments of one or more systems, methods or graphical user interfaces of the inventive concept.

FIG. 33 illustrates an exemplary computer system that may be used to implement embodiments of one or more systems, methods or graphical user interfaces of the inventive concept. Referring to FIG. 2, the computer system 1000 may include, for example, a central processing unit (CPU) 1001, random access memory (RAM) 1004, a printer interface 1010, a display unit 1011, a local area network (LAN) data transmission controller 1005, a LAN interface 1006, a network controller 1003, an internal bus 1002, and one or more input devices 1009, for example, a keyboard, mouse etc. As shown, the system 1000 may be connected to a data storage device, for example, a hard disk 1008 via a link 1007. The above described GUIs may be presented on the Display Unit 1011. The above-described computer programs may be stored in the memory 1004 and/or the hard disk 1008 and executed by the CPU 1001. The above-described database 110 may be stored in the stored in the memory 1004 and/or the hard disk 1008.

The various operations of methods described above may be performed by any suitable means capable of performing the operations, such as various hardware and/or software components, circuits, and/or modules. The software may comprise an ordered listing of executable instructions for implementing logical functions, and can be embodied in any processor-readable medium for use by or in connection with an instruction execution system, apparatus, or device, such as a single or multiple-core processor or processor-containing system. The functions may be stored in or transmitted over as one or more instructions or code on a tangible, non-transitory computer-readable medium.

What is claimed is:

1. A computing device for enabling a user to appeal denial of a medical claim, the computing device comprising:
a display device;
a memory storing a first computer program comprising a graphical user interface (GUI), a second computer program, and a database; and
a processor configured to execute the first computer program, the second computer program, and access the database,
wherein the second computer program is configured to periodically check a web-based location that is securely maintained by a computing device, and determine whether an electronic file indicating insurance information for each of a plurality of patient account numbers has been received by the web-based location, and upon determining that the electronic file has been received by the web-based location, perform an operation on the electronic file to generate patient account information for storage in a database,
wherein the GUI is configured to display a first menu on a display screen of the display device for one of the plurality of patient account numbers, and display selectable options on the screen reachable directly from the first menu,
wherein selection of a first one of the selectable options causes display of a second menu on the display screen, that enables a user to enter information indicating a medical claim of the one patient account was denied by insurance,
wherein selection of a second one of the selectable options causes display of a third menu on the display screen, that enables the user to enter information indicating the denied medical claim is being appealed, and
wherein selection of a third one of the selectable options causes display of a fourth menu on the display screen, including a list that enables selection of one of a plurality of appeal letter types and a fourth selectable option,
wherein selection of the fourth selectable option causes display of a fifth menu on the display screen, including a non-editable portion pre-filled with a destination address of the insurance from the insurance information of one of the patient account numbers associated with the medical claim, an editable portion for entering text in support of the appeal, and a fifth selectable option whose selection saves an in-progress copy of a letter of the selected appeal letter type including the portions,
wherein the non-editable portion prevents the user from changing text of the destination address.

2. The computing device of claim 1, wherein the non-editable portion is further configured to automatically present a return address of an agent that is appealing the medical claim on behalf of the one patient account, wherein the non-editable portion prevents the user from changing text of the return address.

3. The computing device of claim 1, wherein the non-editable portion is configured to automatically present a salutation of a representative of the insurance that accepts appeals, an identity of a healthcare provider providing a service associated with the denied medical claim, text based on the selected letter type, and a date the service was provided, wherein the non-editable portion prevents the user from changing text of the salutation.

4. The computing device of claim 3, wherein the fifth menu further includes an additional non-editable portion configured to automatically present a signature of an agent of the healthcare provider requesting the appeal, wherein the non-editable portion prevents the user from changing text of the signature.

5. The computing device of claim 1, wherein selection of the fifth selectable option causes display of a sixth menu on the display screen including a non-editable preview section enabling a user to scroll through the copy of the letter including the portions and a status section indicating a status of the letter as in-progress.

6. The computing device of claim 1, wherein the sixth menu includes a sixth selectable option whose selection causes the status of the letter to be set to finalized that prevents further editing of the letter.

7. The computing device of claim 1, wherein the GUI is configured to automatically present a template for appealing the medical claim when the user selects one of the letter types indicating a service associated with the denied medical claim was medically necessary.

8. A method for enabling a user to appeal denial of a medical claim, the method comprising:
   periodically checking a web-based location that is securely maintained by a computing device, and determining whether an electronic file indicating insurance information for each of a plurality of patient account numbers has been received by the web-based location;
   upon determining that the electronic file has been received by the web-based location, performing an operation on the electronic file to generate patient account information for storage in a database; and
   performing, by a graphical user interface (GUI), display of a first menu on a display screen of a display device for one of the plurality of patient account numbers, and display of selectable options on the screen reachable directly from the first menu,
   wherein selection of a first one of the selectable options causes display of a second menu on the display screen, that enables a user to enter information indicating a medical claim of the one patient account was denied by insurance,
   wherein selection of a second one of the selectable options causes display of a third menu on the display screen, that enables the user to enter information indicating the denied medical claim is being appealed,
   wherein selection of a third one of the selectable options causes display of a fourth menu on the display screen, including a list that enables selection of one of a plurality of appeal letter types and a fourth selectable option,
   wherein selection of the fourth selectable option causes display of a fifth menu on the display screen, including a non-editable portion pre-filled with a destination address of the insurance from the insurance information of one of the patient account numbers associated with the medical claim, an editable portion for entering text in support of the appeal, and a fifth selectable option whose selection saves an in-progress copy of a letter of the selected appeal letter type including the portions, and
   wherein the non-editable portion prevents the user from changing text of the destination address.

9. The method of claim 8, wherein the non-editable portion is further configured to automatically present a return address of an agent that is appealing the medical claim on behalf of the one patient account, wherein the non-edible portion prevents the user from changing text of the return address.

10. The method of claim 8, wherein the non-editable portion is configured to automatically present a salutation of a representative of the insurance that accepts appeals, an identity of a healthcare provider providing a service associated with the denied medical claim, text based on the selected letter type, and a date the service was provided, wherein the non-edible portion prevents the user from changing text of the salutation.

11. The method of claim 10, wherein the fifth menu further includes an additional non-editable portion configured to automatically present a signature of an agent of the healthcare provider requesting the appeal, wherein the non-edible portion prevents the user from changing text of the signature.

12. The method of claim 8, wherein selection of the fifth selectable option causes display of a sixth menu on the display screen including a non-editable preview section enabling a user to scroll through the copy of the letter including the portions and a status section indicating a status of the letter as in-progress.

13. The method of claim 8, wherein the sixth menu includes a sixth selectable option whose selection causes the status of the letter to be set to finalized that prevents further editing of the letter.

14. The method of claim 8, further comprising:
   automatically presenting, by the GUI, a template for appealing the medical claim when the user selects one of the letter types indicating a service associated with the denied medical claim was medically necessary.

* * * * *